United States Patent [19]
Flavin et al.

[11] Patent Number: 5,892,060
[45] Date of Patent: Apr. 6, 1999

[54] METHOD FOR THE PREPARATION OF (+)-CALANOLIDE A AND ANALOGUES THEREOF

[75] Inventors: Michael T. Flavin, Darien; Ze-Qi Xu, Naperville; Albert Khilevich, Glenview; David Zembower, Oak Park; John D. Rizzo, Downers Grove; Shuyuan Liao, Glen Ellyn; Aye Mar; Lin Lin, both of Chicago; Vilayphone Vilaychak, Elgin; Darko Brankovic, Bolingbrook; Sergey Dzekhster, Chicago; Jinjun Liu, Naperville, all of Ill.

[73] Assignee: Sarawak MediChem Pharmaceuticals, Inc., Lemont, Ill.

[21] Appl. No.: 609,537

[22] Filed: Mar. 1, 1996

Related U.S. Application Data

[63] Continuation-in-part of Ser. No. 510,213, Aug. 2, 1995, which is a continuation-in-part of Ser. No. 285,655, Aug. 3, 1994, Pat. No. 5,489,697.

[30] Foreign Application Priority Data

Aug. 2, 1995 [WO] WIPO .................... PCT/US95/09804

[51] Int. Cl.⁶ .............................................. C07D 407/14
[52] U.S. Cl. ........................................ 549/277; 549/278
[58] Field of Search ...................................... 549/277, 278

[56] References Cited

FOREIGN PATENT DOCUMENTS

WO 92/06695 4/1992 WIPO .
WO 93/20082 10/1993 WIPO .
WO 94/14789 7/1994 WIPO .
WO 94/28000 12/1994 WIPO .

OTHER PUBLICATIONS

Khilevich et al., (1996) *Chemical Abstracts*, vol. 125, No. 21, Abstract No. 275454.
Khilevich et al., (1996) "Synthesis of (+)-Calanolide A. and anti–HIV agent, via enzyme catalized resolution of the aldol products." *Tetrahedron Asymmetry*, vol. 7, No. 11, pp. 3315–3326.
Palmer et al., (1995) "Synthesis of the Calophyllum Coumarines. Part 2.", *Journal Of The Chemical Society*, Perkin Trans. I, pp. 3135–3152.
Rehder et al., (1996), *Chemical Abstracts*, vol. 125, No. 23, Abstract No. 300646.
Galinis et al., (1996) "Structre–activity modifications of the HIV Inhibitors (+)–Calanolide A and (−) Calanolide B.", *Journal of Medicinal Chemistry*, vol. 39, pp. 4507–4510.
Zembower et al., (1997) "Structural Analogues of the Calanolide Anti–HIV Agents. Modification of the Trans–10, 11–dimethyldihydropyran–12–ol Ring (Ring C)." *Journal of Medicinal Chemistry*, vol. 40, No. 6, pp. 1005–1017.
Barton et al. (1990), "Total Synthesis of Isorobustin," *Tet. Letters*, vol. 31, pp. 7449–7452.
Borch et al. (1971), "The Cyanohydridoborate Anion as a Selective Reducing Agent," *J. Amer. Chem. Soc.*, vol. 93, pp. 2897–2904.
Boyer et al. (1993), "Analysis of Nonnucleoside Drug–Resistant Variants of Human Immunodeficiency Virus Type 1 Reverse Transcriptase," *J. Virology*, vol. 67, pp. 2412–2420.
Brookmeyer, R. (1991), "Reconstruction and Future Trends of the AIDS Epidemic in the United States," *Science*, vol. 253, pp. 37–42.
Braun et al. (1990), "The Global Epidemiology of HIV Infection and AIDS," *Annu. Rev. Microbiol.*, vol. 44, pp. 555–577.
Buckheit et al. (1995), "Comparative Anti–HIV Evaluation of Diverse HIV–1–Specific Reverse Transcriptase Inhibitor–Resistant Virus Isolates Demonstrates the Existence of Distinct Phenotypic Subgroups," *Antiviral Research*, vol. 26, pp. 117–132.
Buckheit et al. (1995), "Resistance to 1–[(2–Hydroxyethoxy)methyl]–6–(phenylthio)thymine Derivatives is Generated by Mutations at Multiple Sites in the HIV–1 Reverse Transcriptase," *Virology*, vol. 210, pp. 186–193.
Cardellina et al. (1995), "Resolution and Comparative Anti–HIV Evaluation of the Enantiomers of Calanolides A and B," *Bioorg. Med. Chem. Lett.*, vol. 5, pp. 1011–1014.
Castro, B.R. (1983), "Replacement of Alcoholic Hydroxyl Groups by Halogens and Other Nucleophiles via Oxyphosphonium Intermediates," *Org. React.*, vol. 29, pp. 1–162.
Chenera et al. (1993), "Total Synthesis of (±)–Calanolide A, a Non–Nucleoside Inhibitor of HIV–1 Reverse Transcriptase," *J. Org. Chem.*, vol. 58, pp. 5605–5606.
Cooper et al. (1994), GR15987 and Related Analogues as Highly Potent, Orally Active Non–Peptide Neurokinin NK₂Receptor Antagonists, *Bioorganic & Med. Chem. Lett.*, vol. 4, pp. 1951–1956.
Crombie et al., (1987), "Synthesis of the Mammea Coumarin. Part 1. The Coumarin of the Mammea A, B, and C Series," *J. Chem. Perkin Trans.*, vol. 1, pp. 317–331.
Crombie et al. (1985), "Synthesis of Mammeins and Surangin A," *Tet. Letters*, vol. 26, pp. 2929–2932.
Crombie et al. (1966), "Isolation and Structure of Mammea B/BA, B/BB, B/BC and C/BB: A Group of 4–m–Propyl– and 4–n–Amyl–Coumarin Extractives of Mammea *Americana* L.," *Tet. Letters*, vol. 2, pp. 151–156.

(List continued on next page.)

*Primary Examiner*—Amelia Owens
*Attorney, Agent, or Firm*—McDonnell Boehnen; Hulbert & Berghoff

[57] ABSTRACT

A method of preparing (+)-calanolide A, 1, a potent HIV reverse transcriptase inhibitor, from chromene 4 is provided. According to the disclosed method, chromene 4 intermediate was subjected to a chlorotitanium-mediated aldol reaction with acetaldehyde to selectively produce (±)-8a. Separation and enzyme-mediated resolution of (±)-8a produced (+)-8a. Cyclization of (+)-8a under neutral Mitsunobu conditions followed by Luche reduction of (+)-7 produced (+)-calanolide A in high yield and enantiomeric purity. The method of the invention has been extended to produce potent antiviral calanolide A analogues.

22 Claims, 27 Drawing Sheets

OTHER PUBLICATIONS

De Clercq, E. (1992), "HIV Inhibitors Targeted at the Reverse Transcriptase," *AIDS Research and Human Retroviruses*, vol. 8, pp. 119–134.

Deshpande et al. (1995), "Synthesis of Optically Active Calanolides A and B," *J. Org. Chem.*, vol. 60, pp. 2964–2965.

Duthaler and Hafner (1992), "Chiral Titanium Complexes for Enantioselective Addition of Nucleophiles to Carbonyl Groups," *Chem. Rev.*, vol. 92, pp. 807–832.

Feuer et al. (1965), "The Reduction of Oximes with Diborane. A New Systhesis of N–Monosubstituted Hydroxylamines," *J. Org. Chem.*, vol. 30, pp. 2877–2880.

Feuer and Braunstein (1969), "The Reduction of Oximes, Oxime Ethers, and Oxime Esters with Diborane. A Novel Synthesis of Amines," *J. Org. Chem.*, vol. 34, pp. 1817–1821.

Fung et al. (1978), "Reduction by Tributyltin of Carbonyl Compounds Adsorbed on Silica Gel: Selective Reduction of Aldehydes," *J. Org. Chem.*, vol. 43, pp. 3977–3979.

Games et al. (1972), "Identification of 4–Phenyl and 4–Alkycoumarins in *Mammae Americana* L., *Mammea Africana* G. Don and Calophyllum Inophyllum by Gas Chromatography–Mass Spectrometry," *Tet. Letters*, vol. 31, pp. 3187–3190.

Gemal and Luche (1981), "Lanthanoids in Organic Synthesis. 6. The Reduction of $\alpha$–Enones by Sodium Borohydride in the Presence of Lanthanoid Chlorides: Synthetic and Mechanistic Aspects," *J. Am. Chem. Soc.*, vol. 103, pp. 5454–5459.

Gulakowski et al. (1991), "A semiautomated Multiparameter Approach for Anti–HIV Drug Screening," *J. Virol. Methods*, vol. 33, pp. 87–100.

Gustafson et al. (1994), "Calanone, A Novel Coumarin From *Calophyllum teysmannii*," *Tet. Letters*, vol. 35, pp. 5821–5824.

Hadden, J.W., (1991), "Immunotherapy of Human Immunodeficiency Virus Infection," *Trends Pharmocol Sci.*, vol. 12, pp. 107–111.

Hizi et al. (1993), "Specific Inhibition of the Reverse Transcriptase of Human Immunodeficiency Virus Type 1 and the Chimeric Enzymes of Human Immunodeficiency Virus Type 1 and Type 2 by Nonnuceloside Inhibitors," *Antimicrobial Agents and Chemotherapy*, vol. 37, pp. 1037–1042.

Hudlicky, M. (1988), "Fluorination with Diethylaminosulfur Trifluoride and Related Aminofluorosulfuranes," *Org. React.*, vol. 35, pp. 513–637.

Huff, J.R. (1991), "HIV Protease: A Novel Chemotherapeutic Target for AIDS," *J. Med. Chem.*, vol. 34, pp. 2305–2314.

Kashman et al. (1993). "The Calanolides, A Novel HIV–Inhibitory Class of Coumarin Derivatives from the Tropical Rainforest Tree, *Calophyllum lanigerum*," *J. Med. Chem.*, vol. 36, pp. 1110.

Kashman et al. (1992), "The Calanolides, a Novel HIV–Inhibitory Class of Coumarin Derivatives from the Tropical Rainforest Tree, *Calophyllum lanigerum*," *J. Med. Chem.*, vol. 35, pp. 2735–2743.

Kucherenko et al. (1995), "Novel Approach for Synthesis of ($\pm$)–Calanolide A and Its Anti–HIV Activity," *Tet. Letters*, vol. 36, pp. 5475–5478.

Larder et al. (1989), "HIV with reduced Sensitivity to Zidovudine (AZT) isolated during Prolonged Therapy," *Science*, vol. 243, pp. 1731–1734.

McKee et al. (1995), "The Pseudocalanolides: Structure Revision of Calanolides C and D," *J. Natural Products*, vol. 58, pp. 916–920.

Mitsunobu, O. (1981), "The Use of Diethyl Azodicarboxylate and Triphenylphosphine in Synthesis and Transformation of Natural Products," *Synthesis*, pp. 1–28.

Mitsuya et al. (1990), "Molecular Targets for AIDS Therapy," *Science*, vol. 49, pp. 1533–1544.

Mukaiyama, T. (1982), "The Directed Aldol Reaction," *Org. React.*, vol. 28, pp. 203–331.

Nielsen and Houlihan (1968), "The Aldol Condensation," *Org. React.*, vol. 16, pp. 1–438.

Nunberg et al. (1991), "Viral Resistance to Human Immunodeficiency Virus Type 1–specific Pyridinone Reverse Transcriptase," *J. Virol.*, vol. 65, pp. 4887–4892.

Palmer et al. (1994), "Synthesis of the *Calophyllum* coumarins," *Tet. Letters*, vol. 35, pp. 5363–5366.

Paterson et al. (1989), "Aldol Reactions in Polypropinonate Synthesis: High $\eta$–Face Selectivity of Enol Borinates from $\alpha$–Chiral Methyl and Ethyl Ketones under Substrate Control," *Tet. Letters*, vol. 30, pp. 7121–7124.

Petteway et al. (1991), "The Chronically Infected Cells: A Target for the Treatment of HIV Infection and AIDS," *Trends Pharmacol. Sci.*, vol. 12, pp. 28–34.

Rao et al. (1994), "A Concise Synthesis of Chiral 2–Methyl Chroman–4–ones: Stereo Selective Build–up of the Chromanol Moiety of Anti–HIV Agent, Calanolide A," *Tet. Letters*, vol. 35, pp. 6347–6350.

Reetz, M.T. (1984), "Chelation or Non–Chelation Control in Addition Reactions of Chiral $\alpha$– and $\beta$–Alkoxy Carbonyl Compounds," *Angew. Chem. Inc. Ed. Eng.*, vol. 23, pp. 556–569.

Richman, D.D. (1991), "Antiviral Therapy of HIV Infection," *Annu. Rev. Med.*, vol. 42, pp. 69–90.

Sethna and Phadke (1953), "The Pechmann Reaction," *Organic Reactions*, vol. 7, pp. 1–58.

Shibata and Baba (1994), "Organotin Enolates in Organic Synthesis," *Org. Prep. Proc. Int.*, vol. 26, pp. 85–100.

Széll et al. (1969), "Cyclization of Enol Esters of $\alpha$Acyloxyphenyl Alkyl Ketones, IV. A Kinetic Study of the Steps of the Kostanecki–Robinson Reaction," *Helvetica Chimica Acta*, vol. 52, pp. 2636–2641.

Tsunoda et al. (1995), "Mitsunobu Acylation of Sterically Congested Secondary Alcohols by $N,N,N^1,N^1$–Tetramethylazodicarboxamide–Tributylphosphine Reagents," *Tet. Letters*, vol. 36, pp. 2529–2530.

Wasserman et al. (1989). "The Chemistry of Vicinal Tricarbonyls, Use of Vinly Tricarbonyl Esters in the Formation of 3–Hydroxypyrrole–2–Carboxylates," *Tet. Letters*, vol. 30, pp. 1721–1724.

Weislow et al. (1989), "New Soluble–formazan Assay for HIV–1 Cytopathic Effects: Application to High–Flux Screening of Synthetic and Natural Products of AIDS–Antiviral Activity," *J. Natl. Cancer Inst.*, vol. 81, 577–586.

Hughes, D.L. (1992), "The Mitsunobu Reaction," *Organic Reaction*, vol. 42, pp. 335–656.

CA 121:200900 Gustafson et al 1994.

CA 121:170524 Patil et al 1994.

Bandara et al. (1986), "Two Chemically Distinct Groups of *Calophyllum* Species From Sri Lanka," *Phytochemistry*, vol. 25, pp. 425–428.

Boyd, M., "AIDS: Etiology, Diagnosis Treatment and Prevention," Chapter 18, 2nd Ed., J.B. Lippincott Co., Devita et al., ed., pp. 305–317.

Chaturvedi et al. (1974), "Anticonvulsant and Antinflammatory Activity of Natural Plant *Coumarins* and Triterpenoids," *Res. Communications in Chemical Pathology and Pharmacology*, vol. 9, pp. 11–22.

Craig et al. (1991), "Antiviral Properties of Ro 31–8959, An Inhibitor of Human Immunodeficiency Virus (HIV) Proteinase," *Antiviral Research*, vol. 16, pp. 295–305.

Dahanayake et al. (1974), "Chemical Investigation of Ceylonese Plants. Part VII. Extractives of *Calophyllum thwaitesii* Planch and Triana and *Calophyllum walkeri* Wight (Guttiferae)," *J.C.S. Perkin I*, pp. 2510–2514.

Dharmaratne et al. (1985), "*Triterpenoids* and *Coumarins* from the Leaves of *Calophyllum Cardato–Oblongum,*" *Phytochemistry*, vol. 24, pp. 1553–1556.

Dharmaratne et al. (1986), "Xanthones from Roots of Three calophyllum Species, " *Phytochemistry*, vol. 25, pp. 1957–1959.

Gautier et al. (1972), "Structure of Calophynic Acid, A Novel Constituent of *Calophyllum Inophyllum,*" *Tetrahedron Letters*, vol. 27, pp. 2715–2718.

Gunasekera et al. (1977), "Chemical Investigation of Ceylonese Plants. Part 27. Extractives of *Calophyllum cuneifolium* Thw. and *Calophyllum soulattri* Burm. F. (Guttiferae)," *J.C.S. Perkin I*, pp. 1505–1511.

Gunasekera et al. (1975), "Chemical Investigation of Ceylonese Plants. Part XVI. Extractives of *Calophyllum cardato–oblongum* Thw. (Guttiferae)," *J.C.S. Perkin I*, pp. 2215–2220.

Gunatilaka et al. (1984), "Terpenoid and Biflavanoid Constituents of *Calophyllum Calaba* and *Garcinia Spicata* From Sri lanka," *Phytochemistry*, vol. 23, pp. 323–328.

Gustafson et al. (1992), "A Nonpromoting Phorbol from the Samoan Medicinal Plant *Homalanthus nutans* Inhibits Cell Killing by HIV–1," *J. Med. Chem.*, vol. 35, pp. 1978–1986.

Gustafson et al. (1992), "AIDS–Antiviral Natural Products Research at the U.S. National Cancer Institute," in *Natural Products as Antiviral Agents*, Chu et al., eds. Plenum Press, New York, 1992, pp. 57–67.

Kawazu et al. (1972), "Piscicidal Constituents of *Capophyllum inophyllum,*" *Chemical Abstracts*, vol. 78, Abstract No. 13744F.

Kumar et al. (1982), "Calocalabaxanthone, The Putative Isoprenyl Precursor of Calabaxanthone From *Calophyllum Calaba,*" *Phytochemistry*, vol. 21, pp. 807–809.

Merigan et al. (1991), "Treatment of AIDS with Combinations of Antiretroviral Agents," *Am. J. of Medicine*, vol. 90, pp. 8S–17S.

McCaffrey et al. (1988), "A Rapid Fluorometric DNA Assay for the Measurement of Cell Density and Proliferation In Vitro," *In Vitro Cellular & Developmental Biology*, vol. 24, Part I, pp. 247–252

Ohtani et al. (1991), "A New Aspect of the High–Field of NMR Application of Mosher's Method. The Absolute Confirugation of Marine Triterpene Sipholenol–A," *J. Org. Chem.*, vol. 56, pp. 1296–1298.

Ohtani et al. (1989), "Absolute Configuration of Marine Diterpenes Possessing a Xenicane Skelton. An Application of an Advanced Mosher's Method," *Tetrahedron Letters*, vol. 30, pp. 3147–3150.

Pauwels et al. (1992), "Potent and Selective Inhibition of HIV–1 Replication In Vitro by a Novel Series of TIP Derivatives," *Nature*, vol. 343, pp. 470–474.

Rink et al. (1982), "Cytoplasmic pH and Free $Mg^{2+}$ in Lymphocytes," *J. of Cell Biology*, vol. 95, pp. 189–196.

Samaraweera et al. (1981), "Calozeylanic Acid, A New Bark Acid From Three Calophyllum Species," *Tetrahedron Letters*, vol. 22, pp. 5083–5086.

Saunders et al. (1992), "Non–nucleoside Inhibitors of HIV reverse Transcriptase," *Drug Design and Discovery*, vol. 8, pp. 255–263.

Shih et al. (1991), "Chimeric Human Immunodeficiency Virus Type 1/Type 2 Reverse Transcriptases Display Reversed Sensitivity to Nonnucleoside Analog Inhibitors," *Proc. Natl. Acad. Sci. USA*, vol. 88, pp. 9878–9882.

Stout et al. (1968), "Calophyllum Products III. The Structures of Blancoic Acids," *J. Organic Chemistry*, vol. 33, pp. 4185–4190.

Stout et al. (1964), "The Structure of Costatolide," *J. Organic Chemistry*, vol. 29, pp. 3604–3609.

Swagler et al. (1991), "Pharmacokinetics of Anti–HIV Nucleosides in Microswine," *J. Pharm. Pharmacol.*, vol. 43, pp. 823–826.

Soejarto et al. (1993), "Challenges in Developing a New Drug from Tropical Rain Forest Plants," In *Proceedings of the Symposium on the Industrial Utilization of Tropical Plants and the Conservation of Biodiversity*, Enugu, Nigeria, Feb. 14–19, 1993.

Somanathan et al. (1974), "Chemical Investigation of Ceylonese Plants. Part VIII. Trapezifolixanthone, a New Di–isoprenylated Xanthone from the Bark of *Calophyllum trapezifoluim* Thw. (Guttiferae)," *J.C.S. Perkin I*, pp. 2515–2517.

White et al. (1991), "A TIBO Derivative, R82913, Is A Potent Inhibitor of HIV–1 Reverse Transcriptase with Heteropolymer Templates," *Antiviral Research*, vol. 16, pp. 257–266.

Badner et al. (1991), "Oxathiin Carboxanilide, a Potent Inhibitor of Human Immunodeficiency Virus Reproduction," *Proc. Natl. Acad. Sci. USA*, vol. 88, pp. 6740–6744.

Buckheit et al. (1994), "Cell–Based and Biochemical Analysis of the Anti–HIV Activity of Combination of 3'–Azido–3'–Deoxythymidine and Analogues of TIBO," *Antiviral Chemistry & Chemotherapy*, vol. 5(1), pp. 35–42.

Hughes, D.L. (1992), "The Mitsunobu Reaction," *Organic Reaction*, vol. 42, pp. 335–656.

Kukla et al. (1991), "Synthesis and Anti–HIV–1 Activity of 4,5,6,7–Tetrahydro–5–methylimidazo[4,5,1–jk][1,4] benzodiazepin–2(1H)–one (TIBO) Derivatives," *J. Medicinal Chemistry*, vol. 34, pp. 746–751.

Lin et al. (1994), "Synthesis and Biological Evaluation of 2',3'–Dideoxy–L–pyrimidine Nucleosides as Potential Antiviral Agents Against Human Immunodeficiency Virus (HIV) and Hepatitis B virus (HBV)," *J. Med. Chem.*, vol. 37, pp. 798–803.

Massa et al. (1995), "Synthesis and Antiviral Activity of New 3,4–dihydro–2–alkoxy–6–benzyl–4–oxopyrimidines (DABOs), Specific Inhibitors of Human Immunodeficiency Virus Type 1," *Antiviral Chemistry and Chemotherapy*, vol. 6, pp. 1–8.

Mayaux et al. (1994), "Triterpene Derivatives that Block Entry of Human Immunodeficiency Virus Type 1 Into Cells, "*Proc. Natl. Acad. Sci. USA*, vol. 91, pp. 3564–3568.

McGuigan et al. (1994), "Synthesis and Anti–HIV Activity of Some Novel Diaryl Phosphate Derivatives of AZT," *Antiviral Research*, vol. 24, pp. 69–77.

McMahon et al. (1993), "Diarylsulfones, A New Chemical Class of Nucleoside Antiviral Inhibitors of Human Immunodeficiency Virus Type 1 Reverse Transcriptase," *Antimicrobial Agents and Chemotherapy*, vol. 37, pp. 754–760.

Meier et al. (1992), "O–Alkyl–5',5'–dinucleoside Phosphates as Prodrugs of 3'–Azidothymidine and Cordycepin," *J. Org. Chem.*, vol. 57, pp. 7300–7308.

Merluzzi et al. (1990), "Inhibition of HIV–1 Replication by a Nucleoside Reverse Transcriptase Inhibitor," *Science*, vol. 250, pp. 1411–1413.

Miyasaka et al. (1989), "A Novel Lead for Specific Anti–HIV–1 Agents: 1–[(2–Hydroxyethoxy)methyl]–6–(phenylthio)–thymine," *J. Medicinal Chemistry*, vol. 32, pp. 2507–2509.

Pauwels et al. (1990), "Potent and Selective Inhibition of HIV–1 Replication In Vitro by a Novel Series of TIBO Derivatives," *Nature*, vol. 343, pp. 470–474.

Pauwels et al. (1988), "Rapid and Automated Tetrazolium–Based Colorimetric Assay for the Detection of Anti–HIV Compounds," *J. Virological Methods*, vol. 309–321.

Sergheraert et al. (1993), Synthesis and Anti–HIV Evaluation of D4T and D4T 5'–Monophosphate Prodrugs, *J. Medicinal Chemistry*, vol. 36, pp. 826–830.

Cragg et al. (1993), Conservation of Biodiversity and the Potetntial for Development of Pharmaceutical Crops: Drug Discovery and Development at the United States National Cancer Institute, In *Proceedings of the Symposium on the Industrial Utilization of Tropical Plants and the Conservation of Biodiversity*, Enugu, Nigeria, Feb. 14–19.

Hertzberg et al. (1993), "Kinetic Studies of HIV–1 Reverse Transcriptase Inhibition by Inophyllums, A Novel Class of Non–Nucleoside Inhibitors, Using a Scintillation Proximity Assay," *Programs and Abstracts of the Third International Conference on the Biotechnology of Microbial Products: Novel Pharmacological and Agrobiological Activities*, P–42, 27, Apr. 1993.

Hertzberg et al. (1993), "Novel Methods for Antiviral Drug Discovery," *Programs and Abstracts of the Third International Conference on the Biotechnology of Microbial Products: Novel Pharmacological and Agrobiological Activities*, S–9, 17, Apr. 1993.

Mabberley, D.J. (1987), *The Plant Book*, Cambridge University Press, p. 92.

Patil et al. (1993), "The Inophyllums, Novel Inhibitors of HIV–1 Reverse Transcriptase," *Programs and Abstracts of the Third International Conference on the Biotechnology of Microbial Products: Novel Pharmacological and Agrobiological Activities*, P–31, 26, Apr. 1993.

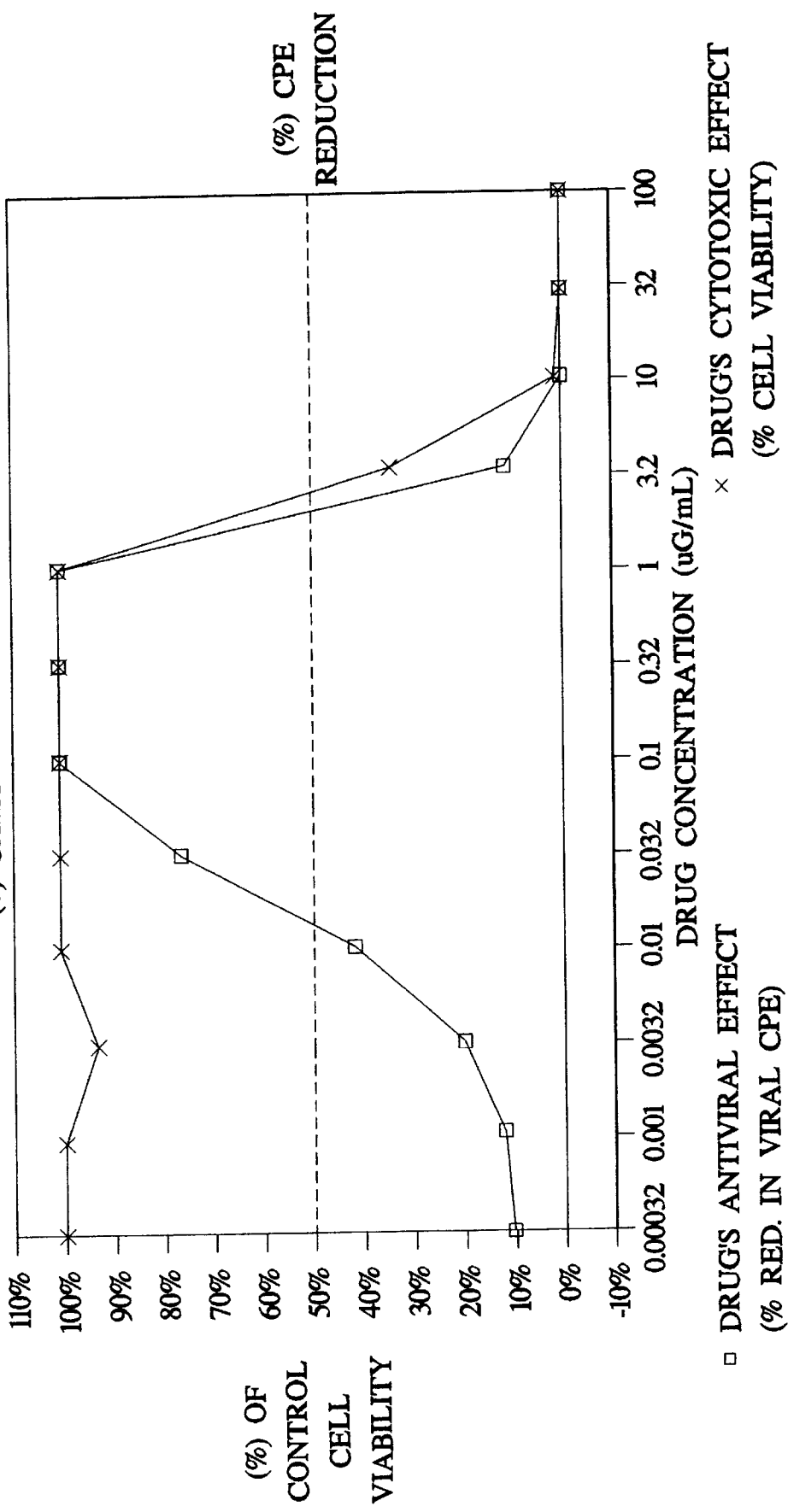

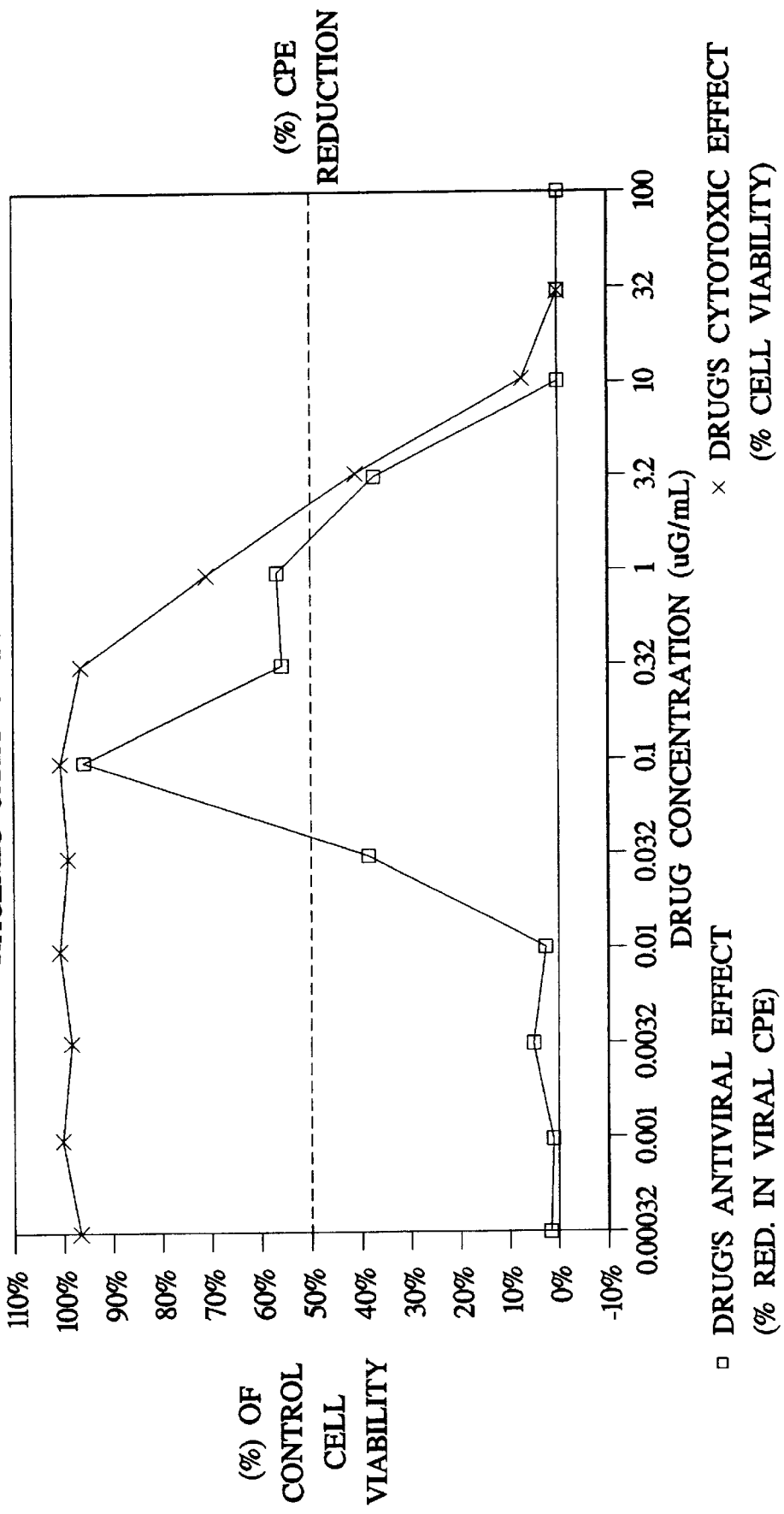

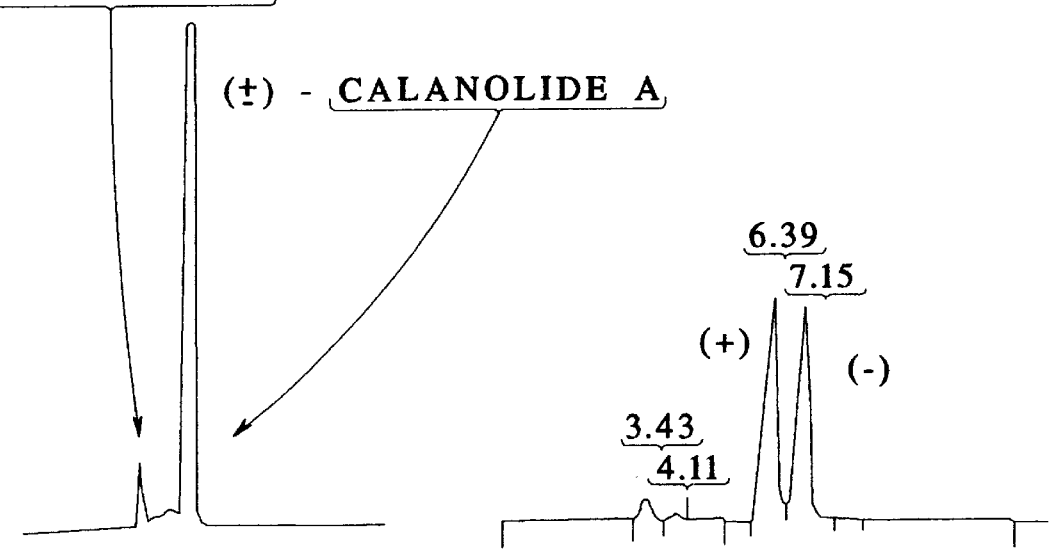
FIG. 6A
FIG. 6B
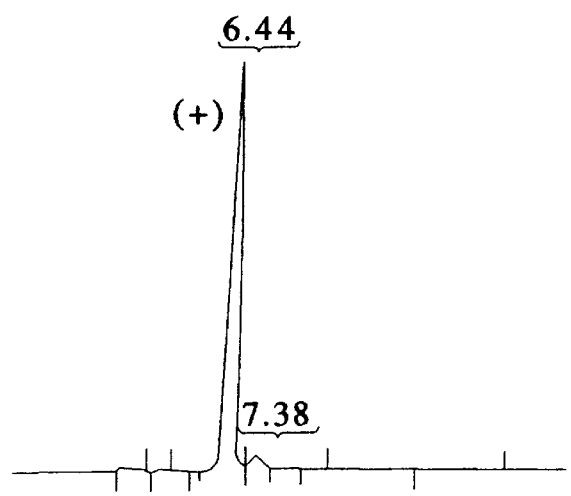
FIG. 6C
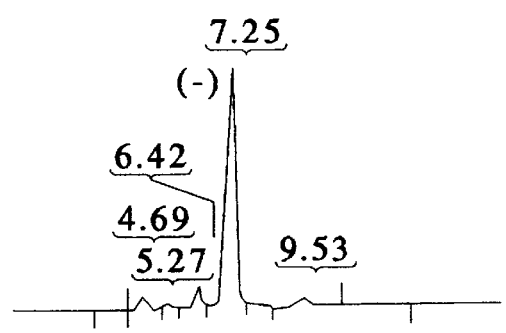
FIG. 6D 22          (-)-Calanolide B

METHOD FOR THE PREPARATION OF (+)-CALANOLIDE A AND ANALOGUES THEREOF

CROSS-REFERENCE

This is a continuation-in-part of co-pending U.S. patent application Ser. No. 08/510,213, filed Aug. 2, 1995, which in turn is a continuation-in-part of U.S. patent application Ser. No. 08/285,655, filed Aug. 3, 1994, now U.S. Pat. No. 5,489,697 issued Feb. 6, 1996.

FIELD OF THE INVENTION

This invention relates to a method for the preparation of (+)-calanolide A, a potent inhibitor of HIV reverse transcriptase, and calanolide A analogues. This invention also relates to the use of calanolide A analogues for treating or preventing viral infections.

BACKGROUND OF THE INVENTION

Human immunodeficiency virus (HIV), which is also called human T-lymphotropic virus type III (HTLV-III), lymphadenopathy-associated virus (LAV) or AIDS-associated retrovirus (ARV), was first isolated in 1982 and has been identified as the etiologic agent of the acquired immunodeficiency syndrome (AIDS) and related diseases. Since then, chemotherapy of AIDS has been one of the most challenging scientific endeavors. So far, AZT, ddC, ddI, 3TC and D4T have been approved by FDA and are being clinically used as drugs for the treatment of AIDS and AIDS-related complex. Although these FDA-approved drugs can extend the life of AIDS patients and improve their quality of life, none of these drugs are capable of curing the disease. Bone-marrow toxicity and other side effects as well as the emergence of drug-resistant viral strains limit the long-term use of these agents.[1] On the other hand, the number of AIDS patients worldwide has increased dramatically within the past decade and estimates of the reported cases in the very near future also continue to rise dramatically. It is therefore apparent that there is a great need for other promising drugs having improved selectivity and activity to combat AIDS.[1] Several approaches including chemical synthesis, natural products screening, and biotechnology have been utilized to identify compounds targeting different stages of HIV replication for therapeutic intervention.[2]

Very recently, the screening program at the National Cancer Institute has discovered a class of remarkably effective anti-HIV natural products, named calanolides, from the rain forest tree *Calophyllum lanigerum*, with calanolide A, 1, being the most potent compound in the reported series.[3] For example, calanolide A demonstrated 100% protection against the cytopathic effects of HIV-1, one of two distinct types of HIV, down to a concentration of 0.1 μM. This agent also halted HIV-1 replication in human T-lymphoblastic cells (CEM-SS) ($EC_{50}$=0.1 μM/$IC_{50}$=20 μM).[3] More interestingly and importantly, calanolide A was found to be active against both the AZT-resistant G-9106 strain of HIV as well as the pyridinone-resistant A17 virus.[3] Thus, the calanolides, known as HIV-1 specific reverse transcriptase inhibitors, represent novel anti-HIV chemotherapeutic agents for drug development.

A natural source of calanolide A is limited.[4] Consequently, a practical synthesis of the natural product must be developed for further study and development to be carried out on this active and promising series of compounds. Herein, we describe, a method for the synthesis of (±)-calanolide A, (+)-calanolide A and calanolide A analogues.

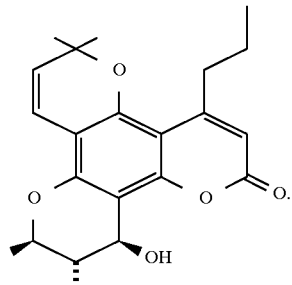

OBJECTS OF THE INVENTION

Accordingly, one object of the present invention is to provide a simple and practical method for preparing (+)-calanolide A, 1.

Another object of the invention is to provide calanolide A analogues and derivatives and method of preparation thereof.

A further object of the invention is to provide a method for treating or preventing viral infections using calanolide A analogues and derivatives.

These and other objects of the invention will become apparent in view of the detailed description below.

SUMMARY OF THE INVENTION

The present invention relates to methods for the syntheses of (+)-calanolide A and calanolide A analogues, and method of treating or preventing viral infections using calanolide A analogues and derivatives.

The method of the present invention for preparing (+)-calanolide A, 1, employs chromene 4 as the key intermediate. Chromene 4 is synthesized by the sequence depicted in Scheme I. Thus, 5,7-dihydroxy-4-propylcoumarin, 2,[5] was prepared quantitatively from ethyl butyrylacetate and phloroglucinol under Pechmann conditions.[6] Product yield and purity were dependent on the amount of sulfuric acid used. The 8-position of 5,7-dihydroxy-4-propylcoumarin, 2, was then selectively acylated at 8°–10° C. by propionyl chloride and $AlCl_3$ in a mixture of carbon disulfide and nitrobenzene to afford 5,7-dihydroxy-8-propionyl-4-propylcoumarin, 3.

In an alternative and preferred reaction, coumarin intermediate 3 may be produced in large scale quantities and with minimal formation of undesirable 6-position acylated product and 6,8-bis-acylated product by selective acylation of 5,7-dihydroxy-4-propylcoumarin 2 with a mixture of propionic anhydride and $AlCl_3$ at about 70°–75° C.

The chromene ring was introduced upon treatment of compound 3 with 4,4-dimethoxy-2-methylbutan-2-ol, providing 4 in 78% yield (Scheme I). Chlorotitanium-mediated aldol reaction of chromene 4 with acetaldehyde led to formation of (±)-8a and (±)-8b in a ratio of 95:5. The racemic syn aldol product [(±)-8a] was resolved by enzyme-catalyzed acylation. Thus, in the presence of lipase and vinyl acetate, (−)-8a was selectively acylated and the desired enantiomer (+)-8a was unreacted. The purified (+)-8a was subjected to a Mitsunobu[7a–c] reaction, exclusively leading to (+)-trans-chromanone[(+)-7].

Finally, Luche reduction[8] on (+)-7 led to formation of (+)-calanolide A [(+)-1] which contained 10% of (+)-calanolide B (see Scheme III). (+)-Calanolide A [(+)-1] was further separated from (+)-calanolide B by preparative normal phase HPLC and was identical with an authentic sample.

If desired, the racemic anti aldol product [(+)-8b] may also be resolved by enzyme-catalyzed acylation into (+)-8b and the ester 10 from (−)-8b (Scheme IV). Mitsunobu reaction on (+)-8b would lead to formation of the cis-chromanone 7a which could then be reduced to produce calanolide C.

The synthetic sequence for (+)-calanolide A was extended to the synthesis of calanolide analogues. Thus, Pechmann reaction of phloroglucinol with various β-ketoesters yields substituted 5,7-dihydroxycoumarin 11 (Scheme V). Friedel-Crafts acylation of substituted 5,7-dihydroxycoumarin 11 leads to formation of 8-acylated 5,7-dihydroxycoumarin 12. Chromenylation of 12 can be achieved by reacting with substituted β-hydroxyaldehyde dimethylacetal, affording chromenocoumarin 13. Aldol reaction of chromenocoumarin 13 with carbonyl compounds in the presence of LDA with or without metal complexing agents forms the racemic aldol product (±)-14. Cyclization of (±)-14 under Mitsunobu conditions, by using triphenylphosphine and diethyl azodicarboxylate (DEAD), leads to formation of chromanone analogue (±)-15. Reduction of (±)-15 with sodium borohydride with or without cerium chloride yields the 12-hydroxy analogue (±)-16 (Scheme V).

Catalytic hydrogenation of both (±)-15 and (±)-16 produces 7,8-dihydro derivatives (±)-17 and (±)-18 (Scheme VI). Treatment of (±)-15 with hydroxylamine or alkoxyamine affords oxime derivatives (±)-19 (Scheme VI). Reduction of (±)-19 under different conditions[9] should selectively yield hydroxylamino or amino compounds (20 and 21).

Optically active forms of 14–21 would be obtained by employing enzymatic acylation, as described in Scheme III for (+)-calanolide A [(+)-1]. Thus, enzyme-catalyzed acylation of the racemic aldol product (±)-14 would selectively acylate one enantiomer [i.e. (−)-14] and leave the other enantiomer [i.e. (+)-14] unreacted, which would be easily separated by conventional methods such as silica gel column chromatography. The acylated enantiomer [i.e. (−)-14] may be hydrolyzed to form the pure enantiomer [i.e. (−)-14]. The optically pure enantiomers thus obtained [(+)-14 and (−)-14] will be cyclized to (+)-15 and (−)-15, respectively, by Mitsunobu reaction. Reduction of (+)-15 and (−)-15 would lead to formation of (+)-16 and (−)-16. Hydrogenation of optically active forms of 15 and 16 would provide pure enantiomers of 17 and 18 [(+)-and (−)-17; (+)-and (−)-18]. Treatment of pure enantiomers of 15 with hydroxylamine and alkoxyamine affords enantiomerically pure oxime 19 [(+)-and (−)-19]. If desired, (+)-19 and (−)-19 may be reduced to produce enantiomerically pure 20 and 21 [(+)- and (−)-20; (+)-and (−)-21].

The 12-hydroxyl group in compound 1, 16, and 17 as well as their optically active forms can be epimerized by a number of methods including acidic conditions, neutral Mitsunobu conditions[7a−c], or with DAST.[7d] An example showing conversion of (−)-calanolide A [(−)-1] into (−)-calanolide B is depicted in Scheme VII.

The process of the present invention may be extended to prepare a wide variety of calanolide analogues such as Formulas I–VI shown in Scheme VIII wherein for Formulas I–V, $R_1$ is H, halogen, hydroxyl, amino, $C_{1-6}$ alkyl, aryl-$C_{1-6}$ alkyl, mono- or poly-fluorinated $C_{1-6}$ alkyl, hydroxy-$C_{1-6}$ alkyl, $C_{1-6}$ alkoxy, amino-$C_{1-8}$ alkyl, $C_{1-6}$ alkylamino, di($C_{1-6}$ alkyl)amino, $C_{1-8}$ alkylamino-$C_{1-8}$ alkyl, di($C_{1-6}$ alkyl) amino-$C_{1-8}$ alkyl, cyclohexyl, aryl or heterocycle, wherein aryl or heterocycle may each be unsubstituted or substituted with one or more of the following: $C_{1-6}$ alkyl, $C_{1-6}$ alkoxy, hydroxy-$C_{1-4}$ alkyl, hydroxyl, amino, $C_{1-6}$ alkylamino, di($C_{1-6}$ alkyl)amino, amino-$C_{1-8}$ alkyl, $C_{1-8}$ alkylamino-$C_{1-8}$ alkyl, di($C_{1-6}$ alkyl)amino-$C_{1-8}$ alkyl, nitro, azido or halogen;

$R_2$ is H, halogen, hydroxyl, $C_{1-6}$ alkyl, aryl-$C_{1-6}$ alkyl, mono- or poly-fluorinated $C_{1-6}$ alkyl, aryl or heterocycle;

$R_3$ and $R_4$ are independently selected from the group consisting of H, halogen, hydroxyl, amino, $C_{1-6}$ alkyl, aryl-$C_{1-6}$ alkyl, mono- or poly-fluorinated $C_{1-6}$ alkyl, hydroxy-$C_{1-6}$ alkyl, amino-$C_{1-8}$ alkyl, $C_{1-8}$ alkylamino-$C_{1-8}$ alkyl, di($C_{1-6}$ alkyl)amino-$C_{1-8}$ alkyl, cyclohexyl, aryl or heterocycle; and $R_3$ and $R_4$ can be taken together to form a 5–7 membered saturated cycle ring or heterocyclic ring;

$R_5$ and $R_6$ are independently selected from the group consisting of H, $C_{1-6}$ alkyl, aryl-$C_{1-6}$ alkyl, mono- or poly-fluorinated $C_{1-6}$ alkyl, aryl or heterocycle; and $R_5$ and $R_6$ can be taken together to form a 5–7 membered saturated cycle ring or heterocyclic ring;

$R_7$ is H, halogen, methyl, or ethyl;

$R_8$ and $R_9$ are independently selected from the group consisting of H, halogen, $C_{1-6}$ alkyl, aryl-$C_{1-6}$ alkyl, mono- or poly-fluorinated $C_{1-6}$ alkyl, amino-$C_{1-8}$ alkyl, $C_{1-8}$ alkylamino-$C_{1-8}$ alkyl,di($C_{1-6}$ alkyl)amino-$C_{1-8}$ alkyl, cyclohexyl, aryl or heterocycle; and $R_8$ and $R_9$ and be taken together to form a 5–7 membered saturated cycle ring or heterocyclic ring.

For Formula II compounds wherein $R_1$, $R_2$, $R_3$, $R_4$, $R_5$, $R_6$, $R_7$, $R_8$, and $R_9$ are the same as defined above, $R_{10}$ is H, acyl, P(O)(OH)$_2$, S(O)(OH)$_2$, CO($C_{1-10}$ alkyl)CO$_2$H, ($C_{1-8}$ alkyl)CO$_2$H, CO($C_{1-10}$ alkyl) NR$_{11}$ R$_{12}$, ($C_{1-8}$ alkyl) NR$_{11}$R$_{12}$; wherein R$_{11}$ and R$_{12}$ are independently selected from the group consisting of H, $C_{1-6}$ alkyl; and R$_{11}$ and R$_{12}$ can be taken together to form a 5–7 membered saturated heterocyclic ring containing said nitrogen.

For Formulae III and IV wherein $R_1$, $R_2$, $R_3$, $R_4$, $R_5$, $R_6$, $R_7$, $R_8$, and $R_9$ are the same as defined above, $R_{10}$ is halogen, OR$_{11}$, NHOR$_{11}$, NHOR$_{12}$, NR$_{11}$R$_{12}$, NR$_{12}$ R$_{13}$; wherein R$_{11}$, is H, acyl, P(O)(OH)$_2$, S(O)(OH)$_2$, CO($C_{1-10}$ alkyl) CO$_2$H, ($C_{1-8}$ alkyl)CO$_2$H, CO($C_{1-10}$ alkyl)NR$_{12}$ R$_{13}$, ($C_{1-8}$ alkyl) NR$_{12}$R$_{13}$; R$_{12}$ and R$_{13}$ are independently selected from the group consisting of H, $C_{1-6}$ alkyl; and R$_{12}$ and R$_{13}$ can be taken together to form a 5–7 membered saturated heterocyclic ring containing said nitrogen.

For Formula VI compounds, wherein $R_1$, $R_2$, $R_3$, $R_4$, $R_5$, $R_6$, $R_7$, $R_8$, and $R_9$ are the same as defined above, $R_{10}$ is H, $C_{1-6}$ alkyl, aryl or aryl $C_{1-6}$alkyl.

SCHEME I
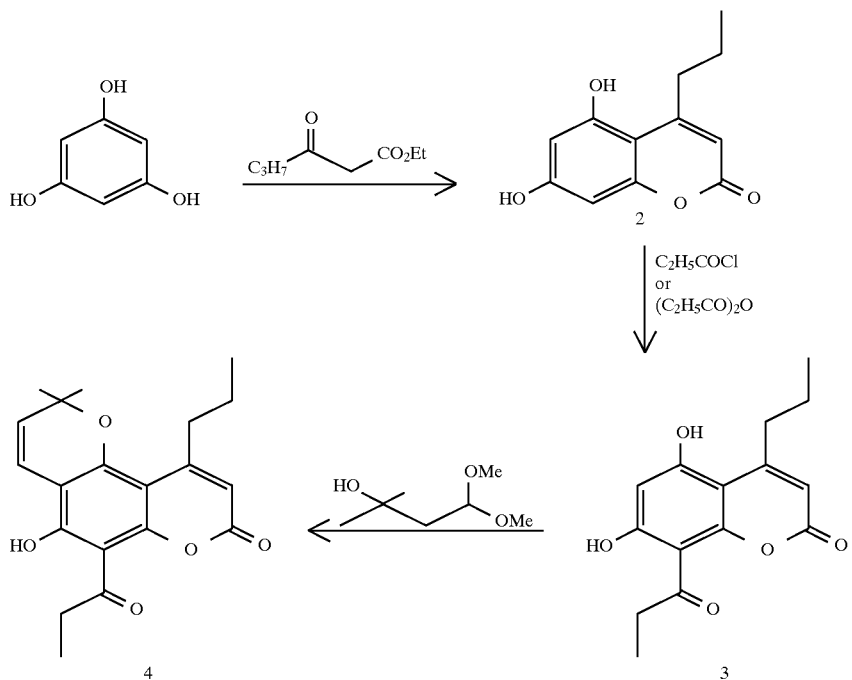
SCHEME II
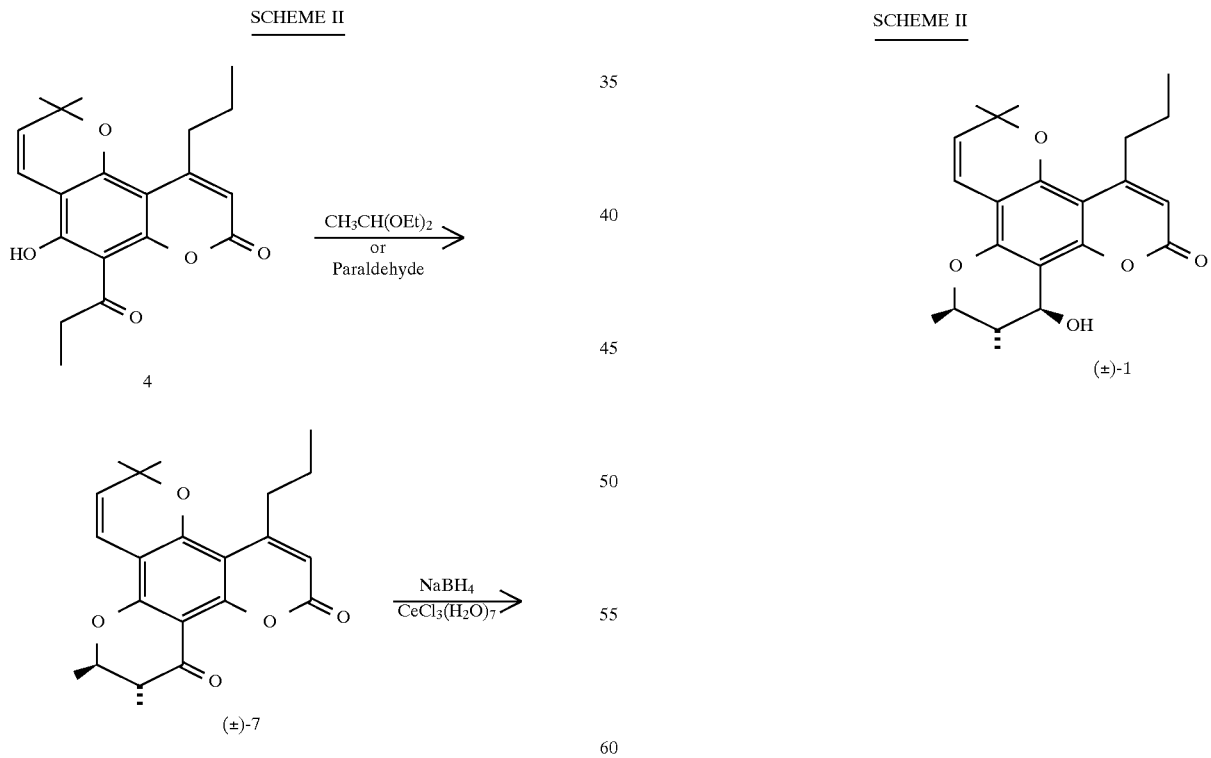

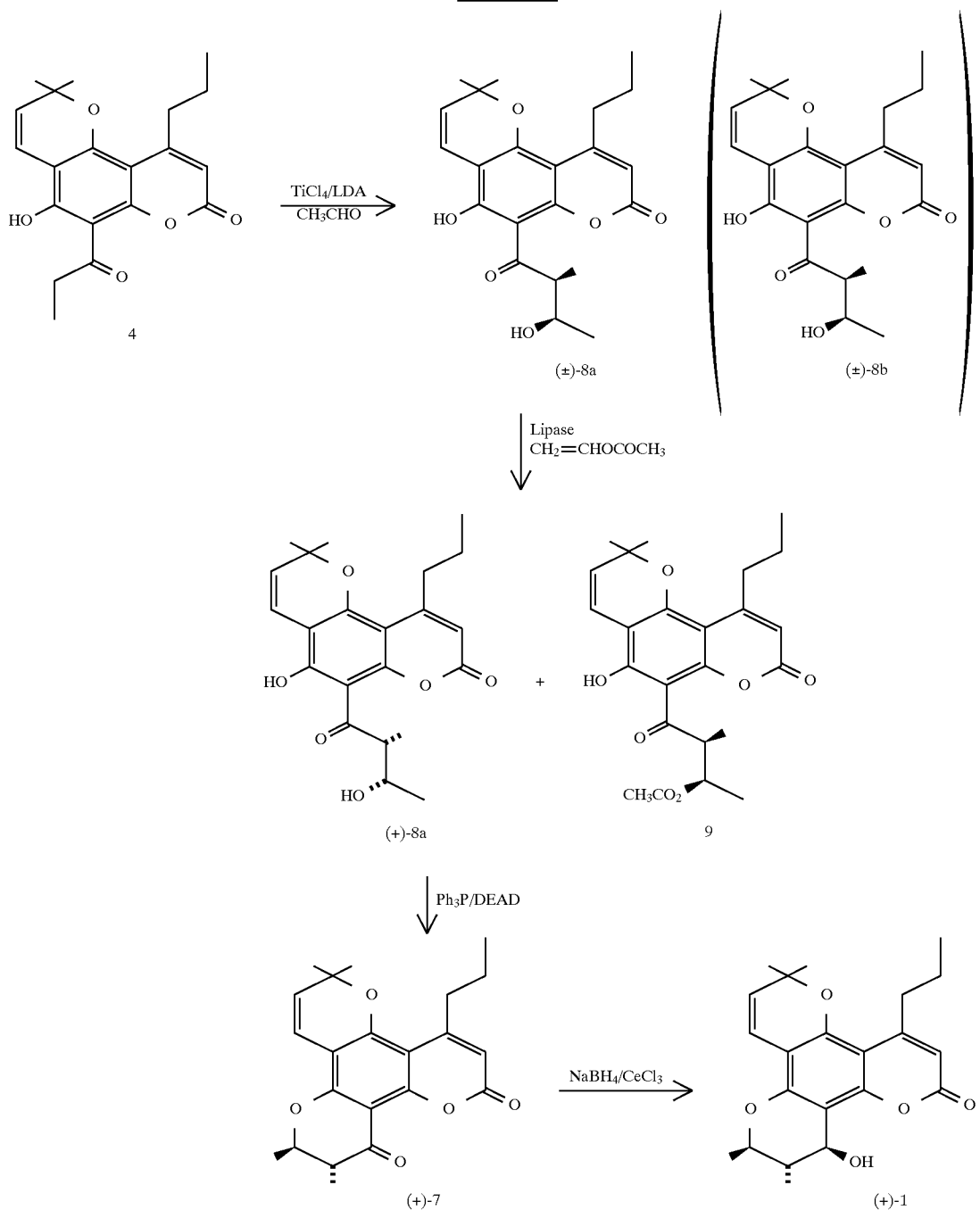
Scheme III

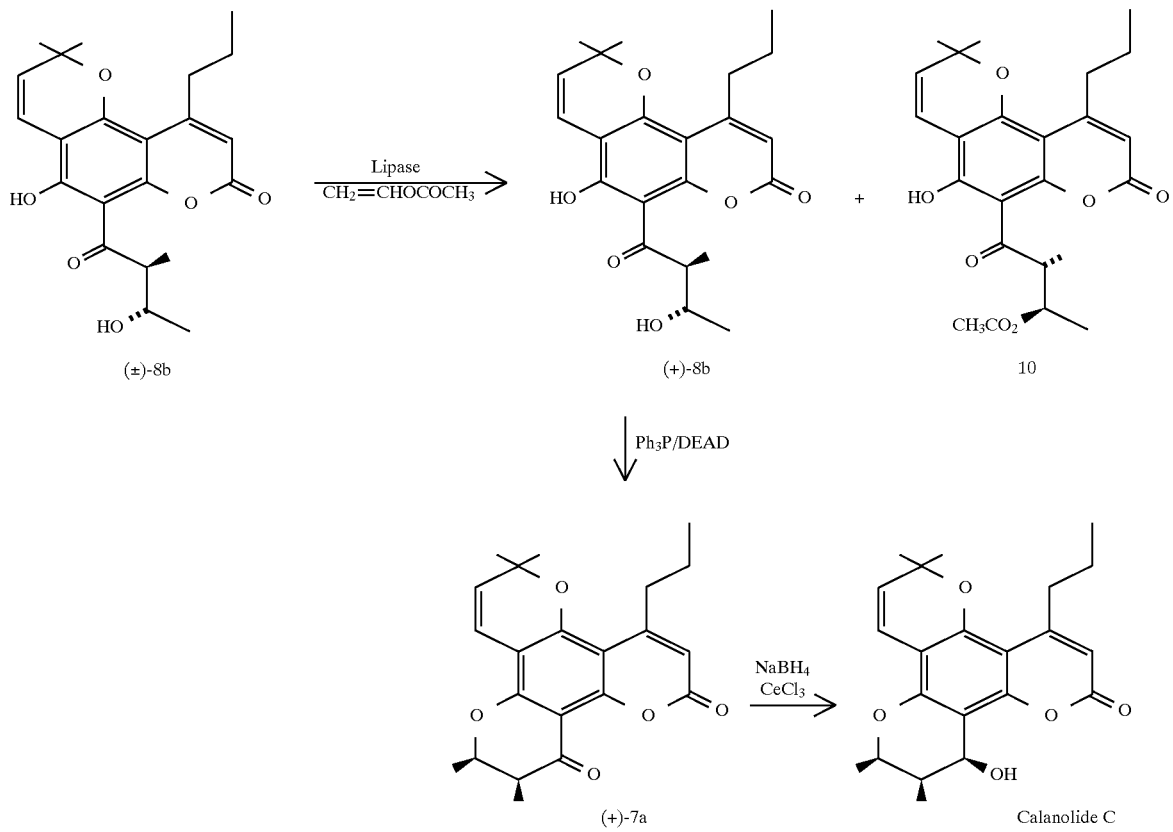
Scheme IV
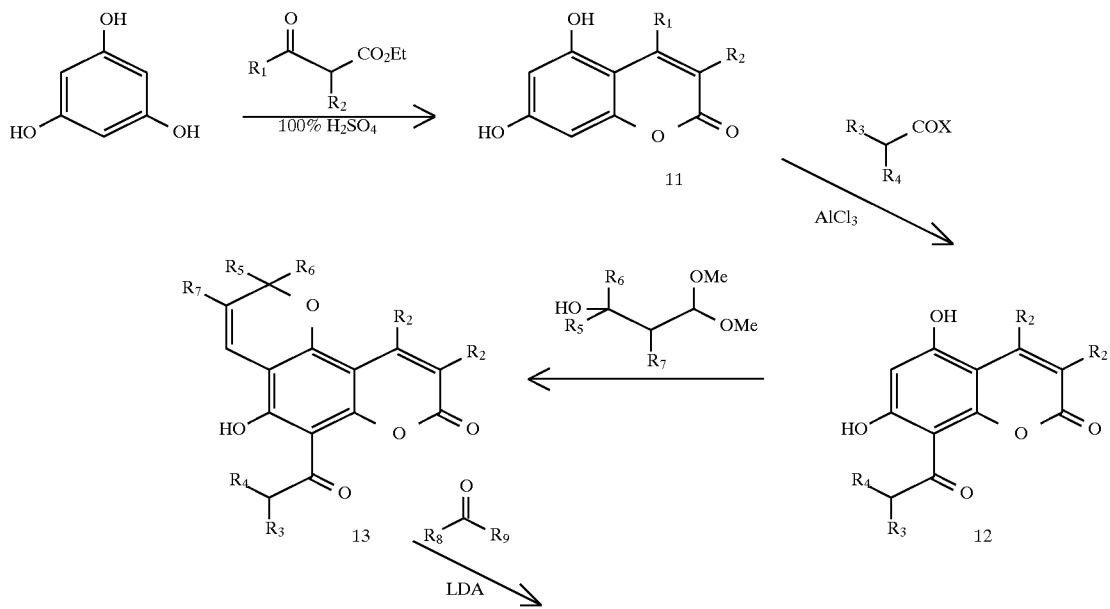
Scheme V

-continued
Scheme V
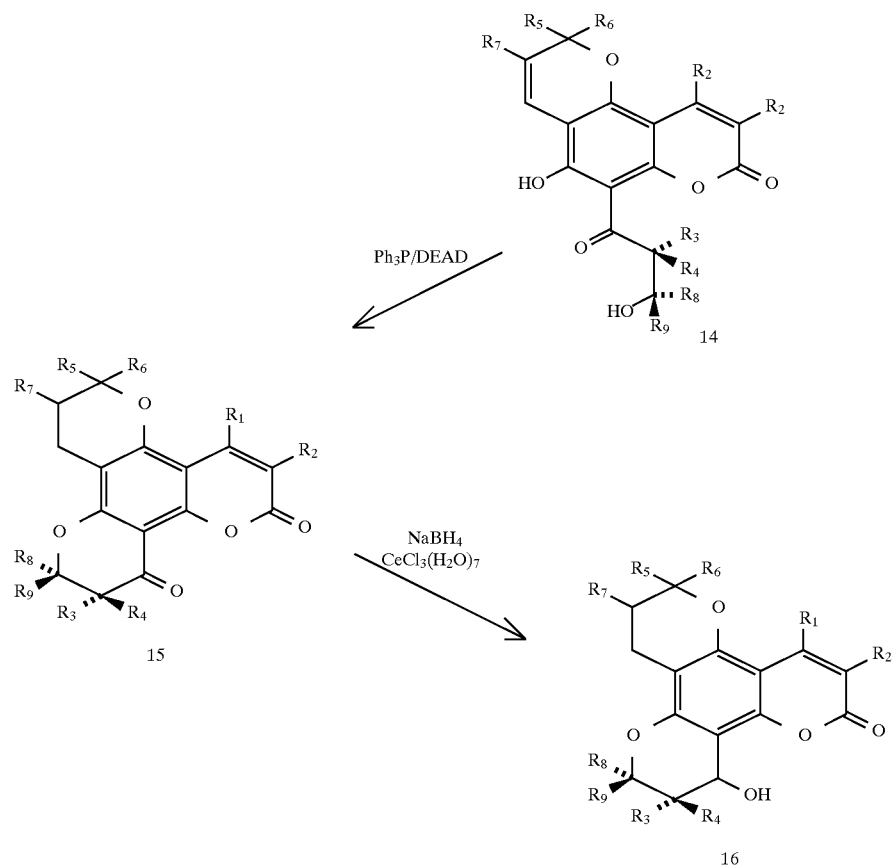
Scheme VI
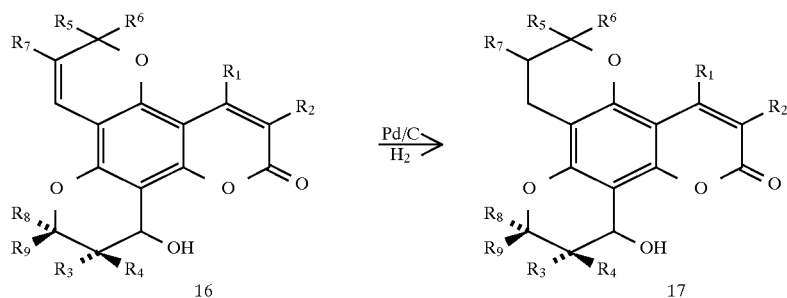

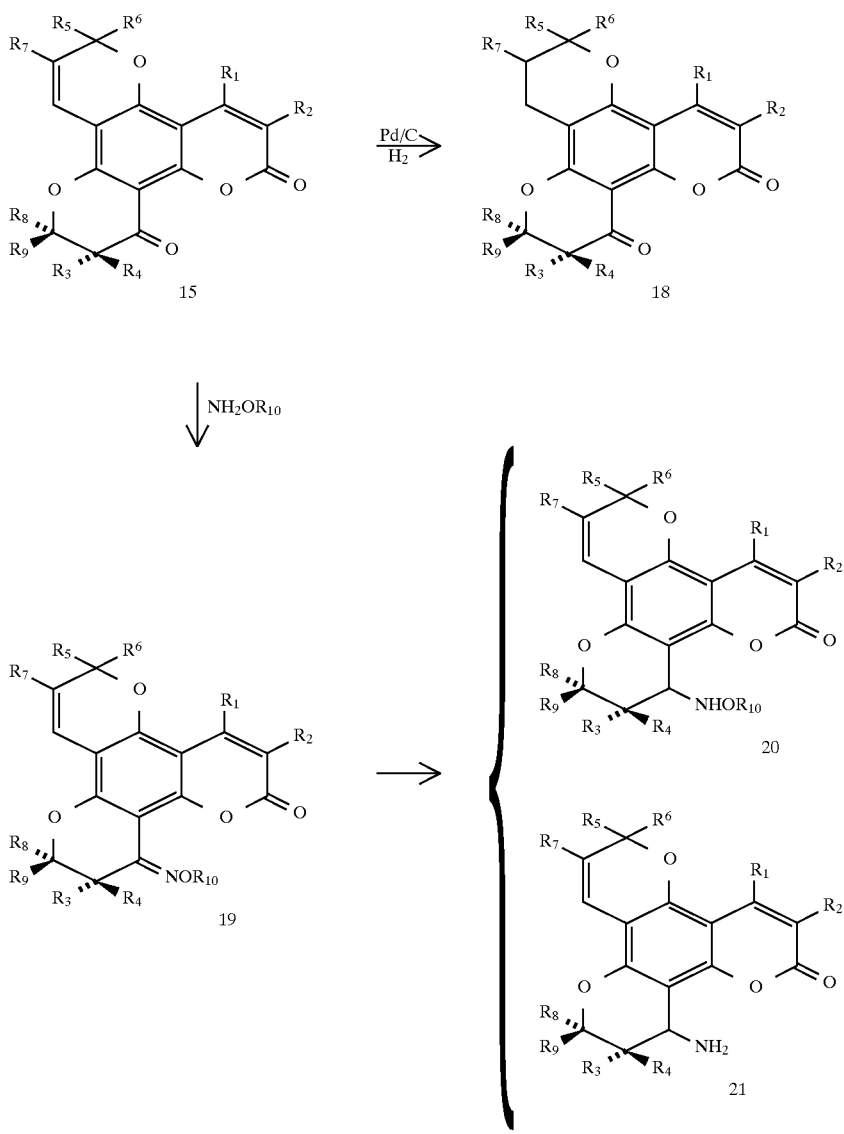
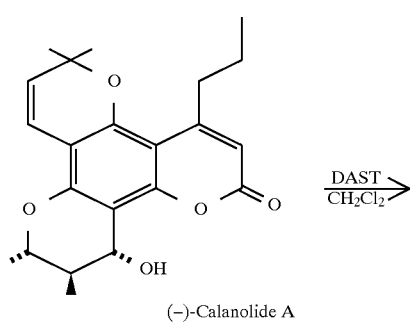
(−)-Calanolide A
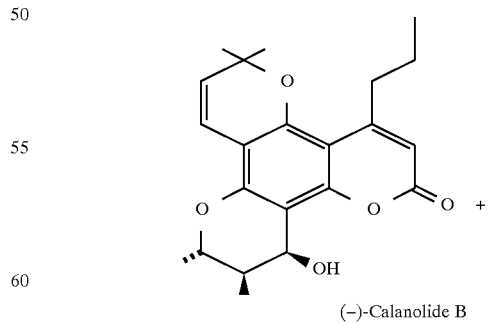
(−)-Calanolide B

Scheme VII -continued

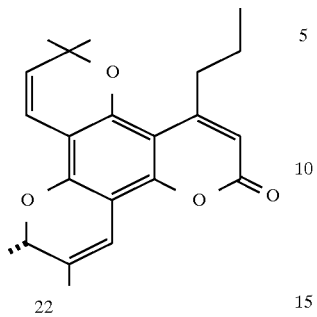

22

SCHEME VIII

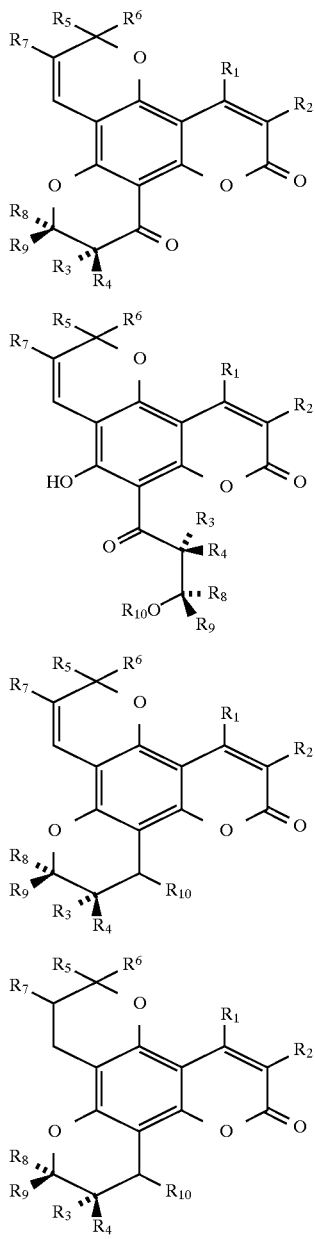

I

II

III

IV

SCHEME VIII -continued

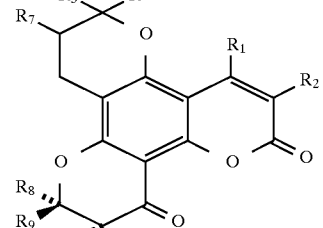

V

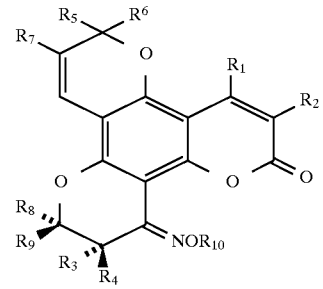

VI

DESCRIPTION OF THE DRAWINGS

FIGS. 1(a) to 1(e) illustrate in vitro MTT assay results, as described in Example 37, using G910-6 HIV viral strain which is AZT-resistant.

FIGS. 4(a) to 4(d) illustrate in vitro MTT assay results, as described in Example 37, using IIIB cultivated HIV viral strain.

FIG. 6 is an HPLC chromatogram of (a) (±)-calanolide A on normal phase column; (b) (±)-calanolide A on a chiral HPLC column; (c) (+)-calanolide A on a chiral HPLC column and (d) (−)-calanolide A on a chiral HPLC column. The HPLC conditions are described in Example 13.

DETAILED DESCRIPTION OF THE INVENTION

Figure 1A:
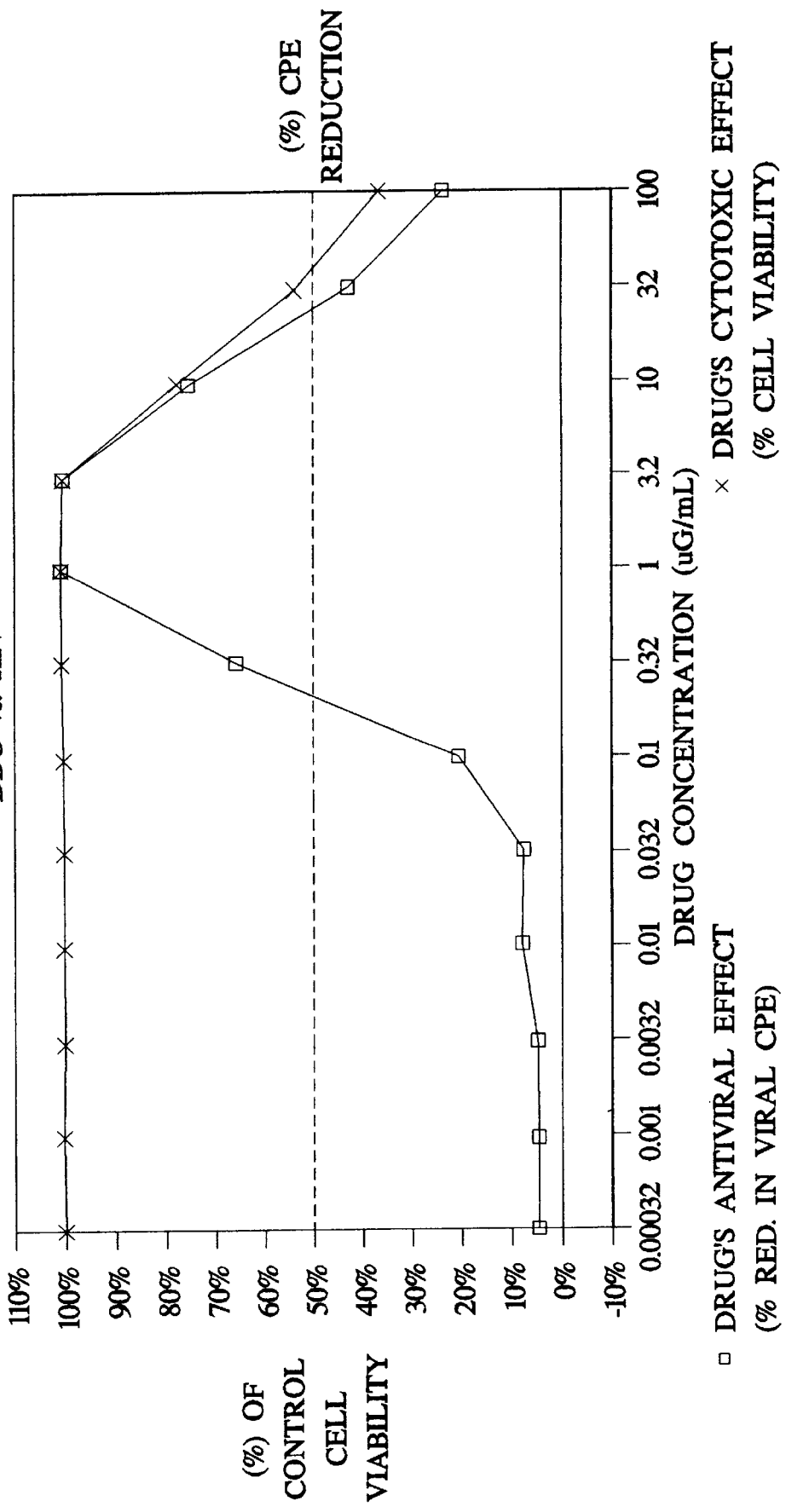

All patents, patent applications, and literature references cited herein are incorporated by reference in their entirety.

The present invention relates to methods for the preparation of optically pure (+)-calanolide A and calanolide A analogues and homologues thereof and compounds produced by the inventive method.

In one embodiment of the invention, a process is provided for preparing (+)-calanolide A from chromene 4, a key intermediate, as shown in Schemes I and III. According to the method of the present invention, chromene 4 may be prepared from 5,7-dihydroxy-4-propylcoumarin, 2, is shown in Scheme I. According to this synthetic scheme, 5,7-dihydroxy-4-propylcoumarin, 2,[5] was prepared quantitatively from ethyl butyrylacetate and phloroglucinol under Pechmann conditions.[6]

In conducting this reaction, a volume of a concentrated acid is added in a dropwise manner to a stirring mixture of ethyl butyrylacetate and phloroglucinol with a molar ratio ranging between about 3:1 and about 1:3, with a preferable range being about 0.9:1.0. The dropwise addition of an acid was conducted at a rate such that the temperature of the reaction mixture is maintained at a temperature ranging between about 0° C. and about 120° C., preferably about 90° C.

Suitable, but not limiting, examples of concentrated acid include sulfuric acid, trifluoroacetic acid, and methanesulfonic acid. In practicing this invention, concentrated sulfuric acid is particularly preferred. As the product yield and purity appear to be dependent on the amount of concentrated sulfuric acid used, it is preferred that the amount of concentrated sulfuric acid ranges between about 0.5 and 10 mole, most preferably ranging between about 2 and about 3.5 mole, per mole of ethyl butyrylacetate.

The reaction mixture is then heated to a temperature ranging between about 40° C. and about 150° C., preferably about 90° C., until the reaction reaches completion as determined by TLC analysis. The reaction mixture is then poured onto ice and the precipitated product is collected by filtration and dissolved in an organic solvent. Suitable, but non-limiting, examples of organic solvents include ethyl acetate, chloroform, and tetrahydrofuran. A preferred solvent is ethyl acetate. The resulting solution is then washed with brine and dried over a suitable drying agent, e.g., sodium sulfate. The yields of this reaction are generally quantitative.

Thereafter, 5,7-dihydroxy-8-propionyl-4-propylcoumarin, 3, was prepared by selectively acylating the 8-position of 5,7-dihydroxy-4-propylcoumarin, 2, with propionyl chloride in the presence of a Lewis acid catalyst (Friedal-Crafts acylation). In conducting this reaction, a solution of propionyl chloride in a suitable solvent, e.g., carbon disulfide, was added in a dropwise manner to a vigorously stirred solution of 5,7-dihydroxy-4-propylcoumarin, 2, a Lewis acid and an organic solvent cooled in an ice bath. Dropwise addition of propionyl chloride is conducted such that the temperature of the reaction mixture is maintained at a temperature ranging between 0° C. and about 30° C., preferably between about 8° C. and 10° C.

In practicing the invention, the amount of propionyl chloride used generally ranges between about 0.5 and about 6 moles, preferably ranging between about 1 and about 2 moles, per mole of 5,7-dihydroxy-4-propylcoumarin, 2.

Non-limiting examples of Lewis acid catalysts useful in the acylation reaction include $AlCl_3$, $BF_3$, $SnCl_4$, $ZnCl_2$, $POCl_3$ and $TiCl_4$. A preferred Lewis acid catalyst is $AlCl_3$. The amount of Lewis acid catalyst relative to 5,7-dihydroxy-4-propylcoumarin, 2, ranges between about 0.5 and about 12 moles, preferably ranging between about 2 and about 5 moles, per mole of 5,7-dihydroxy-4-propylcoumarin, 2.

Non-limiting examples of organic solvent for use in preparing the 5,7-dihydroxy-4-propylcoumarin, 2, solution include nitrobenzene, nitromethane, chlorobenzene, or toluene and mixtures thereof. A preferred organic solvent for use in this invention is nitrobenzene.

Upon completion of the addition of propionyl chloride, the vigorously stirred reaction mixture is maintained at a temperature ranging between about 0° C. and about 120° C., preferably ranging between about 25° C. and 80° C., until the reaction reaches completion as monitored by conventional means such as TLC analysis. The reaction mixture is then poured onto ice and extracted several times with a suitable solvent such as ethyl acetate, chloroform, methylene chloride, tetrahydrofuran, or a mixture of chloroform/methanol. A preferred solvent for this extraction is ethyl acetate. The extracts are then dried over a suitable drying agent, e.g., sodium sulfate, and the product may be purified by conventional means such as silica gel column chromatography.

On small scale (<1 gram), the yield of 5,7-dihydroxy-8-propionyl-4-propylcoumarin 3, produced by the above described reaction is generally quantitative. However, on larger scale (>1 gram), the reaction was very difficult to control and did not exclusively afford the desired product as the desired 8-position acylated product 3 was accompanied by the formation of undesired 6-position acylated product and 6,8-bis-acylated product. Thus, an alternative and preferred route for preparing 5,7-dihydroxy-8-propionyl-4-propylcoumarin 3 in large scale quantities was devised.

Preparation of 8-acylated coumarin 3 on a 5 gram scale as a single product (45% yield) has been achieved by adding a mixture of propionic anhydride, a Lewis acid, e.g., $AlCl_3$, and suitable solvent, e.g., 1,2-dichloroethane, into a vigorously stirring pre-heated mixture of coumarin, a Lewis acid, e.g., $AlCl_3$, and suitable solvent, e.g., 1,2-dichloroethane, at a temperature ranging between about 40° and about 160° C., preferably ranging between about 70° and about 75° C. Dropwise addition of the propionic anhydride solution is conducted at a rate such that the temperature of the reaction mixture is maintained within the desired temperature range.

The amount of propionic anhydride used in the reaction generally ranges between about 0.5 and about 10 moles, preferably ranging between about 1 and about 2 moles, per mole of 5,7-dihydroxy-4-propylcoumarin 2.

Non-limiting examples of Lewis acid catalysts useful in the acylation reaction include $AlCl_3$, $BF_3$, $POCl_3$, $SnCl_4$, $ZnCl_2$ and $TiCl_4$. A preferred Lewis acid catalyst is $AlCl_3$. The amount of Lewis acid catalyst relative to 5,7-dihydroxy-4-propylcoumarin, 2, ranges between about 0.5 and about 12 moles, preferably ranging between about 2 and about 4 moles, per mole of 5,7-dihydroxy-4-propylcoumarin, 2.

Suitable but nonlimiting examples of solvents for use in the invention include diglyme, nitromethane, 1,1,2,2-tetrachloroethane, and 1,2-dichloroethane (preferred). Upon completion of the addition of propionyl anhydride, the vigorously stirred reaction mixture is maintained at a temperature ranging between about 40° C. and about 160° C., preferably ranging between about 70° C. and 75° C., until the reaction reaches completion as monitored by conventional means such as TLC analysis. The workup procedure is the same as described above.

The product was purified without the use of column chromatography to afford the desired product 3. This procedure has been scaled-up to 1.7 kg of coumarin (for details see experimental section) and the yield for 8-acylated coumarin 3 was 29% after recrystallization. The yield for 8-acylated coumarin 3 may be further improved by changing the purification processing. For example, the crude product may be recrystallized from solvent(s) other than dioxane, or a simple washing with an appropriate solvent may lead to product pure enough for the next reaction step.

Thereafter, chromene 4 was prepared by introducing the chromene ring into 5,7-dihydroxy-8-propionyl-4- propylcoumarin, 3, using 4,4-dimethoxy-2-methylbutan-2-ol. According to the method of the present invention, a solution of 5,7-dihydroxy-8-propionyl-4-propylcoumarin, 3, and 4,4-dimethoxy-2-methylbutan-2-ol in a suitable organic solvent in the presence of a base was reacted at a temperature ranging between about 40° C. and about 180° C., preferably ranging between about 100° C. and about 120° C., until the reaction reached completion as determined by conventional means such as TLC analysis. Water and methanol formed during the reaction were removed azeotropically via a Dean-Stark trap.

In practicing this invention, the amount of 4,4-dimethoxy-2-methylbutan-2-ol employed in the reaction generally ranges between about 0.5 and about 8 moles, preferably ranging between about 2 and about 4 moles, per mole of 5,7-dihydroxy-8-propionyl-4-propylcoumarin 3.

Suitable, but not limiting examples of organic solvents include pyridine, triethylamine, N,N-dimethylformamide (DMF), toluene, tetrahydrofuran (THF) or 1,2-dichloroethane. Suitable, but non-limiting examples of the bases include pyridine, 4-dimethylaminopyridine, triethylamine, N,N-diethylaniline, 1,5-diazabicyclo-[4,3,0]-non-5-ene (DBN), 1,8-diazabicyclo-[5,4,0]undec-7-ene (DBU), sodium carbonate and sodium bicarbonate. Pyridine was used as both base and solvent in this invention on a small scale; for scale-up, however, pyridine was used as a base and toluene was used as a solvent.

Upon completion of the reaction, the solvent is removed under reduced pressure and the reaction product is dissolved in a suitable solvent, e.g., ethyl acetate. The solution is then washed sequentially with water and brine and dried over a suitable drying agent, e.g., sodium sulfate. Thereafter, the crude chromene 4 product can be purified by conventional means such as silica gel column chromatography using 25% ethyl acetate/hexane as the elution solvent. The yields of chromene 4 generally fall with the range of about 60% and about 85%, usually resulting in about 78% yield. Chromene 4 was then used to prepare chromanone 7.

A number of alternative routes were devised for preparing chromanone 7 from chromene 4 in large scale quantities. These routes were described in U.S. patent application Ser. No. 08/510,213, filed Aug. 2, 1995, the disclosure which is incorporated herein in its entirety. For instance, U.S. patent application Ser. No. 08/510,213 describes a one-step reaction process (paraldehyde one-step reaction), shown in Scheme II, and a two-step reaction process (LDA/sulfuric acid process or LDA/Mitsunobu process) for preparing chromanone 7 from chromene 4. Examples of these reactions are provided in the Examples below. In this invention, a new route for preparing chromanone 7 from chromene 4 was devised, shown in Scheme III, which introduces a chiral resolution step between the two step LDA/Mitsunobu process described in the 08/510,213 application and illustrated below. One of the benefits for including the enzyme acylation/resolution step at this stage of the process is that it provides a more practical and economical means for producing large scale amounts of chromanone (+)-7, which would lead to formation of (+)-calanolide A after reduction without the subsequent need for chiral HPLC resolution of the racemic calanolide A.

According to Scheme III, (+)-chromanone 7 was prepared by a chlorotitanium-mediated aldol condensation reaction of chromene 4 with acetaldehyde which led to formation of aldol products (±)-8a and (±)-8b in a ratio of 95:5, respectively. In conducting the aldol condensation reaction, a solution of LDA was added dropwise to a solution of chromene 4 dissolved in a solvent at a temperature ranging between about −78° C. and about 0° C., preferably about −30° C. and about −78° C. Thereafter, a solution of titanium tetrachloride was added dropwise to the stirring reaction mixture. The resulting solution was then warmed to a temperature ranging between about −78° C. and about 40° C., preferably about −40° C., and allowed to stir for about 45 minutes to allow for transmetallation. Thereafter, the solution was recooled to −78° C.

The amount of LDA added per mole of chromene 4 ranged between about 1 and about 4 moles, preferably ranging between about 2 and about 3 per mole of chromene 4. Dropwise addition LDA is conducted such that the reaction temperature is maintained within the desired range.

The amount of titanium tetrachloride ranges between about 0.5 and about 10 moles, preferably ranging between about 2 and about 4 moles per mole of chromene 4.

Suitable, but not limiting examples of solvent include methylene chloride, THF, diethyl ether, dioxane, etc.

Acetaldehyde was then added dropwise to the reaction mixture in amounts ranging between about 1 and about 12 moles, preferably ranging between about 4 and about 6 moles per mole of chromene 4. Dropwise addition of acetaldehyde is conducted such that the reaction temperature is maintained within the aforementioned range. The reaction was monitored by conventional means, e.g., TLC analysis, until it reached completion.

The aldol reaction of chromene 4 with acetaldehyde may be carried out under conditions which employs bases other than LDA. For example, metal hydroxides such as NaOH, KOH and Ca(OH)$_2$, metal alkoxides such as MeONa, EtONa and t-BuOK, and amines such as pyrrolidine, piperidine, diisopropylethylamine, 1,5-diazabicyclo[4,3,0] non-5-ene (DBN), 1,8-diazabicyclo[5,4,0]undec-7-ene (DBU), NaNH$_2$ and LiHMDS as well as hydrides such as NaH and KH can all be employed for the aldol reactions.[10] Also, aldol reactions can be mediated by metal complexes of Al, B, Mg, Sn, Zn, Zr and other Ti compounds such as (i-PrO)$_3$TiCl, (i-PrO)$_4$Ti, PhBCl$_2$, (n-Bu)$_2$BCl, BF$_3$, (n-Bu)$_3$SnCl, SnCl$_4$, ZnCl$_2$, MgBr$_2$, Et$_2$AlCl with or without chiral auxiliaries such as 1,1'-binaphthol, norephedrinesulfonate, camphanediol, diacetone glucose and dialkyl tartrate.[11-13]

Thereafter, the reaction mixture was quenched at −30° C. to −10° C. with saturated aqueous ammonium chloride solution and extracted with a suitable solvent, e.g., ethyl acetate. The pooled extracts were washed with brine and dried over a suitable drying agent, e.g., sodium sulfate. The yields of aldol product generally range between about 40% and about 80%, usually about 70%.

It should be noted that the aldol reaction of chromene 4 results in a product having two asymmetric centers which in turn would result in a diastereomeric mixture of two sets of enantiomers (four optically active forms). The mixture may be separated by conventional means to produce racemic syn aldol product (±)-8a and racemic anti aldol product (±)-8b which may be resolved into optically active forms. Conventional resolution methods may be used such as chromatography or fractional crystallization of suitable diastereoisomeric derivatives such as salts or esters with optically active acids (e.g., camphor-10-sulfonic acid, camphoric acid, methoxyacetic acid, or dibenzoyltartaric acid) or enzymatically catalyzed acylation or hydrolysis of the racemic esters. The resultant or synthetic enantiomer may then be transformed to enantioselective synthesis of (+)-calanolide A and its congeners.

In one method, the racemic aldol product may be resolved by high performance liquid chromatography (HPLC) with organic solvent system as a mobile phase. HPLC is performed on a column packed with chiral packing material. Suitable, but not limiting, examples of chiral packing material include amylose carbamate, D-phenylglycine, L-phenylglycine, D-leucine, L-leucine, D-naphthylalanine, L-naphthylalanine, or L-naphthylleucine. These materials may be bounded, either ionically or covalently, to silica sphere which particle sizes ranging between about 5 $\mu$m and about 20 $\mu$m. Suitable, but non-limiting, mobile phase includes hexane, heptane, cyclohexane, ethyl acetate, methanol, ethanol, or isopropanol and mixtures thereof. The mobile phase may be employed in isocratic, step gradient or continuous gradient systems at flow rates generally ranging between about 0.5 mL/min. and about 50 mL/min.

In practicing this invention, the racemic product, i.e., syn aldol product [(±)-8a], is resolved preferably by enzyme-catalyzed acylation. Enzymatic resolution may employ enzymes such as lipase CC (*Candida cylindracea*), lipase AK (*Candida cylindracea*), lipase AY (*Candida cylindracea*), lipase PS (Pseudomonas Species), lipase AP (*Aspergillus niger*), lipase N (*Rhizopus nieveuis*), lipase FAP (*Rhizopus nieveus*), lipase PP (Porcine Pancrease), pig (porcine) liver esterase (PLE), pig liver acetone powder (PLAP), or subtilisin. Immobilized forms of the enzyme on cellite, molecular sieves, or ion exchange resin are also contemplated for use in this method. The amount of enzyme used in the reaction depends on the rate of chemical conversion desired and the activity of the enzyme. The preferred enzyme for use in the enzyme-catalyzed acylation reaction is lipase.

The enzymatic acylation reaction is carried out in the presence of an acylating agent. Suitable, but not limiting, examples of acylating agents include vinyl acetate, vinyl propionate, vinyl butyrate, vinyl stearate, acetic anhydride, propionic anhydride, phthalic anhydride, acetic acid, propionic acid, hexanoic acid or octanoic acid. The enzymatic reaction employs at least one mole of acylating agent per mole of aldol product. Acylating agent can be used as a solvent in the acylation reaction or in solution with another solvent such as hexanes, chloroform, benzene, tert-butylmethyl ether, and THF. The preferred solvent and acylating agent for use in the enzyme-catalyzed acylation are tert-butylmethyl ether and vinyl acetate, respectively.

Suitable, but not limiting examples of solvents for use in the enzymatic hydrolysis reaction include water, suitable aqueous buffers such as sodium phosphate buffers, or alcohols such as methanol or ethanol.

One skilled in the art will appreciate that racemic esters of aldol products can be made by conventional esterification means and selectively hydrolyzed by enzymes so as to produce, in high enantiomeric excess, optically active aldol product, i.e., (+)-8, in free or esterified form.

The purified (+)-8a was subjected to a neutral Mitsunobu reaction, selectively leading to (+)-trans-chromanone[(+)-7]. In performing this reaction, diethyl azodicarboxylate (DEAD) was added dropwise to a solution containing (+)-8a and triphenylphosphine at a temperature ranging between about –10° C. and about 40° C., preferably about ambient temperature. The amount of DEAD used in the reaction generally ranges between about 1 mole and about 10 moles preferably about 1 mole and about 4 moles, per mole of aldol (+)-8a. The amount of triphenylphosphine used in the reaction generally ranged between about 1 mole and about 10 moles, preferably ranging between about 1 mole and about 4 moles, per mole of aldol (+)-8a.

Instead of DEAD, other suitable azo reagents reported in the literature can be employed such as diisopropyl azodicarboxylate (DIAD), dibutyl azodicarboxylate (DBAD), dipiperidinoazodicarboxamide, bis($N^4$-methylpiperazin-1-yl)azodicarboxamide, dimorpholinoazodicarboxamide, N,N,N',N'-tetramethylazodicarboxamide (TMAD)[14]. Also, in addition to triphenylphosphine, other phosphine derivatives such as tri-n-butylphosphine,[14] triethylphosphine, trimethylphosphine and tris(dimethylamino)phosphine may be used.

Thereafter, the reaction was quenched with saturated ammonium chloride upon completion and extracted with a suitable solvent, e.g., ethyl acetate. The pooled organic layers were washed with brine, concentrated in vacuo and the crude chromanone (+)-7 was purified by conventional means as discussed above. The yields of chromanone (+)-7 from the Mitsunobu reaction generally range between about 60% and about 80%, usually about 70%.

Finally, mild borohydride reduction of chromanone (+)-7 in the presence of $CeCl_3(H_2O)_7$ (Luche reduction) produced (+)-calanolide A with the desired stereochemical arrangement. In conducting the reduction reaction, a solution of chromanone (+)-7 was added dropwise into a solution of reducing agent, e.g., sodium borohydride and a metal additive, e.g., $CeCl_3(H_2O)_7$ in ethanol. The rate of addition is such that the reaction mixture temperature is maintained within a range of between about –40° C. and about 60° C., preferably ranging between about –10° C. and about –30° C. Thereafter, the reaction mixture was stirred at a temperature ranging between about –40° C. and about 60° C.

In general, the amount of metal additive, e.g., $CeCl_3$ $(H_2O)_7$ present in the reaction mixture ranged between about 0.1 and about 2 moles, preferably ranging between bout 0.5 and about 1 mole, per mole of sodium borohydride. In addition, the amount of reducing agent, e.g., sodium borohydride employed in the reaction generally ranged between about 0.1 and about 12 moles, preferably ranging between about 2 and about 4 moles, per mole of chromanone (+)-7. Suitable, but non-limiting, examples of reducing agents include $NaBH_4$ $LiAlH_4$, (i-Bu)$_2$AlH, (n-Bu)$_3$SnH, 9-BBN, $Zn(BH_4)_2$, $BH_3$, DIP-chloride, selectrides and enzymes such as baker yeast. Suitable, but non-limiting, examples of metal additives include $CeCl_3$, $ZnCl_2$, $AlCl_3$, $TiCl_4$, $SnCl_3$, and $LnCl_3$ and their mixture with triphenylphosphine oxide. In practicing this invention, sodium borohydride as reducing agent and $CeCl_3(H_2O)_7$ as metal additive are preferred.

Thereafter, the reduction mixture was diluted with water and extracted with a suitable solvent, e.g., ethyl acetate. The extract was dried over a suitable drying agent, e.g., sodium sulfate, and concentrated. The resulting residue was then purified by conventional means such as silica gel chromatography, using ethyl acetate/hexane solvent mixtures. Luche reduction on (+)-7 led to formation of (+)-calanolide A [(+)-1] which contained 10% of (+)-calanolide B. (+)-Calanolide A [(+)-1] was further separated from (+)-calanolide B by preparative normal phase HPLC and was identical with an authentic sample.

Thus, (+)-calanolide A, 1, was successfully prepared with the desired stereochemical arrangement by treatment of the key intermediate chromene 4 with chlorotitanium catalyzed aldol reaction to produce (±)-8a, enzyme resolution of the racemate to produce (+)-8a, and neutral Mitsunobu reaction of (+)-8a to produce chromanone (+)-7, followed by Luche reduction via chromanone (+)-7 (see Scheme III).

Enzyme resolution of trans-(±)-8b racemate with vinyl acetate and lipase allowed for the separation of (+)-8b, which, following treatment under neutral Mitsunobu reaction with triphenylphosphine and DEAD and subsequent Luche reduction, would result in calanolide C (Scheme IV).

In another embodiment of the invention, analogues of calanolide A are provided by extension of the aforementioned synthetic sequence for (+)-calanolide A. Pechmann reaction of phloroglucinol with substituted β-ketoesters yields substituted 5,7-dihydroxycoumarin 11 as shown in Scheme V. The conditions and reagents used in the Pechmann reaction are described above.

Suitable, but non-limiting, β-ketoesters include those of formula i:

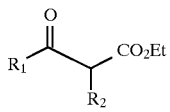

wherein $R_1$ is H, halogen, hydroxyl, amino, $C_{1-6}$ alkyl, aryl-$C_{1-6}$ alkyl, mono- or poly-fluorinated $C_{1-6}$ alkyl, hydroxy-$C_{1-6}$ alkyl, $C_{1-6}$ alkoxy, amino-$C_{1-8}$ alkyl, $C_{1-6}$ alkylamino, di($C_{1-6}$ alkyl)amino, $C_{1-8}$ alkylamino-$C_{1-8}$ alkyl, di($C_{1-6}$ alkyl) amino-$C_{1-8}$ alkyl, cyclohexyl, aryl, or heterocycle, wherein aryl or heterocycle may each be unsubstituted or substituted with one or more of the following: $C_{1-6}$ alkyl, $C_{1-6}$ alkoxy, hydroxy-$C_{1-4}$ alkyl, hydroxyl, amino, $C_{1-6}$ alkylamino, di($C_{1-6}$ alkyl)amino, amino-$C_{1-8}$ alkyl, $C_{1-8}$ alkylamino-$C_{1-8}$ alkyl, di($C_{1-6}$ alkyl-amino-$C_{1-8}$ alkyl, nitro, azido or halogene; and $R_2$ is H, halogen, hydroxyl, $C_{1-6}$ alkyl, aryl-$C_{1-6}$ alkyl, mono- or poly-fluorinated $C_{1-6}$ alkyl, aryl or heterocycle.

Friedel-Crafts acylation of substituted 5,7-dihydroxycoumarin 11 leads to formation of 8-acylated 5,7-dihydroxycoumarin 12. The conditions and reagents used in the Friedel-Crafts acylation reaction are described above.

Non-limiting examples of carboxylic acid anhydrides and halides include formula ii carboxylic acid anhydrides and halides:

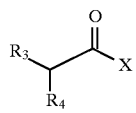

wherein X is halogen (e.g. chloro) or OCOCHR$_3$R$_4$ wherein $R_3$ and $R_4$ are independently selected from the group consisting of H, halogen, hydroxyl, $C_{1-6}$ alkyl, aryl-$C_{1-6}$ alkyl, mono- or poly-fluorinated $C_{1-6}$ alkyl, hydroxy-$C_{1-6}$ alkyl, amino-$C_{1-8}$ alkyl, $C_{1-8}$ alkylamino-$C_{1-8}$ alkyl, di ($C_{1-6}$ alkyl) amino-$C_{1-8}$ alkyl, cyclohexyl, aryl or heterocycle; and $R_3$ and $R_4$ can be taken together to form a 5–7 membered saturated cycle ring or heterocyclic ring.

Chromenylation of 12 can be achieved by reacting with substituted β-hydroxyaldehyde dimethylacetal, affording chromenocoumarin 13. The conditions and amounts of reagents are described above. Representative examples of substituted β-hydroxyaldehyde dimethylacetals of formula iii comprise:

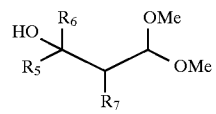

wherein $R_5$ and $R_6$ are independently selected from the group consisting of H, $C_{1-6}$ alkyl, aryl-$C_{1-6}$ alkyl, mono- or poly-fluorinated $C_{1-6}$ alkyl, aryl or heterocycle; $R_5$ and $R_6$ can be taken together to form a 5–7 membered saturated cycle ring or heterocycle ring; and $R_7$ is H, halogen, methyl, ethyl.

Aldol condensation reaction of chromene 13 with carbonyl compounds in the presence of LDA forms the racemic aldol product (±)-14. According to the present invention, a solution of LDA in THF was added dropwise to a solution of chromene 13 in THF at a temperature ranging between about −78° C. and about 0° C., preferably about −30° C. and about −78° C. The amount of LDA added per mole of chromene 13 ranged between about 1 and about 4 moles, preferably ranging between about 2 and about 3 moles per mole of chromene 13. Dropwise addition of LDA is conducted such that the reaction temperature is maintained within the desired range.

A carbonyl compound of formula iv was then added dropwise to the reaction mixture in amounts ranging between about 1 and about 12 moles, preferably ranging between about 4 and about 6 moles per mole of chromene 13. Dropwise addition of carbonyl compound is conducted such that the reaction temperature is maintained within the aforementioned range. The reaction was monitored by conventional means, e.g., TLC analysis, until it reached completion.

Representative examples of formula iv carbonyl compounds comprise:

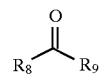

wherein $R_8$ and $R_9$ are independently selected from the group consisting of H, halogen, $C_{1-6}$ alkyl, aryl-$C_{1-6}$ alkyl, mono- or poly-fluorinated $C_{1-6}$ alkyl, hydroxy-$C_{1-6}$ alkyl, amino-$C_{1-8}$ alkyl, $C_{1-8}$ alkylamino-$C_{1-8}$ alkyl, di($C_{1-6}$ alkyl) amino-$C_{1-8}$ alkyl, cyclohexyl, aryl or heterocycle; and $R_8$ and $R_9$ can be taken together to form a 5–7 membered saturated cycle ring or heterocyclic ring.

One skilled in the art will appreciate that the aldol reaction of chromene 13 with carbonyl compounds of formula iv to form 14 can be carried out under conditions which employs bases other than LDA. For example, metal hydroxides such as NaOH, KOH and Ca(OH)$_2$, metal alkoxides such as MeONa, EtONa and t-BuOK, and amines such as pyrrolidine, piperidine, diisopropylethylamine, 1,5-diazabicyclo[4,3,0]non-5-ene (DBN), 1,8-diazabicyclo[5,4,0]undec-7-ene (DBU), NaNH$_2$ and LiHMDS as well as hydrides such as NaH and KH can all be employed for the aldol reactions.[10] Also, aldol reactions can be mediated by metal complexes of Al, B, Mg, Sn, Ti, Zn and Zr compounds such as TiCl$_4$, (i-PrO)$_3$TiCl (i-Pro)$_4$Ti, PhBCl$_2$, (n-Bu)$_2$BCl, BF$_3$, (n-Bu)$_3$SnCl, SnCl$_4$, ZnCl$_2$, MgBr$_2$, Et$_2$AlCl with or without chiral auxiliaries such as 1,1'-binaphthol, norephedrinesulfonate, camphanediol, diacetone glucose and dialkyl tartrate.[11-13]

Thereafter, the reaction mixture was quenched at −30° C. to −10° C. with saturated aqueous ammonium chloride solution and extracted with a suitable solvent, e.g., ethyl acetate. The pooled extracts were washed with brine and dried over a suitable drying agent, e.g., sodium sulfate. The yields of aldol product (±)-14 generally range between about 40% and about 80%, usually about 70%.

Cyclization of (±)-14 under neutral Mitsunobu conditions, by using triphenylphosphine and diethyl azodicarboxylate (DEAD), leads to formation of chromanone analogue (±)-15. Reduction of (±)-15 with sodium borohydride with or without metal additives such as cerium chloride yields the 12-hydroxy analogue (±) -16 (Scheme V). The conditions and amounts of reagents used in the Mitsunobu and borohydride reduction reactions are described above.

Catalytic hydrogenation of both (±)-15 and (±)-16 produces 7,8-dihydro derivatives (±)-17 and (±)-18 (Scheme VI). To a solution of (±)-15 or (±)-16 in ethanol or ethanol/ methylene chloride mixtures in a conventional Parr apparatus under $N_2$, hydrogenation catalyst was added at ambient temperature. The mixture was shaken under hydrogen for a time sufficient to complete the hydrogenation reaction. The solution was then gravity filtered to remove catalyst and solvent was evaporated.

Suitable, but non-limiting, hydrogenation catalysts for use in the invention include Pd/C, $PtO_2$ and Rh/C, Raney-Ni. In practicing the invention, 10% palladium/carbon is preferred. The amount of catalyst employed generally ranges between about 0.01 and about 0.5 mole, preferably ranging between about 0.05 and about 0.1 mole per mole of (±)-15 or (±)-16.

In yet another embodiment of the invention, intermediate chromanones (±)-7, (+)-7, (+)-7a and (±)-15 can be used to prepare oxime, hydroxyamino, alkoxyamino or amino calanolide derivatives. Treatment of the said chromanones with hydroxylamine or alkoxyamine affords oxime derivatives (±)-19 (Scheme VI).

Representative amines for preparing oxime derivatives comprise $NH_2OR_{10}$ wherein $R_{10}$ is H, $C_{1-8}$ alkyl, phenyl, benzyl, acyl $P(O)(OH)_2$, $S(O)(OH)_2$, $CO(C_{1-10}$ alkyl)$CO_2H$, $(C_{1-8}$ alkyl)$CO_2H$, $CO(C_{1-10}$ alkyl)$NR_{12}$ $R_{13}$, $(C_{1-8}$ alkyl)$NR_{12}R_{13}$; wherein $R_{12}$ and $R_{13}$ are independently selected from the group consisting of H, $C_{1-6}$ alkyl; and $R_{12}$ and $R_{13}$ can be taken together to form a 5–7 membered saturated heterocyclic ring containing said nitrogen. Examples of useful alkoxyamines include methoxyamine and benzyloxyamine.

The oxime derivatives may be prepared by refluxing a methanolic solution of the chromanone with hydroxyl amine or alkoxyamine in the presence of a metal carbonate such as potassium carbonate or pyridine until the reaction reaches completion. The amount of amine generally ranges between about 1 and about 20 moles, preferably between about 3 and about 6 moles, per mole of chromanone.

Upon completion of the reaction, filtration of the solution to remove solids and removal of solvent resulted in an oil which was purified via silica gel chromatography. The yields of oximes generally range between about 30% and about 80%, usually about 50%.

If desired, oxime derivatives (±)-19 may be reduced under different conditions[9] to yield hydroxyamino or amino compounds (20 and 21).

Thus, optically active forms of 14–21 (Scheme V and VI) would be obtained by employing enzymatic acylation, as described above, in the procedure outlined in Scheme III for (+)-calanolide A [(+)-1]. Enzyme-catalyzed acylation of the racemic aldol product (±)-14 would selectively acylate one enantiomer [i.e. (−)-14] and leave the other enantiomer [i.e. (+)-14] unreacted, which would be easily separated by conventional methods such as silica gel column chromatography. The acylated enantiomer [i.e. (−)-14] may be hydrolyzed to form the pure enantiomer [i.e. (−)-14]. The optically pure enantiomers thus obtained [(+)-14 and (−)-14] will be cyclized to (+)-15 and (−)-15, respectively, by the Mitsunobu reaction as described above. Subsequent reduction of (+)-15 and (−)-15 would lead to formation of (+)-16 and (−)-16, respectively. Hydrogenation of optically active forms of 15 and 16 would provide pure enantiomers of 17 and 18 [(+)-and (−)-17; (+)-and (−)-18], respectively. Treatment of pure enantiomers of 15 with hydroxylamine or alkoxyamine, as described above, should afford enantiomerically pure oxime 19 [(+)-and (−)-19]. Reduction of (+)-19 and (−)-19 would lead to formation of enantiomerically pure 20 and 21 [(+)- and (−)-20; (+)-and (−)-21].

The 12-hydroxyl group in compound 1, 16, and 17 as well as their optically active forms can be epimerized under a variety of conditions including acidic conditions, neutral Mitsunobu conditions[7a-c], or with DAST.[7d] An example showing conversion of (−)-calanolide A [(−)-1] into (−)-calanolide B using DAST[7d] is depicted in scheme VII.

Thus, the process of the present invention may be extended to prepare a wide variety of calanolide analogues such as Formulas I–VI shown in Scheme VIII wherein for Formulas I–V, $R_1$ is H, halogen, hydroxyl, amino, $C_{1-6}$ alkyl, aryl-$C_{1-6}$ alkyl, mono- or poly-fluorinated $C_{1-6}$ alkyl, hydroxy-$C_{1-6}$ alkyl, $C_{1-6}$ alkoxy, amino-$C_{1-8}$ alkyl, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl, cyclohexyl, aryl or heterocycle, wherein aryl or heterocycle may each be unsubstituted or substituted with one or more of the following: $C_{1-6}$ alkyl, $C_{1-6}$ alkoxy, hydroxy-$C_{1-4}$ alkyl, hydroxyl, amino, $C_{1-6}$ alkylamino, di($C_{1-6}$ alkyl)amino, amino-$C_{1-8}$ alkyl, $C_{1-8}$ alkylamino-$C_{1-8}$ alkyl, di($C_{1-6}$ alkyl)amino-$C_{1-8}$ alkyl, nitro, azido or halogen;

$R_2$ is H, halogen, hydroxyl, $C_{1-6}$ alkyl, aryl-$C_{1-6}$ alkyl, mono- or poly-fluorinated $C_{1-6}$ alkyl, aryl or heterocycle;

$R_3$ and $R_4$ are independently selected from the group consisting of H, halogen, hydroxyl, amino, $C_{1-6}$ alkyl, aryl-$C_{1-6}$ alkyl, mono- or poly-fluorinated $C_{1-6}$ alkyl, hydroxy-$C_{1-6}$ alkyl, amino-$C_{1-8}$ alkyl, $C_{1-8}$ alkylamino-$C_{1-8}$ alkyl, di($C_{1-6}$ alkyl)amino-$C_{1-8}$ alkyl, cyclohexyl, aryl or heterocycle; and $R_3$ and $R_4$ can be taken together to form a 5–7 membered saturated cycle ring or heterocyclic ring;

$R_5$ and $R_6$ are independently selected from the group consisting of H, $C_{1-6}$ alkyl, aryl-$C_{1-6}$ alkyl, mono- or poly-fluorinated $C_{1-6}$ alkyl, aryl or heterocycle; and $R_5$ and $R_6$ can be taken together to form a 5–7 membered saturated cycle ring or heterocyclic ring;

$R_7$ is H, halogen, methyl, or ethyl;

$R_8$ and $R_9$ are independently selected from the group consisting of H, halogen, $C_{1-6}$ alkyl, aryl-$C_{1-6}$ alkyl, mono- or poly-fluorinated $C_{1-6}$ alkyl, amino-$C_{1-8}$ alkyl, $C_{1-8}$ alkylamino-$C_{1-8}$ alkyl,di ($C_{1-6}$ alkyl)amino-$C_{1-8}$ alkyl, cyclohexyl, aryl or heterocycle; and $R_8$ and $R_9$ and be taken together to form a 5–7 membered saturated cycle ring or heterocyclic ring.

For Formula II compounds wherein $R_1$, $R_2$, $R_3$, $R_4$, $R_5$, $R_6$, $R_7$, $R_8$, and $R_9$ are the same as defined above, $R_{10}$ is H, acyl, $P(O)(OH)_2$, $S(O)(OH)_2$, $CO(C_{1-10}$ alkyl)$CO_2H$, $(C_{1-8}$ alkyl)$CO_2H$, $CO(C_{1-10}$ alkyl)$NR_{11}$ $R_{12}$, $(C_{1-8}$ alkyl) $NR_{11}R_{12}$; wherein $R_{11}$ and $R_{12}$ are independently selected from the group consisting of H, $C_{1-6}$ alkyl; and $R_{11}$ and $R_{12}$ can be taken together to form a 5–7 membered saturated heterocyclic ring containing said nitrogen.

For Formulae III and IV wherein $R_1$, $R_2$, $R_3$, $R_4$, $R_5$, $R_6$, $R_7$, $R_8$, and $R_9$ are the same as defined above, $R_{10}$ is halogen, $OR_{11}$, $NHOR_{11}$, $NHOR_{12}$, $NR_{11}R_{12}$, $NR_{12}$ $R_{13}$; wherein $R_{11}$ is H, acyl, $P(O)(OH)_2$, $S(O)(OH)_2$, $CO(C_{1-10}$ alkyl)$CO_2H$, $(C_{1-8}$ alkyl)$CO_2H$, $CO(C_{1-10}$ alkyl)$NR_{12}$ $R_{13}$, $(C_{1-8}$ alkyl) $NR_{12}R_{13}$; $R_{12}$ and $R_{13}$ are independently selected from the group consisting of H, $C_{1-6}$ alkyl; and $R_{12}$ and $R_{13}$ can be taken together to form a 5–7 membered saturated heterocyclic ring containing said nitrogen.

For Formula VI compounds, wherein $R_1$, $R_2$, $R_3$, $R_4$, $R_5$, $R_6$, $R_7$, $R_8$, and $R_9$ are the same as defined above, $R_{10}$ is H, $C_{1-6}$ alkyl, aryl or aryl $C_{1-6}$alkyl.

In another embodiment of the invention, a method for converting (−)-calanolide A into (−)-calanolide B is provided. It has been discovered that (−)-calanolide A may be converted readily to (−)-calanolide B using diethylamidosulfur trifluoride (DAST) or the Mitsunobi reaction, e.g., diethyl azodicarboxylate and triphenylphosphine, under the conditions and ranges described above.

The amount of DAST employed in the inversion reaction generally ranges between about 0.5 and about 5.0 moles, preferably ranging between about 1 and about 2.0 moles, per mole of (–)-calanolide A. Suitable, but non-limiting, reaction solvents for use in the invention include methylene chloride, THF, diethyl ether, or chloroform. In practicing the invention, the preferred solvent is methylene chloride. The reaction may be conducted at a temperature ranging between about –78° C. and about 50° C., preferably about –78° C., until the reaction is complete as determined by usual methods such as thin layer chromatography.

In yet another embodiment of the invention, a method for treating or preventing viral infections in mammals using calanolide A analogues is presented. Examples of mammals include humans, primates, bovines, ovines, porcines, felines, canines, etc. Examples of viruses may include, but not be limited to, HIV-1, HIV-2, herpes simplex virus (type 1 and 2) (HSV-1 and 2), varicella zoster virus (VZV), cytomegalovirus (CMV), papilloma virus, HTLV-1, HTLV-2, feline leukemia virus (FLV), avian sarcoma viruses such as rous sarcoma virus (RSV), hepatitis types A–E, equine infections, influenza virus, arboviruses, measles, mumps and rubella viruses. More preferably the compounds of the present invention will be used to treat a human infected with a retrovirus. Preferably the compounds of the present invention will be used to treat a human exposed or infected (i.e., in need of such treatment) with the human immunodeficiency virus, either prophylactically or therapeutically. An advantage of the compounds of the present invention is that they retain the ability to inhibit certain HIV RT mutants which are resistant to other non-nucleoside inhibitors such as TIBO and nevirapine or resistant to nucleoside inhibitors. This is advantageous over the current AIDS drug therapy, where biological resistance often develops to nucleoside analogs used in the inhibition of RT.

Hence the compounds of the present invention are particularly useful in the prevention or treatment of infection by the human immunodeficiency virus and also in the treatment of consequent pathological conditions associated with AIDS. Treating AIDS is defined as including, but not limited to, treating a wide range of states of HIV infection: AIDS, ARC, both symptomatic and asymptomatic, and actual or potential exposure to HIV. For example, the compounds of this invention are useful in treating infection of HIV after suspected exposure to HIV by e.g., blood transfusion, exposure to patient blood during surgery or an accidential needle stick.

Antiviral calanolide A analogues may be formulated as a solution of lyophilized powders for parenteral administration. Powders may be reconstituted by addition of a suitable diluent or other pharmaceutically acceptable carrier prior to use. The liquid formulation is generally a buffered, isotonic, aqeuous solution. Examples of suitable diluents are normal isotonic saline solution, standard 5% dextrose in water or in buffered sodium or ammonium acetate solution. Such formulation is especially suitable for parenteral administration, but may also be used for oral administration. It may be desirable to add excipients such as polyvinylpyrrolidone, gelatin, hydroxy cellulose, acacia, polyethylene glycol, mannitol, sodium choride or sodium citrate.

Alternatively, the compounds of the present invention may be encapsulated, tableted or prepared in an emulsion (oil-in-water or water-in-oil) syrup for oral administration. Pharmaceutically acceptable solids or liquid carriers, which are generally known in the pharmaceutical formulary arts, may be added to enhance or stabilize the composition, or to facilitate preparation of the composition. Solid carriers include starch (corn or potato), lactose, calcium sulfate dihydrate, terra alba, croscarmellose sodium, magnesium stearate or stearic acid, talc, pectin, acacia, agar, gelatin, maltodextrins and microcrystalline cellulose, or collodial silicon dioxide. Liquid carriers include syrup, peanut oil, olive oil, corn oil, sesame oil, saline and water. The carrier may also include a sustained release material such as glyceryl monostearate or glyceryl distearate, alone or with a wax. The amount of solid carrier varies but, preferably, will be between about 10 mg to about 1 g per dosage unit.

The dosage ranges for administration of antiviral calanolide A anlogues or derivatives are those to produce the desired affect whereby symptoms of infection are ameliorated. For example, as used herein, a pharmaceutically effective amount for HIV infection refers to the amount administered so as to maintain an amount which suppresses or inhibits secondary infection by syncytia formation or by circulating virus throughout the period during which HIV infection is evidenced such as by presence of anti-HIV antibodies, presence of culturable virus and presence of p24 antigen in patient sera. The presence of anti-HIV antibodies can be determined through use of standard ELISA or Western blot assays for example, anti-gp120, anti-gp41, anti-tat, anti-p55, anti-p17, antibodies, etc. The dosage will generally vary with age, extent of the infection, the body weight and counterindications, if any, for example, immune tolerance. The dosage will also be determined by the existence of any adverse side effects that may accompany the compounds. It is always desirable, whenever possible, to keep adverse side effects to a minimum.

One skilled in the art can easily determine the appropriate dosage, schedule, and method of administration for the exact formulation of the composition being used in order to achieve the desired effective concentration in the individual patient. However, the dosage can vary from between about 0.001 mg/kg/day to about 50 mg/kg/day, but preferably between about 0.01 to about 1.0 mg/kg/day.

The pharmaceutical composition may contain other pharmaceuticals in conjunction with antiviral calanolide A analogues and derivatives to treat (therapeutically or prophylactically) AIDS. For example, other pharmaceuticals may include, but are not limited to, other antiviral compounds (e.g., AZT, ddC, ddI, D4T, 3TC, acyclovir, gancyclovir, fluorinated nucleosides and nonnucleoside analog compounds such as TIBO derivatives, nevirapine, saquinavir, α-interfon and recombinant CD4), immunostimulants (e.g., various interleukins and cytokines), immunomodulators and antibiotics (e.g., antibacterial, antifungal, anti-pneumocysitis agents). Administration of the inhibitory compounds with other anti-retroviral agents that act against other HIV proteins such as protease, intergrase and TAT will generally inhibit most or all replicative stages of the viral life cycle.

In addition, the compounds of the present invention are useful as tools and/or reagents to study inhibition of retroviral reverse transcriptases. For example, the instant compounds selectively inhibit HIV reverse transcriptase. Hence, the instant compounds are useful as a structure/activity relationship (SAR) tool to study, select and/or design other molecules to inhibit HIV.

The following examples are illustrative and do not serve to limit the scope of the invention as claimed.

EXPERIMENTAL

All chemical reagents and solvents referred to herein are readily available from a number of commercial sources including Aldrich Chemical Co. or Fischer Scientific. NMR spectra were run on a Hitachi 60 MHz R-1200 NMR spectrometer or a Varian VX-300 NMR spectrometer. IR spectra were obtained using a Midac M series FT-IR instrument. Mass spectral data were obtained using a Finnegan MAT 90 mass spectrometer. All melting points are corrected.

EXAMPLE 1

5,7-Dihydroxy-4-propylcoumarin[5] (2)

Concentrated sulfuric acid (200 mL) was added into a mixture of phloroglucinol dihydrate (150 g, 0.926 mol) and ethyl butyrylacetate (161 g, 1.02 mol). The resulting mixture was stirred at 90° C. for two hours whereupon it was poured onto ice. The solid product was collected by filtration, and then dissolved in ethyl acetate. The solution was washed with brine and dried over $Na_2SO_4$. After removal of the solvent in vacuo, the residue was triturated with hexane to provide essentially pure compound 2 (203 g) in quantitative yield, mp 233°–235° C. (Lit.[5] 236°–238° C.). $^1$H-NMR[5] (DMSO-$d_6$) δ 0.95 (3H,t,J=6.9 Hz, $CH_3$); 1.63 (2H, apparent sextet, J=7.0 Hz, $CH_2$); 2.89 (2H,t,J=7.5 Hz, $CH_2$); 5.85 (1H, s, $H_3$); 6.22 (1H, d, J=2.0 Hz, $H_6$); 6.31 (1H, d, J=2.0 Hz, $H_8$); 10.27 (1H, s, OH); 10.58 (1H, s, OH); MS (EI); 220(100, $M^+$); 205 (37.9, M-$CH_3$); 192 (65.8, M-$C_2H_4$); 177 (24.8, M-$C_3H_7$); 164 (60.9, M-$CHCO_2$+1); 163 (59.6 M-$CHCO_2$); IR (KBr): 3210 (vs and broad, OH); 1649 (vs, sh); 1617 (vs, sh); 1554 (s) $cm^{-1}$; Anal. calcd. for $C_{12}H_{24}O_4$: C, 65.45; H, 5.49; Found: C, 65.61; H, 5.44.

EXAMPLE 2

5,7-Dihydroxy-8-propionyl-4-propylcoumarin (3)

A three-neck flask (500 mL) equipped with an efficient methanical stirrer, thermometer and addition funnel was charged with 5,7-dihydroxy-4-propylcoumarin, 2, (25.0 g, 0.113 mol), aluminum chloride (62.1 g; 0.466 mol), and nitrobenzene (150 mL) and the mixture was stirred until a solution was obtained, which was cooled to 0° C. in an ice bath. A solution of propionyl chloride (15.2 g; 0.165 mol) in carbon disulfide (50 mL) was added dropwise at such a rate that the reaction temperature was maintained at 8°–10° C. Addition was completed over a period of 1 hour with vigorous stirring. The reaction was monitored by TLC using a mobile phase of 50% ethyl acetate/hexane. After three hours, an additional portion of propionyl chloride (2.10 g; 0.0227 mol) in carbon disulfide (10 mL) was added. Immediately after the TLC analysis indicated the total consumption of starting material, the reaction mixture was poured onto ice, and allowed to stand overnight. The nitrobenzene was removed by steam distillation, and the remaining solution was extracted several times with ethyl acetate. The extracts were combined and dried over $Na_2SO_4$. The crude product obtained by evaporation in vacuo was purified by chromatography on a silica gel column eluting with 50% ether/hexane to provide the desired propionylated coumarin 3, mp (corr) 244°–246° C. $^1$H-NMR (DMSO-$d_6$) δ 0.96 (3H, t, J=7.3 Hz, $CH_3$); 1.10 (3H, t, J=7.2 Hz, $CH_3$); 1.60 (2H, m, $CH_2$); 2.88 (2H, t, J=7.7 Hz, $CH_2$); 3.04 (2H, q, J=7.2 Hz, $CH_2$); 5.95 (1H, s, $H_3$); 6.31 (1H, s, $H_6$); 11.07 (1H, s, OH); 11.50 (1H, s, OH); MS (EI): 277 (6.6, M+1); 276 (9.0, $M^+$); 247 (100, M-$C_2H_5$); IR (KBr): 3239 (s and broad, OH); 1693 (s, C=O), 1625 and 1593 (s) $cm^{-1}$; Anal. calcd. for $C_{15}H_{16}O_5$: C, 65.21; H, 5.84; Found: c, 64.92; H, 5.83. The isomer assignment was made by analogy to precedent.[15]

EXAMPLE 3

2,2-Dimethyl-5-hydroxy-6-propionyl-10-propyl-2H, 8H-benzo[1,2-b:3,4-b']-dipyran-8-one (4)

A mixture of 3 (2.60 g, 9.42 mmol) and 4,4-dimethoxy-2-methylbutan-2-ol (5.54 g, 37.7 mmol) were dissolved in anhydrous pyridine (6.5 mL). The mixture was refluxed under nitrogen for three days. After removal of the solvent in vacuo, the residue was dissolved in ethyl acetate. The ethyl acetate was washed several times with 1N HCl and brine. It was then dried over $Na_2SO_4$. The crude product obtained by evaporation in vacuo was purified by silica gel column chromatography, eluting with 25% ethyl acetate/ hexane to afford 2.55 g of 4 in 78.6% yield, mp 96°–98° C. $^1$H-NMR (CDCl$_3$) δ 1.05 (3H, t, J=7.3 Hz, $CH_3$); 1.22 (3H, t, J=7.5 Hz, $CH_3$); 1.53 (6H, s, 2 $CH_3$); 1.75 (2H, m, $CH_2$); 2.92 (2H, t, J=7.1 Hz, $CH_2$); 3.35 (2H, q, J=7.1 Hz, $CH_2$); 5.56 (1H, d, J=10.0 Hz, $H_3$); 5.98 (1H, s, $H_9$); 6.72 (1H, d, J=10.0 Hz, $H_4$); MS (EI): 343 (5.7, M+1); 342 (22.5, $M^+$); 327 (100, M-$CH_3$); IR (KBr): 1728 (vs, C=O) $cm^{-1}$; Anal. calcd. for $C_{20}H_{22}O_5$: C, 70.16; H, 6.48; Found: C, 70.45; H, 6.92.

EXAMPLE 4

10,11-Didehydro-12-oxocalanolide A (5)

A mixture of 4 (1.76 g, 5.11 mmol) and sodium acetate (0.419 g, 5.11 mmol) in acetic anhydride (12 mL) were refluxed for 10 hours whereupon the solvent was removed in vacuo. The residue was purified by silica gel column chromatography, eluting first with 25% ethyl acetate/hexane followed by 50% ethyl acetate/hexane to provide 1.16 g (62% yield) of enone 5 (6,6,10,11-tetramethyl-4-propyl-2H, 6H,12H-benzo[1,2-b:3,4-b':5,6-b"]-tripyran-2,12-dione) as a white solid, mp 209°–209.5° C. $^1$H-NMR (CDCl$_3$) δ 1.05 (3H, t, J=6.6 Hz, $CH_3$); 1.56 (6H, s, 2 $CH_3$); 1.73 (2H, m, $CH_2$); 1.98 (3H, s, $CH_3$); 2.38 (3H, s, $CH_3$); 2.91 (2H, t, J=7.5 Hz, $CH_2$); 5.69 (1H, d, J=10.0 Hz, $H_7$); 6.11 (1H, s, $H_3$); 6.71 (1H, d, J=10 Hz, $H_8$); MS (EI): 366 (29.6, $M^+$); 351 (100, M-$CH_3$); 323 (16.5, M-$C_3H_7$); IR (KBr): 1734 (vs, C=O), 1657, 1640, 1610, and 1562 $cm^{-1}$; Anal. calcd. for $C_{22}H_{22}O_5$: 72.12; H, 6.05; Found: C, 72.14; H, 6.15.

EXAMPLE 5

10,11-Didehydrocalanolide A (6)

A mixture of enone 5 (160 mg, 0.437 mmol) and tri-n-butyltin hydride (0.318 g, 1.09 mmol) in dry dioxane (2.0 mL) was refluxed under nitrogen for 12 hours. The solvent was then removed in vacuo and the residue was purified by preparative TLC using 25% ethyl acetate in hexane as the mobile phase. The product exhibited an $R_f$ of about 0.4. Enol 6 (12-hydroxy-6,6,10,11-tetramethyl-4-propyl-2H,6H,12H-benzo[1,2-b:3,4-b':5,6-b"]-tripyran-2-one) (13.3 mg, 8%) was isolated as an oil from the plate by ethyl acetate elution. This elution may have been inefficient, and the actual yield higher, as indicated by analytical TLC of the crude product. $^1$H-NMR (CDCl$_3$) δ 0.92 (3H, t, J=6.0 Hz, $CH_3$); 1.26 (3H, s, $CH_3$); 1.39 (3H, s, $CH_3$); 1.63 (2H, m, $CH_2$); 1.96 (3H, s, $CH_3$); 2.36 (3H, s, $CH_3$); 2.45 (2H, t, J=6.0 Hz, $CH_2$); 3.65 (1H, s, $H_{12}$); 5.51 (1H, d, J=10.0 Hz, $H_7$); 6.06 (1H, S, $H_3$); 6.67 (1H, d, J=10.0 Hz, $H_8$); 13.25 (1H, br s, OH); MS (EI): 369 (3.8, M+1); 368 (4.4, $M^+$); 367 (8.3, M-1) 366 (28.4, M-2), 351 (100, M-OH); IR(KBr): 1651 (s), 1589 (m)$cm^{-1}$.

EXAMPLE 6

12-Oxocalanolide A [(±)-(7)

A solution containing chromene 4 (344 mg, 1.0 mmol), acetaldehyde diethylacetal (473 mg, 4.0 mmol), trifluoroacetic acid (1.5 mL, 19.4 mmol) and anhydrous pryidine (0.7 mL) was heated at 140° C. under $N_2$. The reaction was monitored by TLC analysis. After 4 hours, the reaction mixture was cooled to room temperature, diluted with ethyl acetate and washed several times with 10% aqueous NaHCO$_3$ and brine. The organic layer was separated and dried over Na$_2$SO$_4$. The solvent was removed in vacuo and the crude product was purified by silica gel column chromatography eluting with ethyl acetate/hexane (2:3). Chromanone (±)-7 (10,11-trans-dihydro-4-propyl-6,6,10,11-tetramethyl-2H,6H,12H-benzo[1,2-b:3,4-b':5,6-b"]-tripyran-2,12-dione) (110 mg, 30% yield) was obtained m.p. 176°≠177° C. (Lit.[5] 130°≠132° C). $^1$HNMR[5] (CDCl$_3$) δ 1.02 (3H, t, J=7.5 Hz, CH$_3$); 1.21 (3H, d, J=6.8 Hz, CH$_3$); 1.51 (3H, d, J=7.0 Hz, CH$_3$); 1.55 (6H, 2s, 2 CH$_3$); 1.63 (2H, sextet, J=7.0 Hz, CH$_2$); 2.55 (1H, dq, J=6.9 Hz, J=11.0 Hz, H$_{11}$); 2.88 (2H, t, J=7.6 Hz, CH$_2$); 4.28 (1H, dq, J=6.3 Hz, J=11.0 Hz, H$_{10}$); 5.60 (1H, d, J=9.9 Hz, H$_7$); 6.04 (1H, s, H$_3$); 6.65 (1H, d, J=11.8 Hz, H$_8$); MS (CI): 369 (100, M+1).

EXAMPLE 7

(±)-Calanolide A (1)

To a solution of chromanone (±)-7 (11 mg, 0.03 mmol) in ethanol (0.4 mL) was added sodium borohydride (2.26 g, 0.06 mmol) and CeCl$_3$(H$_2$O)$_7$ (11.2 mg, 0.03 mmol) in ethanol (5 mL) at room temperature. After stirring for 45 minutes, the mixture was diluted with H$_2$O and extracted with ethyl acetate. The organic layer was dried over Na$_2$SO$_4$ and concentrated. The crude product was purified by preparative TLC eluting with ethyl acetate/hexane (1:1) to afford (±)-calanolide A (1) (10.5 mg, 94%). m.p. 52°–54° C., which increased to 102° C. after it was dried thoroughly (Lit[5]. 56°–58° C.). $^1$H NMR (CDCl$_3$): δ 1.03 (3H, t, J=7.3 Hz, CH$_3$), 1.15 (3H, d, J=6.8 Hz, CH$_3$), 1.46 (3H, d, J=6.8 Hz, CH$_3$), 1.47 (3H, s, CH$_3$), 1.51 (3H, s, CH$_3$), 1.66 (2H, m, CH$_2$), 1.93 (1H, m, H$_{11}$), 2.89 (2H, m, CH$_2$), 3.52 (1H, broad-s, OH), 3.93 (1H, m, H$_{10}$), 4.72 (1H, d, J=7.8 Hz, H$_{12}$), 5.54 (1H, d, J=10.0 Hz, H$_7$), 5.94 (1H, s, H$_3$), 6.62 (1H, d, J=9.9 Hz, H$_8$); MS (CI): 371 (75.4, M+1), 370 (16.1, M$^+$), 353 (100, M-OH); Anal. calcd. for C$_{22}$H$_{25}$O$_5$: C, 71.33; H, 7.07; Found: C, 71.63; H, 7.21.

EXAMPLE 8

5,7-Dihydroxy-4-propylcoumarin (2)

In this Example, kilogram scale preparation of intermediate 2 is described. Into a stirring suspension of phloroglucinol (3574.8 g, 28.4 mol, pre-dried to constant weight) and ethyl butyrylacetate (4600 mL, 28.4 mol) was added concentrated sulfuric acid dropwise at such a rate that the internal temperature did not exceed 40° C. After 100 mL of sulfuric acid was added, the temperature rose to 70° C. and the suspension turned into a yellow solid. Analysis of TLC indicated that the reaction had proceeded to completion. The reaction mixture was diluted with water (10 L) and stirred at ambient temperature overnight. The precipitated product was collected by filtration and then rinsed with water until the filtrate was neutral. A quantity of 4820 g (77% yield) of 5,7-dihydroxy-4-propylcoumarin 2 was obtained after being dried, which was identical with an authentic sample by comparison of TLC, melting point and spectroscopic data.

EXAMPLE 9

5,7-Dihydroxy-8-propionyl-4-propylcoumarin (3)

In this Example, kilogram quantities of intermediate 3 were synthesized using propionic anhydride instead of propionyl chloride. 5,7-dihydroxy-4-propylcoumarin 2 (1710 g, 7.77 mol) and AlCl$_3$ (1000 g, 7.77 mol) were mixed in 1,2-dichloroethane (9 L). The resulting orange suspension was stirred and heated to 70° C. until a solution was obtained. Then, a mixture of propionic anhydride (1010 g. 7.77 mol) and AlCl$_3$ (2000 g, 15.54 mol) in 1,2-dichloroethane (3.4 L) was added dropwise over 3 h. The reaction was allowed to stir at 70° C. for an additional hour. After being cooled down to room temperature, the reaction mixture was poured into a rapidly stirring mixture of ice water and 1N HCl. The precipitated product was taken into ethyl acetate (30 L) and the aqueous solution was extracted with the same solvent (10 L×2). The combined extracts were successively washed with 1N HCl (10 L), saturated aq. NaHCO$_3$ (10 L), and water (10 L). After being dried over MgSO$_4$ and concentrated in vacuo, a solid product (1765 g) was obtained which was washed with ethyl acetate (15 L) and recrystallized from dioxane (9.5 L) to provide 514 g of pure compound 3. From the ethyl acetate washings, an additional 100 g of compound was obtained after recrystallization from dioxane. Thus, the combined yield for compound 3, which was identical with an authentic sample by comparison of TLC, melting point and spectroscopic data, was 29%.

EXAMPLE 10

2,2-Dimethyl-5-hydroxy-6-propionyl-10-propyl-2H, 8H-benzo[1,2-b:3,4-b']dipyran-8-one (4)

In this Example, intermediate 4 was prepared in half kilogram quantities from 3 via modification of the reaction conditions described in Example 3. A mixture of compound 3 (510.6 g, 1.85 mol) and 4,4-dimethoxy-2-methylbutan-2-ol (305.6 g, 2.06 mol) were dissolved in a mixture of toluene (1.5 L) and dry pyridine (51 mL). This mixture was stirred and refluxed; water and methanol formed during the reaction were removed azeotropically via a Dean-Stark trap. The reaction was monitored by TLC. After 6 days, the reaction had proceeded to completion. The mixture was then cooled to ambient temperature and diluted with ethyl acetate (2 L) and 1N HCl (1 L). The ethyl acetate solution was separated and washed with 1N HCl (500 mL) and brine (1 L). After being dried over Na$_2$SO$_4$ and evaporated in vacuo, a quantity of 590 g (93% yield) of compound 4 was obtained which was greater than 95% pure without further purification and was compared with an authentic sample by TLC and spectroscopic data.

EXAMPLE 11

12-Oxocalanolide A (7)

In this Example, chromanone (±)-7 was prepared from two alternative pathways involving either a one-step paraldehyde reaction (procedure A) or a two-step reaction process (procedures B and C).

Procedure A. Paraldehyde One-Step Reaction: To a stirring solution of chromene 4 (350 mg, 1.0 mmol) and PPTS (250 mg, 1.0 mmol) in 1,2-dichloroethane (2 mL) at ambient temperature under N$_2$ was added 3 mL paraldehyde (22.5 mmol). The resulting mixture was refluxed for 7 h. Then, CF$_3$CO$_2$H (1 mL), an additional equivalent of PPTS and 1 mL of paraldehyde were added; the mixture was refluxed overnight. The reaction mixture was neutralized with saturated aqueous NaHCO$_3$ and extracted with ethyl acetate (50 mL×3). The crude product obtained by evaporation under reduced pressure was washed with hexane. The residue was purified by column chromatography eluting with ethyl acetate/hexane (1:2) to afford 100 mg (27% yield) of chromanone (±)-7 and 30 mg (8% yield) of (±)-7a. Chromanone (±)-7 (10,11-trans-dihydro-4-propyl-6,6,10,11-tetramethyl-2H,6H,12H-benzo[1,2-b:3,4-b':5,6-b"]tripyran-2,12-dione) obtained by this method was identical with an authentic sample by comparison of TLC, HPLC and spectroscopic data.

Procedure B LDA/Sulfuric Acid Two-Step Reaction: To a stirring solution of chromene 4 (5.0 g, 14.6 mmol) in THF (75 mL) at −30° C. under $N_2$ was added 18.3 mL (36.5 mmol) of 2M LDA in THF. After 15 min at the same temperature, acetaldehyde (5.0 mL, 89.5 mmol) was added via syringe. The reaction was monitored by TLC analysis. After 1 h, the reaction mixture was quenched at −10° C. with saturated aqueous $NH_4Cl$ (75 mL) and extracted with ethyl acetate (125 mL×3). The combined extracts were washed with brine (125 mL) and dried over $Na_2SO_4$. Removal of solvents in vacuo afforded a reddish oil of (±)-8a and (±)-8b (8.5 g).

The crude (±)-8a and (±)-8b was dissolved in acetic acid (100 mL) and then 50% $H_2SO_4$ (100 mL) was added with stirring. The resulting mixture was heated at 75° C. for 2.5 h and then at 50° C. for 4 h. TLC analysis indicated that the starting material had been consumed. The reaction mixture was determined to contain both chromanone (±)-7 and 10,11-cis-dimethyl derivative (±)-7a in a 1:1 ratio. After cooling to ambient temperature, the reaction mixture was poured into a mixture of ice water (500 mL) and ethyl acetate (500 mL). The layers were separated and the aqueous layer was extracted with ethyl acetate (200 mL×3). The ethyl acetate solutions were combined and washed with saturated aqueous $NaHCO_3$ and brine. After being concentrated in vacuo, the product was purified by chromatography on a silica gel column eluting with ethyl acetate/hexane (2:3) to provide 850 mg (16% yield) of chromanone (±)-7, which was further purified by recrystallation from ethyl acetate/hexane and was identical with an authentic sample by comparison of TLC, HPLC and spectroscopic data.

Procedure C. LDA/Mitsunobu Two-Step Reaction: Into a stirring solution of THF (10 mL) containing triphenylphosphine (1.27 g, 4.80 mmol) and the crude mixture of (±)-8a and (±)-8b, obtained from chromene 4 (1.0 g, 2.34 mmol), 2.5 equivalents of LDA and 6.0 equivalents of acetaldehyde by the procedure described above, was added dropwise diethyl azodicarboxylate (DEAD, 0.77 mL, 4,89 mmol). The resulting reddish solution was stirred at ambient temperature under $N_2$ for 1 h, after which the reaction mixture was quenched with saturated aqueous $NH_4Cl$ and extracted with ethyl acetate (50 mL×3). The extracts were washed with brine and dried over $Na_2SO_4$. After removal of solvents, the crude product was purified by column chromatography on silica gel eluting with ethyl acetate/hexane (2:3) to provide 412 mg (48% yield, based on chromene 4) of chromanone (±)-7, the predominant product of the reaction, which was identical with an authentic sample by comparison of TLC, HPLC and spectroscopic data.

EXAMPLE 12

(±)-Calanolide A (1)

In this Example, (+)-calanolide A was prepared in multi-gram scale using the procedure described in Example 7. To a stirring solution of chromanone (±)-7 (51.5 g, 0.14 mol) in ethanol (1.5 L) was added $CeCl_3(H_2O)_7$ (102 g, 274 mmol). The mixture was stirred for 1.5 h at room temperature under $N_2$ and then cooled to −30° C. with an ethylene glycol/$H_2O$ (1:2 w/w) dry ice bath. After the temperature was equilibrated to −30° C., $NaBH_4$ (21.3 g, 563 mmol) was added and stirred at the same temperature for 8.5 h, at which time the reaction was quenched with $H_2O$ (2 L) and extracted with ethyl acetate (2 L×3). The extracts were combined, washed with brine (2 L) and dried over $Na_2SO_4$. The crude product obtained by removal of solvent under reduced pressure was passed through a short silica gel column to provide 53 g of mixture which contained 68% of (±)-calanolide A, 14% of calanolide B and 13% of chromanone (±)-7 as shown by HPLC. This material was subjected to further purification by preparative HPLC to afford pure (±)-calanolide A (1).

EXAMPLE 13

Chromatographic Resolution of Synthetic (±)-Calanolide A

The synthetic (±)-1 was resolved into enantiomers, (+)-calanolide A and (−)-calanolide A, by preparative HPLC[16]. Thus, using a normal phase silica gel HPLC column (250 mm×4.6 mm I.D. Zorbasil, 5 μm particle size, MAC-MOD Analytical, Inc., PA, USA), the synthetic (±)-1 appeared as one peak with a retention time of 10.15 minutes when hexane/ethyl acetate (70:30) was used as the mobile phase at a flow rate of 1.5 mL/min and a wavelength of 290 nm was used as the uv detector setting. However, on a chiral HPLC column packed with amylose carbamate (250 mm×4.6 mm I.D. Chiralpak AD, 10 μm particle size, Chiral Technologies, Inc., PA, USA), two peaks with retention times of 6.39 and 7.15 minutes in a ratio of 1:1 were observed at a flow rate of 1.5 mL/min. The mobile phase was hexane/ethanol (95:5) and the uv detector was set at a wavelength of 254 nm. These two components were separated using a semi-preparative chiral HPLC column, providing the pure enantiomers of calanolide A. The chemical structures of the separated enantiomers, which were assigned based on their optical rotations and compared with the reported natural product, were characterized by spectroscopic data. HPLC chromatograms of (±)-calanolide A and its optical forms are shown in FIG. 6.

(+)-Calanolide A (1): mp 47°–50° C. (Lit.[17] 45°–48° C.);$[\alpha]^{25}_D$=+68.8° (CHCl$_3$, c 0.7) (Lit.[17] $[\alpha]^{25}_D$=+66.6°) (CHCl$_3$; c 0.5); $^1$H NMR (CDCl$_3$) δ 1.03 (3H, t, J=7.3 Hz, CH$_3$), 1.15 (3H, d, J=6.8 Hz, CH$_3$), 1.46 (3H, d, J=6.4 Hz, CH$_3$), 1.47 (3H, s, CH$_3$), 1.51 (3H, s, CH$_3$), 1.66 (2H, m, CH$_2$), 1.93 (1H, m, H$_{11}$), 2.89 (2H, m, CH$_2$), 3.52 (1H, d, J=2.9 Hz, OH), 3.93 (1H, m, H$_{10}$), 4.72 (1H, dd, J=7.8 Hz, J=2.7 Hz, H$_{12}$), 5.54 (1H, d, J=9.9 Hz, H$_7$), 5.94 (1H, s, H$_3$), 6.62 (1H, d, J=9.9 Hz, H$_8$); $^{13}$C NMR (CDCl$_3$) δ 13.99 (CH$_3$), 15.10 (CH$_3$), 18.93 (CH$_3$), 23.26 (CH$_2$), 27.38 (CH$_3$), 28.02 (CH$_3$), 38.66 (CH$_2$), 40.42 (CH), 67.19 (CH-OH), 77.15 (CH-O), 77.67 (C-O), 104.04 (C$_{4a}$), 106.36 (C$_{8a}$ and C$_{12a}$), 110.14 (C$_3$), 116.51 (C$_8$), 126.97 (C$_7$), 151.14 (C$_{4b}$), 153.10 (C$_{8b}$), 154.50 (C$_{12b}$), 158.88 (C$_4$), 160.42 (C=O); CIMS: 371 (100, M+1), 370 (23.6,M$^+$), 353 (66.2, M-OH); 1R: 3611 (w) and 3426 (m, broad, OH), 1734 (vs. C=O), 1643 (m), 1606 (m) and 1587 (vs) cm$^{-1}$; UV $\lambda_{max}$ (methanol): 204 (32,100), 228 (23,200), 283 (22,200), 325 (12,700) nm; Anal. calcd. for C$_{22}$H$_{26}$O$_5$¼H$_2$O: C, 70.47; H, 7.12; Found: C, 70.64; H, 7.12.

(−)-Calanolide A (1): mp 47°–50° C.; $[\alpha]^{25}_D$=−75.6° (CHCl$_3$, c 0.7) Lit.[17]$[\alpha]^{25}_D$=−66.6° (CHCl$_3$, c 0.5); $^1$H NMR (CDCl$_3$) δ 1.03 (3H, t, J=7.4 Hz, CH$_3$), 1.15 (3H, d, J=6.8 Hz, CH$_3$), 1.46 (3H, d, J=6.3 Hz, CH$_3$), 1.47 (3H, s, CH$_3$), 1.51 (3H, s, CH$_3$), 1.66 (2H, m, CH$_2$), 1.93 (1H, m, H$_{11}$), 2.89 (2H, m, CH$_2$), 3.50 (1H, d, J=2.9 Hz, OH), 3.92

(1H, m, H$_{10}$), 4.72 (1H, dd, J=7.8 Hz, J=2.7 Hz, H$_{12}$), 5.54 (1H, d, J=10.0 Hz, H$_7$), 5.94 (1H, s, H$_3$), 6.62 (1H, d, J=10.0 Hz, H$_8$); $^{13}$C NMR (CDCl$_3$) δ 13.99 (CH$_3$), 15.10 (CH$_3$), 18.93 (CH$_3$), 23.36 (CH$_2$), 27.38 (CH$_3$), 28.02 (CH$_3$), 38.66 (CH$_2$), 40.42 (CH), 67.19 (CH-OH), 77.15 (CH-O), 77.67 (C-O), 104.04 (C$_{4a}$), 106.36 (C$_{8a}$ and C$_{12a}$), 110.14 (C$_3$), 116.51 (C$_8$), 126.97 (C$_7$), 151.14 (C$_{4b}$), 153.11 (C$_{8b}$), 154.50 (C$_{12b}$), 158.90 (C$_4$), 160.44 (C=O); CIMS: 371 (95.2, M+1), 370 (41.8,M$^+$), 353 (100, M-OH); IR: 3443 (m, broad, OH), 1732 (vs, C=O), 1643 (m), 1606 (m) and 1584 (vs) cm$^{-1}$; UV λ$_{max}$ (methanol): 200 (20,500), 230 (19,400), 283 (22,500), 326 (12,500) nm; Anal. calcd. for (C$_{22}$H$_{26}$O$_5$·¼H$_2$O: C, 70.47; H, 7.12; Found: C, 70.27; H, 7.21.

EXAMPLE 14

Enzymatic Resolution of (±)-Calanolide A

To a magnetically stirred suspension of (±)-calanolide A, prepared by the method of the present invention, and vinyl butyrate (0.1 mL) in hexane (0.5 mL) at ambient temperature was added 1 mg of lipase PS-13 (Pseudomonas Species) (Sigma Corporations, St. Louis, Mo., USA). The reaction mixture was stirred and monitored by conventional means such as TLC analysis. At 10 days, an additional 1 mg of lipase PS-13 was added. After stirring for a total of 20 days, the reaction was stopped because there was no obvious increase in ester formation. The enzyme was filtered out and the filtrate was concentrated to dryness. The residue was analyzed by HPLC (see Example 13), which showed that 21% of (−)-calanolide A had been converted into its butyrate ester form. The enriched (+)-calanolide A and the butyrate ester of (−)-calanolide A can be easily separated by conventional means such as column chromatography. The enriched (+)-calanolide A may be repeatedly treated with vinyl butyrate and lipase PS-13 as described above so as to obtain high e.e. of (+)-calanolide A.

EXAMPLE 15

Aldol Reaction (Scheme III) of Chromene 4 in the Presence of LDA

To a stirring solution of chromene 4 (1.0 g, 2.9 mmol) in THF (15 mL) at −78° C. under N$_2$ was added 2M LDA in THF (3.2 mL, 6.4 mmol). After 1 h at the same temperature, acetaldehyde (1.0 mL, 17.5 mmol) was added via syringe. The reaction was monitored by TLC analysis. After 1 h, the reaction mixture was quenched with a precooled 2N HCl in methanol (15 mL) and extracted with ethyl acetate (30 mL×3). The combined extracts were washed with brine and dried over Na$_2$SO$_4$. Removal of solvents in vacuo afforded a reddish oil, which was purified by silica gel column chromatography eluting with a discontinuous gradient of 5%, 10%, 15%, 25% and 30% of ethyl acetate in hexane to obtain 780 mg (70% yield) of a mixture of (±)-8a and (±)-8b in a ratio of 1:1, as indicated by $^1$H NMR. Pure samples of (±)-8a and (±)-8b were obtained by carefully collecting the front fractions and later fractions from column chromatography, analytical data of which were described below:

6,6-Dimethyl-9-hydroxy-10-[2(S*)-methyl-3(R*)-hydroxybutyro]-4-propyl-2H,6H-benzo[1,2-b:3,4-b']dipyran-2-one [syn-(±)8a]. m.p. 66°–67° C.; $^1$H NMR (CDCl$_3$): 1.05 (3H, t, J=7.3 Hz, CH$_3$), 1.30 (3H, d, J=6.0 Hz, CH$_3$), 1.33 (3H, d, J=6.6 Hz, CH$_3$), 1.54 (6H, s, 2 CH$_3$), 1.67 (2H, m, CH$_2$), 2.62 (1H, broad-s, OH), 2.91 (2H, t, J=7.7 Hz, CH$_2$), 3.98 (1H, dq, J=2.7 Hz, J=7.0 Hz, H$_2$), 4.29 (1H, m, H$_3$), 5.59 (1H, d, J=10.0 Hz, H$_7$), 6.01 (1H, s, H$_3$), 6.73 (1H, d, J=10.0 Hz, H$_8$), 14.11 (1H, s, OH); 1H NMR (DMSO-d$_6$): 1.00 (3H, t, J=7.3 Hz, CH$_3$), 1.13 (3H, d, J-6.6 Hz, CH$_3$), 1.16 (3H, d, J=6.8 Hz, CH$_3$), 1.49 (3H, s, CH$_3$), 1.50 (3H, s, CH$_3$), 1.60 (2H, apparent sextet, J=7.6 Hz, CH$_2$), 2.88 (2H, apparent dd, J=6.3 Hz, J=9.0 Hz, CH$_2$), 3.39 (1H, broad-s, OH), 3.68 (1H, dq, J=5.2 Hz, J=6.7 Hz, H$_2$·), 3.97 (1H, apparent quintet, J=5.8 Hz, H$_3$·), 5.78 (1H, d, J=10.1 Hz, H$_7$), 6.11 (1H, s, H$_3$), 6.63 (1H, d, J=10.1 Hz, H$_8$), 13.25 (1H, s, OH); MS (CI): 388 (36.5, M+2), 387 (100, M+1), 386 (6.6, M$^+$), 369 (21.6, M-OH), 343 (50.7, M-C$_3$H$_7$); UV (methanol) nm: 199 (41,000), 270 (25,700), 306 (21,900); IR (KBr) cm$^{-1}$: 3395 (broad, m, OH), 1734 (s) and 1707 (vs) (C=O), 1644 (m), 1608 (vs), 1578 (vs) and 1547 (vs); Anal. Calcd. for C$_{22}$H$_{26}$O$_6$·⅓H$_2$O: C, 67.33; H, 6.84; Found: C, 67.43; H, 6.93.

6,6-Dimethyl-9-hydroxy-10-[2(S*)-methyl-3(S*)-hydroxybutyro]-4-propyl-2H,6H-benzo[1,2-b:3,4-b']dipyran-2-one [anti-(±)-8b]. m.p. 115° C.; $^1$H NMR (CDCl$_3$): 1.05 (3H, t, J=7.4 Hz, CH$_3$), 1.25 (3H, d, J=6.4 Hz, CH$_3$), 1.29 (3H, d, J=6.9 Hz, CH$_3$), 1.54 (6H, s, 2 CH$_3$), 1.66 (2H, apparent sextet, J=7.6 Hz, CH$_2$), 2.92 (2H, t, J=7.8 Hz, CH$_2$), 2.95 (1H, d, J=5.5 Hz, OH), 3.98 (1H, dq, J=6.1 Hz, J=6.8 Hz, H$_2$·), 4.22 (1H, apparent sextet, J=6.2 Hz, H$_3$·), 5.59 (1H, d, J=10.1 Hz, H$_7$), 6.03 (1H, s, H$_3$), 6.73 (1H, d, J=10.1 Hz, H$_8$), 14.25 (1H, s, OH); $^1$H NMR (DMSO-d$_6$): 1.00 (3H, t, J=7.3 Hz, CH$_3$), 1.11 (6H, d, J=6.7 Hz, 2 CH$_3$), 1.49 (3H, s, CH$_3$), 1.50 (3H, s, CH$_3$), 1.60 (2H, apparent sextet, J=7.3 Hz, CH$_2$), 2.85, 2.90 (2H, t-AB type, J=7.7 Hz, J$_{AB}$=21.4 Hz, CH$_2$), 3.59 (1H, apparent quintet, J=7.1 Hz, H$_2$·), 3.96 (1H, apparent quintet, J=7.0 Hz, H$_3$·), 4.97 (1H, broad-s, OH), 5.78 (1H, d, J=10.1 Hz, H$_7$), 6.10 (1H, s, H$_3$), 6.63 (1H, d, J=10.0 Hz, H$_8$), 12.69 (1H, s, OH); MS (EI): 387 (2.8, M+1), 386 (9.4, M$^+$), 371 (5.3, M-CH$_3$), 369 (1.5, M-OH), 353 (54.0, M-CH$_3$-H$_2$O), 342 (22.5, M-C$_3$H$_7$-1), 327 (100, M-C$_3$H$_7$-OH+1); UV (methanol) nm: 199 (41, 000), 270 (25,700), 306 (21,900); IR (KBr) cm$^{-1}$: 3478 (broad, m, OH), 1736 (vs) and 1707 (vs) (C=O), 1645 (m), 1603 (vs), 1584 (vs, sh); Anal. Calcd. for C$_{22}$H$_{26}$O$_6$·⅓H$_2$O: C, 67.33; H, 6.84; Found: C, 67.34; H, 6.45.

EXAMPLE 16

Aldol Reaction (Scheme III) of Chromene 4 in the Presence of LDA/TiCl$_4$

In this Example, two procedures are provided for effecting the Aldol reaction. Procedure B was found to be more suitable for scale-up because of simplification of temperature control.

Procedure A. To a stirring solution of chromene 4 (200 mg, 0.58 mmol) in dry methylene chloride (10 mL) at −78° C. under N$_2$ was added 2M solution of LDA in heptane/THF/ethyl benzene (0.64 mL, 1.28 mmol). The reaction mixture was stirred at −78° C. for 30 min and then TiCl$_4$ (0.13 mL, 1.17 mmol) was added. The resulting yellow solution was warmed to −40° C. and stirred for 45 min. The mixture was recooled to −78° C., and acetaldehyde (150 mg, 3.5 mmol) was added via syringe. After 4 h, the reaction was quenched by slow addition of pre-cooled saturated NH$_4$Cl (10 mL). Water (3 mL) was added to dissolve the oily solid. The mixture was extracted with ethyl acetate (50 mL×3). The combined extracts were washed with brine (100 mL) and dried over MgSO$_4$. The crude product obtained by evaporation was purified by silica gel column chromatography, eluting with hexane/ethyl acetate (5:1) to afford unreacted chromene 4 (30 mg, 15% yield) and syn-(±)-8a (140 mg, 61% yield), which contained 7% of anti-(±)-8b as shown by HPLC.

Procedure B. To a stirring solution of chromene 4 (20 g, 58.4 mmol) in dry methylene chloride (300 mL) at −40° C. under $N_2$ was added $TiCl_4$ (19 mL, 175 mmol). The mixture was then cooled to −78° C., followed by slow addition of 2M solution of LDA in heptane/THF/ethyl benzene (64 mL, 128 mmol). After 30 min at the same temperature, acetaldehyde (9 mL, 175 mmol) was added via syringe. The reaction mixture was stirred at −78° C. for 2 h. TLC analysis (hexane/ethyl acetate, 5:1) indicated that approximately 90% chromene 4 had been converted. The mixture was then poured into pre-cooled saturated $NH_4Cl$ (240 mL). Water (120 mL) was added to dissolve the oily solid and the mixture was stirred for 20 min. Layers were separated and the aqueous solution was extracted with ethyl acetate (600 mL×3). The combined extracts were washed with brine (600 mL) and dried over $MgSO_4$. Removal of solvents in vacuo afforded a reddish oil (23 g), which was taken up into ether (250 mL). The undissolved residue was filtered and the etheral solution was concentrated to half volume and then slowly added into rapidly stirring hexane cooled at −78° C. Precipitates thus formed were collected by filtration to afford syn-(±) -8a (11.1 g, 49% yield), which contained 4% of (±)-8b as shown by HPLC.

EXAMPLE 17

Enzymatic Resolution of syn-(±)-8a (Scheme III)

Into a stirring solution of syn-(±)-8a (7.6 g, 19.7 mmol) in tert-butyl methyl ether (130 mL) at ambient temperature under $N_2$ were added successively vinyl acetate (33 mL), 4 Å molecular sieves (17 g) and Lipase PS-30 (3.8 g) (Amano Enzyme U.S.A. Co., Ltd., Troy, Va.). The resulting mixture was vigorously stirred at ambient temperature for 4 days, whereupon it was filtered through celite and the celite was washed with ethyl acetate (20 mL). The crude product obtained from evaporation was subjected to silica gel column chromatography eluting with a discontinuous gradient of 5%, 10%, 15%, 25%, 30% and 40% of ethyl acetate in hexane to afford 4.8 g (63% yield) of the acetate (9), which was contaminated by over-acylation product of (+)-8a, and 2.8 g (37% yield) of pure syn-(+)-8a.

6,6-Dimethyl-9-hydroxy-10-[2(R)-methyl-3(S)-hydroxybutyro]-4-propyl-2H,6H-benzo[1,2-b:3,4-b'] dipyran-2-one [syn-(+)-8a]. m.p. 82°–85° C.; $[\alpha]^{25}_D=0°$ ($CHCl_3$, c 0.7; $[\alpha]^{25}_D=0°$ ($CHCl_3$, c 0.35); $^1H$ NMR ($CDCl_3$): 1.05 (3H, t, J=7.4 Hz, $CH_3$), 1.31 (3H, d, J=5.6 HZ, $CH_3$), 1.33 (3H, d, J=6.9 Hz, $CH_3$), 1.54 (6H, s, 2 $CH_3$), 1.67 (2H, apparent sextet, J=7.6 Hz, $CH_2$), 2.75 (1H, broad-s, OH), 2.91 (2H, t, J=7.8 Hz, $CH_2$), 3.98 (1H, dq, J=2.7 Hz, J=7.0 Hz, $H_2$), 4.30 (1H, dq, J=2.7 Hz, J=6.5 Hz, $H_3$), 5.59 (1H, d, J=10.2 Hz, $H_7$), 6.01 (1H, s, $H_3$), 6.72 (1H, d, J=10.3 Hz, $H_8$), 14.10 (1H, s, OH); $^{13}C$ NMR ($CDCl_3$); δ 10.42 ($CH_3$), 14.00 ($CH_3$), 20.61 ($CH_3$), 23.32 ($CH_2$), 28.31 (2 $CH_3$), 39.05 ($CH_2$), 50.93 (CHCO), 68.03 (CH-O), 79.92 (C-O), 102.95 ($C_{8a}$), 103.69 ($C_{4a}$), 106.12 ($C_{10}$), 110.60 ($C_3$), 115.80 ($C_8$), 126.51 ($C_7$), 157.03 and 157.11 ($C_9$ and $C_{10a}$), 158.58 ($C_{4b}$), 159.01 ($C_4$), 163.13 ($CO_2$), 210.61 (C=O); MS (CI): 388 (33.4, M+2), 387 (100, M+1), 386 (8.5, M$^+$), 369 (36.3, M-OH), 343 (97.2, M-$C_3H_7$); Anal. calcd. for $C_{22}H_{26}O_6$: C, 68.38; H, 6.78; Found: C, 68.02; H, 6.62.

EXAMPLE 18

10(R), 11(R)-trans-Dihydro-6,6,10,11-tetramethyl-4-propyl-2H,6H,12H-benzo-[1,2-b:3,4-b':5,6-b"] tripyran-2,12-dione [Scheme III, (+)-7]

Into a stirring solution of syn-(+)-8a (2.0 g, 5.2 mmol) in THF (50 mL) were added triphenylphosphine (1.9 g, 7.2 m-mol) and diethyl azodicarboxylate (DEAD, 1.2 mL, 7.6 mmol). The resulting reddish solution was stirred at ambient temperature under $N_2$ for 5 h, after which the reaction mixture was quenched with saturated aqueous $NH_4Cl$ (20 mL) and extracted with ethyl acetate (50 mL×3). The combined extracts were washed with brine (50 mL) and dried over $Na_2SO_4$. The crude product (5.8 g) obtained by evaporation was purified by column chromatography on silica gel eluting with a discontinuous gradient of 10%, 20%, 30% and 40% of ethyl acetate in hexane to afford 1.2 g (63% yield) of pure (+)-7. mp 171°–175° C.; $[\alpha]^{25}_D=+37.9°$ ($CHCl_3$, c 0.73); $^1H$ NMR [$CDCl_3/CD_3OD$ (3:1)]: 1.06 (3H, t, J=7.3 Hz, $CH_3$), 1.22 (3H, d, J=7.0 Hz, $CH_3$), 1.54 (3H, s, $CH_3$), 1.57 (3H, d, J=6.0 Hz, $CH_3$), 1.58 (3H, s, $CH_3$), 1.67 (2H, apparent sextet, J=7.6 Hz, $CH_2$), 2.59 (1H, dq, J=6.9 Hz, J=11.1 Hz, $H_{11}$), 2.92 (2H, t, J=7.8 Hz, $CH_2$), 4.37 (1H, dq, J=6.3 Hz, J=11.1 Hz, $H_{10}$), 5.66 (1H, d, J=10.1 Hz, $H_7$), 6.05 (1H, s, $H_3$), 6.67 (1H, d, J=10.1 Hz, $H_8$); $^{13}C$ NMR [$CDCl_3/CD_3OD$ (3:1)]: δ 9.87 ($CH_3$), 13.34 ($CH_3$), 18.97 ($CH_3$), 22.85 ($CH_2$), 27.40 and 27.73 (2 $CH_3$), 38.38 ($CH_2$), 46.82 (CHCO), 79.17 (CH-0 and C-0), 102.91 ($C_{8a}$), 104.11 ($C_{4a}$), 105.46 ($C_{12a}$), 111.09 ($C_3$), 115.21 ($C_8$), 126.90 ($C_7$), 154.83 and 155.86 ($C_{8b}$ and $C_{12b}$), 157.89 ($C_{4b}$), 158.99 ($C_4$), 160.27 ($CO_2$), 190.50 (C=O); MS (CI): 370 (49.0, M+2), 369 (100, M+1), 368 (17.2, M$^+$); Anal. Calcd. for $C_{22}H_{24}O_5$: C, 71.72; H, 6.57; Found: C, 71.46; H, 6.60.

(+)-Calanolide A: To a stirring solution of (+)-7 (660 mg, 1.79 mmol) in ethanol (18 mL) were added $CeCl_3(H_2O)_7$ (2.7 g, 7.17 mmol) and triphenylphosphine oxide (2.0 g, 7.17 mmol). The mixture was stirred for 1 h at ambient temperature under $N_2$ and then cooled to −30° C. with an ethylene glycol/$H_2O$ (1:2 w/w) dry ice bath. After the temperature was equilibrated to −30° C., $NaBH_4$ (271 mg, 7.17 mmol) was added and stirred at the same temperature for 5.5 h, at which time the reaction was quenched with saturated $NH_4Cl$ (20 mL) and extracted with ethyl acetate (30 mL×3). The combined extracts were washed with brine (50 mL) and dried over $Na_2SO_4$. The crude product obtained by removal of solvent under reduced pressure was purified by column chromatography on silica gel eluting with 20% of ethyl acetate in hexane to afford 520 mg (78% yield) of a mixture containing 90% of (+)-calanolide A[(+)-1] and 10% of (+)-calanolide B. (+)-Calanolide A [(+)-1] was further separated from (+)-calanolide B by normal phase HPLC and was identical with an authentic sample.

EXAMPLE 19

Enzymatic Resolution (Scheme IV) of anti-(±)-8b

Into a stirring solution of anti-(±)-8b (3.0 g, 7.8 mmol) in tert-butyl methyl ether (78 mL) at ambient temperature under $N_2$ were added successively vinyl acetate (26 mL), 4 Å molecular sieves (3.0 g) and Lipase PS-30 (1.5 g) (Amano Enzyme U.S.A. Co., Ltd., Troy, Va.). The resulting mixture was vigorously stirred at ambient temperature for 41 h, whereupon it was filtered through the celite and the celite was washed with ethyl acetate (20 mL). The crude yellowish solid product (3.2 g) obtained from evaporation was purified by silica gel column chromatography eluting with a discontinuous gradient of 5%, 10%, 15%, 25%, 30% and 40% of ethyl acetate in hexane to afford 1.68 g (50% yield) of the acetate (10) and 1.37 g (46% yield) of anti-(+)-8b.

6,6-Dimethyl-9-hydroxy-10-[2(S)-methyl-3(S)-hydroxybutyro]-4-propyl-2H,6H-benzo-[1,2-b:3,4-b'] dipyran-2-one [anti-(+)-8b]. m.p. 131°–134° C.; $[\alpha]^{25}_D=+45.3°$ ($CHCl_3$, c 0.72); $^1H$ NMR ($CDCl_3$): 1.06 (3H, t, J=7.3 Hz, $CH_3$), 1.25 (3H, d, J=6.6 Hz, $CH_3$), 1.29 (3H, d, J=6.7

Hz, $CH_3$), 1.55 (6H, s, 2 $CH_3$), 1.67 (2H, apparent sextet, J=7.6 Hz, $CH_2$), 2.92 (2H, t, J=7.8 Hz, $CH_2$), 2.96 (1H, d, J=7.1 Hz, OH), 3.98 (1H, apparent quintet, J=6.1 Hz, $H_2$), 4.22 (1H, apparent sextet, J=6.0 Hz, $H_{3'}$), 5.60 (1H, d, J=10.1 Hz, $H_7$), 6.03 (1H, s, $H_3$), 6.73 (1H, d, J=10.1 Hz, $H_8$), 14.25 (1H, s, OH); MS (CI): 388 (41.4, M+2), 387 (100, M+1), 386 (13.0, $M^+$), 369 (42.8, M-OH), 343 (63.8, M-$C_3H_7$); Anal. calcd. for $C_{22}H_{26}O_6$: C, 68.38; H, 6.78; Found: C, 68.50; H, 6.91.

6,6-Dimethyl-9-hydroxy-10-[2(R)-methyl-3(R)-acetoxybutyro]-4-propyl-2H,6H-benzo-[1,2-b:3,4-b']dipyran-2-one [anti-(+)-10]. m.p. 61°–64° C.; $[\alpha]^{25}_D$=+30.0° ($CHCl_3$, c 0.73); $^1$H NMR ($CDCl_3$): 1.06 (3H, t, J=7.2 Hz, $CH_3$), 1.29 (3H, d, J=6.2 Hz, $CH_3$), 1.32 (3H, d, J=6.7 Hz, $CH_3$), 1.54 (6H, s, 2 $CH_3$), 1.67 (2H, apparent sextet, J=7.6 Hz, $CH_2$), 1.93 (3H, s, $CH_3CO$), 2.91 (2H, m, $CH_2$), 4.18 (1H, dq, J=8.3 Hz, J=6.9 Hz, $H_{2'}$), 5.34 (1H, dq, J=8.2 Hz, J=6.4 Hz, $H_{3'}$), 5.59 (1H, d, J=10.1 Hz, $H_7$), 6.02 (1H, s, $H_3$), 6.73 (1H, d, J=10.1 Hz, $H_8$), 14.02 (1H, s, OH); MS (CI): 430 (37.1, M+2), 429 (95.2, M+1), 428 (7.2, M+), 369 (100, M-AcO); Anal. calcd. for $C_{24}H_{28}O_7$: C, 67.28; H, 6.59; Found: C, 67.75: H, 6.90.

EXAMPLE 20

5,7-Dihydroxy-4-trifluoromethylcoumarin (Scheme V, 11a, $R_1$=$CF_3$, $R_2$=H)

Into a mixture of anhydrous phloroglucinol (8 g, 63.0 mmol) and ethyl 4,4,4-trifluoroacetoacetate (12 g, 65.0 mmol) was added concentrated $H_2SO_4$ (11 mL). The resulting mixture was heated at 100° C. and stirred for 2 h, whereupon the reaction mixture was cooled to room temperature. Ice (100 g) and $H_2O$ (150 mL) were then added while cooling with ice bath. The precipitated product was collected and dissolved in AcOEt (100 mL), which was washed with $H_2O$ and dried over $Na_2SO_4$. The crude product (16 g) obtained by evaporation under vacuum was chromatographed in methylene chloride-ethanol (95:5) to furnish 11a (6 g, 39% yield) along with another unidentified product. 11a: m.p. 250°–252° C. after recrystallization from methylene chloride-hexane. $^1$H NMR (DMSO-$d_6$): 6.30 (1H, s, $H_3$), 6.33 and 6.54 (2H, 2 s, $H_7$ and $H_8$), 10.68 and 10.99 (2H, 2 s, 2 OH); MS (CI) m/z: 246 (100, $M^+$), 226 (14.6, M-HF), 218 (10.0, M-CO), 198 (59.6, M-HF-CO); IR (KBr) $cm^{-1}$: 3537(m, sh) and 3384 (s, broad, OH), 1709 (s, C=O), 1618 (s, C=C—C=O), 1154 (s, C-F); Anal. Calcd. for $C_{10}H_5F_3O_4$: C, 48.80; H, 2.05; Found, C, 48.83; H, 2.10.

EXAMPLE 21

5,7-Dihydroxy-8-isobutyryl-4-propylcoumarin (Scheme V, 12a, $R_1$=n—Pr, $R_2$=H, $R_3$=$R_4$=Me)

Into a flame-dried 500 mL 3-necked round-bottom flask was placed 5,7-dihydroxy-4-propylcoumarin (2, 10.0 g, 48.1 mmol) and $AlCl_3$ (12.0 g, 90 mmol) under $N_2$. Dichloroethane (120 mL) was then added, and the solution warmed to 75° C. with a water bath with mechanical stirring. After stirring 15 min at 75° C., a homogenous solution was obtained. To this solution was added a mixture of isobutyric anhydride (7.61 g, 48.1 mmol) and $AlCl_3$ (12.0 g) in dichloroethane (60 mL) dropwise over 1 h. After addition was completed, the solution was stirred for an additional 1 h at 75° C., then cooled to room temperature. The solution was poured into a mixture of crushed ice (100 g) and 2N HCl (100 mL), at which point a white precipitate formed. The mixture was diluted with ethyl acetate (1.8 L), and the organic layer separated. The organic solution was washed sequentially with 1N HCl (500 mL) and saturated brine (500 mL), dried over magnesium sulfate, filtered and evaporated to provide an orange powder. The powder was triturated with acetone (80 mL), collected on a Büchner funnel, rinsed with diethyl ether (80 mL) and dried to provide a cream colored solid (4.22 g). The product was further purified via recrystallization from ethanol (200 mL) to give colorless plates (3.63 g, 26.0%); mp 263°–265° C., with softening at 250° C. (Lit.[15] 272°≠273° C.); $^1$H NMR (DMSO-$d_6$): 0.95 (3H, t, J=7.4 Hz, $CH_3$), 1.08 (6H, d, J=6.9 Hz, 2 $CH_3$), 1.59 (2H, sextet, J=7.4 Hz, $CH_2$), 2.87 (2H, t, J=7.4 Hz, $CH_2$), 3.24 (1H, heptet, J=6.9 Hz, CH), 5.93 (1H, s, $H_3$), 6.37 (1H, s, $H_6$), 11.16 and 11.44 (2H, 2 s, 2 OH); EIMS: 290 (23.2, $M^+$), 247 (100, M-$C_3H_7$), 219 (11.1, M-$C_3H_7CO$); IR (KBr) $cm^{-1}$: 3216 (s, OH), 1684 (s, C=O); Anal. calcd. for $C_{16}H_{18}O_5$: C, 66.20; H, 6.25. Found: C, 66.15; H, 6.21.

EXAMPLE 22

6,6-dimethyl-9-hydroxy-10-isobutyryl-4-propyl-2H, 6H-benzo[1,2-b:3,4-b']dipyran-2-one (Scheme V, 13a, $R_1$=n—Pr, $R_2$=$R_7$=H, $R_3$=$R_4$=$R_5$=Me)

To a solution of 12a (2.90 g, 10.0 mmol) in pyridine (5 mL) was added 4,4-dimethoxy-2-methylbutan-2-ol (1.49 g, 10.1 mmol), and the solution heated to reflux. After heating for 40 h, TLC indicated complete consumption of starting material. The reaction was cooled to room temperature and the pyridine removed in vacuo. The dark colored residue was dissolved in ethyl acetate (50 mL) and washed sequentially with 2N HCl (50 mL×2), 5% $NaHCO_3$ (50 mL) and saturated brine (50 mL). The solution was dried over magnesium sulfate, filtered and evaporated to provide a dark orange solid, which was chromatographed on a silica gel column (125 g) and eluted with ethyl acetate/hexane (1:4) to afford the pure product as a bright orange crystalline solid (2.51 g, 70.5%); mp 70°–72° C.; $^1$H NMR ($CDCl_3$): 1.05 (3H, t, J=7.3 Hz, $CH_3$), 1.26 (6H, d, J=6.7 Hz, 2 $CH_3$), 1.54 (6H, s, 2 $CH_3$), 1.66 (2H, sextet, J=7.7 Hz, $CH_2$), 2.91 (2H, t, J=7.7 Hz, $CH_2$), 4.06 (1H, heptet, J=6.7 Hz, CH), 5.58 (1H, d, J=9.9 Hz, $H_7$), 6.01 (1H, s, $H_3$), 6.73 (1H, d, J=9.9 Hz, $H_8$), 14.45 (1H, s, OH); EIMS: 356 (48.0, $M^+$), 341 (100, M-$CH_3$), 313 (65.0, M-$C_3H_7$); IR (KBr) $cm^{-1}$: 1732; Anal. calcd. for $C_{21}H_{24}O_5$. C, 70.77; H, 6.79. Found: C, 70.73; H, 6.78.

EXAMPLE 23

(±)-6,6-Dimethyl-10-(2,2-dimethyl-3-hydroxybutyro)-9-hydroxy-4-propyl-2H,6H-benzo [1,2-b:3,4-b']dipyran-2-one (Scheme V, 14a, $R_1$=n-Pr, $R_2$=$R_7$=$R_8$=H, $R_3$=$R_4$=$R_5$=$R_6$=$R_9$=Me)

To a solution of 13a (1.25 g, 3.51 mmol) in anhydrous THF (20 mL) under $N_2$ at −78° C. was added LDA (2.0M in heptane/THF/ethyl benzene, 4.39 mL, 8.78 mmol) dropwise, and the resulting red solution stirred for 1 h. A solution of acetaldehyde (1.54 g, 35.1 mmol) in THF (6 mL) was added dropwise, and the reaction mixture stirred at −78° C. for 3 hours whereupon the reaction was quenched by slowly adding 2.5M ethanolic HCl (10 mL), and the solution then allowed to warm to room temperature. The solvent was evaporated in vacuo and the residue partitioned between ethyl acetate (100 mL) and saturated $NaHCO_3$ (100 mL). The organic layer was collected and washed with saturated brine (100 mL), dried over magnesium sulfate, filtered and evaporated to provide a brown solid. The product was triturated with ethyl acetate/hexane (1:1, 15 mL), collected on a Buchner funnel, rinsed with fresh solvent and air dried to give the desired product as a white powder (654 mg, 46.6%). An analytical sample was obtained via recrystallization from ethyl acetate/hexane (1:1); mp 190°–191° C.; $^1$H NMR (CDCl$_3$): 1.04 (3H, t, J=7.4 Hz, CH$_3$), 1.25 (3H, s, CH$_3$), 1.29 (3H, d, J=6.4 Hz, CH$_3$), 1.33 (3H, s, CH$_3$), 1.48 (3H, s, CH$_3$), 1.52 (3H, s, CH$_3$), 1.66 (2H, sextet, J=7.5 Hz, CH$_2$), 2.39 (1H, broad-s, OH), 2.88 (m, 2H, CH$_2$), 4.47 (1H, q, J=6.4 Hz, CH), 5.56 (1H, d, J=10.0 Hz, H$_7$), 5.92 (1H, s, H$_3$), 6.64 (1H, d, J=10.0 Hz, H$_8$), 8.99 (1H, s, OH): EIMS: 400 (1.1, M$^+$), 356 (37.5, M-C$_2$H$_4$O), 341 (100, M-CH$_3$-C$_2$H$_4$O), 313 (68.2, M-C$_3$H$_7$-C$_2$H$_4$O); IR (KBr) cm$^{-1}$: 3246 (broad-s, OH), 1686 (s, C=O); Anal. calcd. for C$_{23}$H$_{28}$O$_6$: C, 68.98; H, 7.05. Found. C, 69.03; H, 6.99.

EXAMPLE 24

(±)-6,6-Dimethyl-10-(2,3-dimethyl-3-hydroxybutyro)-9-hydroxy-4-propyl-2H,6H-benzo[1,2-b:3,4-b']dipyran-2-one (Scheme V, 14b, R$_1$=n-Pr, R$_2$=R$_3$=R$_7$=H, R$_4$=R$_5$=R$_6$R$_8$=R$_9$=Me)

To a suspension of 4 (1.2 g, 3.50 mmol) in THF (16 mL) at −78° C. was added a solution of LDA in heptane/THF/ethyl benzene (2M, 5.0 mL, 10.0 mmol) dropwise under N$_2$. The solution was stirred at −78° C. for 1 h and acetone (2.0 mL, 27.2 mmol) was added quickly via syringe. The solution was stirred at −78° C. for 3 h, quenched with methanolic HCl (2M, 15 mL) at −78° C., then allowed to warm to room temperature. The reaction mixture was concentrated and partitioned between ethyl acetate (150 mL) and saturated NaHCO$_3$ (100 mL). The organic layer was collected and washed with saturated brine (50 mL), dried over magnesium sulfate, filtered and concentrated to provide a red oil (1.36 g), an analytical sample of which was obtained via silica gel column chromatography (ethyl acetate/hexane, 1:4) as an off-white solid: mp 99°–102° C.; $^1$H NMR (CDCl$_3$): 1.05 (3H, t, J=7.3 Hz, CH$_3$), 1.29 (3H, s, CH$_3$), 1.32 (3H, s, CH$_3$), 1.39 (3H, d, J=6.8 Hz, CH$_3$), 1.55 (6H, s, 2 CH$_3$), 1.67 (2H, sextet, J=7.7 Hz, CH$_2$), 2.91 (2H, t, J=7.7 Hz, CH$_2$), 3.52 (1H, broad-s, OH), 4.03 (1H, q, J=6.8 Hz, CH), 5.60 (1H, d, J=9.9 Hz, H$_7$), 6.03 (1H, s, H$_3$), 6.73 (1H, d, J=10.1 Hz, H$_8$), 13.81 (1H, s, OH); EIMS: 401 (5.1, M+1), 400 (21.5, M$^+$), 385 (6.2, M-CH$_3$), 342 (38.9, M-C$_3$H$_7$O+1), 327 (100, M-CH$_3$-C$_3$H$_7$O+1); IR (KBr) cm$^{-1}$: 3547 (w, OH), 3449 (vw, broad, OH), 1734 (vs, C=O); Anal. calcd. for C$_{23}$H$_{28}$O$_6$: C, 68.97; H, 7.04. Found. C, 68.98; H, 7.04.

EXAMPLE 25

(±)-syn and (±)-anti-6,6-Dimethyl-9-hydroxy-10-(2-methyl-3-hydroxypentanoyl)-4-propyl-2H,6H-benzo[1,2-b:3,4-b']dipyran-2-one (Scheme V, 14c, R$_1$=n-Pr, R$_2$=R$_3$=R$_7$=R$_8$=H, R$_4$=R$_5$=R$_6$=Me, R$_9$=Et)

To a solution of 4 (1.75 g, 5.11 mmol) in THF (27.0 mL) at −78° C. was added dropwise a solution of LDA in heptane/THF/ethyl benzene (2M, 7.0 mL, 14.0 mmol) under N$_2$. The solution was stirred at −78° C. for 1 h, and propionaldehyde (2.2 mL, 31.2 mmol) was added quickly via syringe. The solution was stirred at −78° C. for 3 h, quenched with methanolic HCl (2M, 25 mL) at −78° C., then warmed to room temperature. The mixture was extracted with ethyl acetate (350 mL), washed sequentially with 150 mL each of saturated NaHCO$_3$ and saturated brine, dried over magnesium sulfate, filtered and concentrated to provide a diastereomeric mixture of the product as a red oil (2.44 g, 100%), which was not further purified and used for the next step.

EXAMPLE 26

(±)-10,11-Dihydro-6,6,10,11,11-pentamethyl-4-propyl-2H,6H,12H-benzo[1,2-b:3,4-b':5,6-b"]tripyran-2,12-dione (Scheme V, 15a, R$_1$=n-Pr, R$_2$=R$_7$=R$_8$=H, R$_3$=R$_4$=R$_5$R$_6$=R$_9$=Me)

To a solution of 14a (0.5 g, 1.25 mmol) and triphenylphosphine (492 mg, 1.88 mmol) in THF (10 mL) was added a solution of diethyl azodicarboxylate (327 mg, 1.88 mmol) in THF (2 mL) dropwise under N$_2$. The reaction mixture was stirred for 2.5 h, after which it was poured into saturated NH$_4$Cl (100 mL). The solution was extracted with ethyl acetate (100 mL), and the separated organic layer washed sequentially with H$_2$O (100 mL) and saturated brine (100 mL). After drying over magnesium sulfate, the solution was filtered and concentrated in vacuo to provide a yellow oil. Column chromatography through 75 g silica gel (ethyl acetate/hexane, 1:2) provided the desired product as a white crystalline solid (449 mg, 94.0%). An analytical sample was obtained via recrystallization from ethyl acetate/hexane (2:1): mp 157° C.; $^1$H NMR (CDCl$_3$): 1.03 (3H, t, J=7.3 Hz, CH$_3$), 1.09 (3H, s, CH$_3$), 1.19 (3H, s, CH$_3$), 1.43 (3H, d, J=6.5 Hz, CH$_3$), 1.53 (3H, s, CH$_3$), 1.55 (3H, s, CH$_3$), 1.64 (2H, sextet, J=7.7 Hz, CH$_2$), 2.88 (2H, t, J=7.7 Hz, CH$_2$), 4.34 (1H, q, J=6.4 Hz, H$_{10}$), 5.60 (1H, d, J=10.0 Hz, H$_7$), 6.04 (1H, s, H$_3$), 6.66 (1H, d, J=10.0 Hz, H$_8$); EIMS: 382 (60.8, M$^+$), 367 (100, M-CH$_3$), 312 (50.3 (M-C$_5$H$_{10}$), 297 (74.5, M-CH$_3$-C$_5$H$_{10}$); IR (KBr) cm$^{-1}$: 1730 (vs, C=O); Anal. calcd. for C$_{23}$H$_{26}$O$_5$: C, 72.23; H, 6.85. Found: C, 72.35; H, 6.90.

EXAMPLE 27

(±)-10,11-Dihydro-6,6,10,10,11-pentamethyl-4-propyl-2H, 6H, 12H-benzo[1,2-b:3,4-b':5,6-b"]tripyran-2,12-dione (Scheme V, 15b, R$_1$=n-Pr, R$_2$=R$_3$=R$_7$=H, R$_4$=R$_5$=R$_6$R$_8$=R$_9$=Me)

To a solution of crude 14b (980 mg, 2.19 mmol) and triphenylphosphine (859.0 mg, 3.28 mmol) in THF (15 mL) was slowly added diethyl azodicarboxylate (DEAD, 0.50 mL, 3.17 mmol) under N$_2$. The red solution was stirred for 2.5 h at room temperature, then quenched with saturated NH$_4$Cl (10 mL). The solution was extracted with ethyl acetate (200 mL), washed sequentially with 50 mL each of H$_2$0 and saturated brine, dried over magnesium sulfate, filtered and concentrated to provide a yellow residue (2.37 g). Purification by silica gel column chromatography (ethyl acetate/hexane, 1:10) provided, after overnight drying under high vacuum in the presence of P$_2$O$_5$, the desired product as an off-white solid (373.7 mg, 44.6%): mp 140°–141° C.; $^1$H NMR (CDCl$_3$): 1.03 (3H, t, J=7.3 Hz, CH$_3$), 1.19 (3H, d, J=7.0 Hz, CH$_3$), 1.34 (3H, s, CH$_3$), 1.53 (6H, s, 2 CH$_3$), 1.55 (3H, s, CH$_3$), 1.65 (2H, sextet, J=7.8 Hz, CH$_2$), 2.72 (1H, q, J=7.0 Hz, H$_{11}$), 2.85–2.91 (2H, m, CH$_2$), 5.60 (1H, d, J=10.1 Hz, H$_7$), 6.03 (1H, s, H$_3$), 6.65 (1H, d, J=10.0 Hz, H$_8$); EIMS: 382 (61.2, M$^+$), 367 (82.0, M-CH$_3$), 312 (46.0, M-C$_5$H$_{10}$), 297 (100, M-CH$_3$-C$_5$H$_{10}$); IR (KBr) cm$^{-1}$: 1728 (vs, C=O); Anal. calcd. for C$_{23}$H$_{26}$O$_5$: C, 72.23; H, 6.85. Found: C, 71.95; H, 6.88.

EXAMPLE 28

(±)-10,11-trans-10,11-Dihydro-10-ethyl-4-propyl-6,6,11-trimethyl-2H, 6H, 12H-benzo[1,2-b:3, 4-b"]tripyran-2,12 -dione (15c) and (±)-10,11-cis-10,11-dihydro-10-ethyl-4-propyl-6, 6, 11-trimethyl-2H,6H, 12H-benzo[1,2-b:3,4-b':5,6-b"]tripyran-2,12-dione (15d, Scheme V)

To a solution of 14c (2.44 g, 5.11 mmol) and triphenylphosphine (1.96 mg, 7.48 mmol) in THF (30.0 mL) was slowly added diethyl azodicarboxylate (DEAD, 1.16 mL, 7.37 mmol) under $N_2$. The red solution was stirred for 2.5 h at room temperature, then quenched with saturated $NH_4Cl$ (22 mL). The solution was warmed to room temperature and extracted with ethyl acetate (400 mL), washed with $H_2O$ (100 mL) and brine (100 mL) and dried over magnesium sulfate. After filtration, the solution was concentrated in vacuo to provide a yellow residue (5.75 g). The crude product was purified by repetitive silica gel column chromatography (3×) using ethyl acetate/hexane (1:4.5) as eluent. The desired fractions were combined, concentrated in vacuo and dried under high vacuum overnight in the presence of $P_2O_5$ to afford 15c (765.4 mg, 39.2%) and 15d (350.4 mg, 17.9%).

15c ($R_1$=n-Pr, $R_2$=$R_4$=$R_7$=$R_8$=H, $R_3$=$R_5$=$R_6$=Me, $R_9$=Et): mp 155°–158° C.; $^1$H NMR (CDCl$_3$): 1.03 (3H, t, J=7.4 Hz, CH$_3$), 1.13 (3H, t, J=7.4 Hz, CH$_3$), 1.22 (3H, d, J=6.9 Hz, CH$_3$), 1.53 (3H, s, CH$_3$), 1.56 (3H, s, CH$_3$), 1.64 (2H, sextet, J=7.6 Hz, CH$_2$), 1.78–1.95 (2H, m, CH$_2$), 2.62 (1H, dq, J=10.4 Hz, J=7.0 Hz, H$_{11}$), 2.88 (2H, t, J=7.7 Hz,CH$_2$), 4.14 (1H, ddd, J=3.5 Hz, J=7.8 Hz, J=10.7 Hz, H$_{10}$), 5.61 (1H, d, J=10.0 Hz, H$_7$), 6.04 (1H, s, H$_3$), 6.66 (1H, d, J=10.0 Hz, H$_8$); EIMS: 382 (37.2, M$^+$), 367 (100, M-CH$_3$), 297 (47.2, M-CH$_3$-C$_5$H$_{10}$) ; IR (KBr) cm$^{-1}$: 1738 (vs, C=O); Anal. calcd. for C$_{23}$H$_{26}$O$_5$: C, 72.23; H, 6.85. Found: C, 71.75; H, 7.02.

15d ($R_1$=n-Pr, $R_2$=$R_3$=$R_7$$R_8$=H, $R_4$=$R_5$=$R_6$=Me, $R_9$=Et): mp 100°–102° C.; $^1$H NMR (CDCl$_3$): 1.03 (3H, t, J=7.3 Hz, CH$_3$), 1.07 (3H, t, J=7.4 Hz, CH$_3$), 1.14 (3H, d, J=7.3 Hz, CH$_3$), 1.54 (3H, s, CH$_3$), 1.55 (3H, CH$_3$), 1.65 (2H, sextet, J=7.6 Hz, CH$_2$), 1.83–1.98 (2H, m, CH$_2$), 2.70 (1H, dq, J=3.2 Hz, J=7.3 Hz, H$_{11}$), 2.88 (2H, t, J=7.6 Hz, CH$_2$), 4.39 (1H, ddd, J=3.4 Hz, J=5.3 Hz, J=8.8 Hz, H$_{10}$), 5.60 (1H, d, J=10.0 Hz, H$_7$), 6.05 (1H, s, H$_3$), 6.66 (1H, d, J=10.0 Hz, H$_8$); EIMS: 382 (55.0, M$^+$), 367 (100, M-CH$_3$), 297 (52.7, M-CH$_3$-C$_5$H,O); IR (KBr) cm$^{-1}$: 1732 (vs, C=O); Anal. calcd. for C$_{23}$H$_{26}$O$_5$. C, 72.23; H, 6.85. Found: C, 71.80; H, 6.97.

EXAMPLE 29

(±)-10,12-cis-10,11-Dihydro-12-hydroxy-6,6,10,11, 11-pentamethyl-4-propyl-2H, 6H, 12H-benzo[1,2-b:3,4-b':5,6-b"]tripyran-2-one (16a) and (±)-10,12-trans-10,11-dihydro-12-hydroxy-6,6,10,11,11-pentamethyl-4-propyl-2H,6H,12H-benzo[1,2-b:3,4-b':5,6-b"]tripyran-2-one (16b, Scheme V)

To a solution of 15a (252 mg, 0.661 mmol) in ethanol/THF (1:1, 8 mL) was added sodium borohydride (25.1 mg, 0.661 mmol) and the solution stirred at room temperature for 30 minutes. The reaction was quenched by the addition of water (1 mL), and the solvent then removed in vacuo. The residue was partitioned between 20 mL each of ethyl acetate and 1M HCl, and the organic phase separated and washed sequentially with 5% NaHCO$_3$ and saturated brine. After drying over magnesium sulfate, the solution was evaporated to give the product as a pale-yellow foam. TLC analysis (ethyl acetate/hexane, 1:2) showed the two epimeric alcohols 16a and 16b at R$_f$ 0.30 and 0.25, as well as a minor impurity at R$_f$ 0.55. Separation via column chromatography (75 g silica gel, ethyl acetate/hexane, 1:2) provided 16a (127.7 mg, 50.3%) and 16b (18.8 mg, 7.4%) as a white foam and an off-white waxy solid, respectively.

16a (R$_1$=n-Pr, R$_2$=R$_7$=R$_8$=H, R$_3$=R$_4$=R$_5$=R$_6$=R$_9$=Me): $^1$H NMR (CDCl$_3$): 1.04 (3H, t, J=7.3 Hz, CH$_3$), 1.06 (6H, s, 2 CH$_3$), 1.40 (3H, d, J=6.7 Hz, CH$_3$), 1.47 (3H, s, CH$_3$), 1.50 (3H, s, CH$_3$), 1.66 (2H, sextet, J=7.3 Hz, CH$_2$), 2.80–2.99 (2H, m, CH$_2$), 3.39 (1H, d, J=3.2 Hz, OH), 3.99 (1H, q, J=6.7 Hz, H$_{10}$), 4.70 (1H, d, J=3.2 Hz, H$_{12}$), 5.54 (1H, d, J=9.9 Hz, H$_7$), 5.94 (1H, s, H$_3$), 6.63 (1H, d, J=9.9 Hz, H$_8$); EIMS: 384 (59.0, M$^+$), 369 (100, M-CH$_3$), 314 (44.7, M-C$_5$H$_{10}$), 299 (88.8, M-CH$_3$-C$_5$H$_{10}$); IR (KBr) cm$^{-1}$: 3432 (broad-s, OH), 1734 (vs, C=O); Anal. calcd. for C$_{23}$H$_{28}$O$_5$: C, 71.85; H, 7.34. Found: C, 71.74; H, 7.43.

16b (R,=n-Pr, R$_2$=R$_7$=R$_8$=H, R$_3$=R$_4$=R$_5$=R$_6$=R$_9$=Me): $^1$H NMR (CDCl$_3$): 0.78 (3H, s, CH$_3$), 1.04 (3H, t, J=7.3 Hz, CH$_3$), 1.11 (3H, s, CH$_3$), 1.36 (3H, d, J=6.5 Hz, CH$_3$), 1.49 (6H, s, 2 CH$_3$), 1.64 (2H, m, CH$_2$), 2.47 (1H, broad-s, OH), 2.89 (2H, m, CH$_2$), 4.35 (1H, q, J=6.5 Hz, H$_{10}$), 4.63 (1H, broad-s, H$_{12}$), 5.54 (1H, d, J=9.8 Hz, H$_7$), 5.96 (1H, s, H$_3$), 6.65 (1H, d, J=9.8 Hz, H$_8$); EIMS: 384 (40.7, M$^+$), 369 (100, M-CH$_3$), 314 (13.5, M-C$_5$H$_{10}$), 299 (48.4, M-CH$_3$-C$_5$H$_{10}$); Anal. calcd. for C$_{23}$H$_{28}$O$_5$: C, 71.85; H, 7.34. Found: C, 71.79; H, 7.49.

EXAMPLE 30

(±)-11,12-cis-10,11-Dihydro-12-hydroxy-6,6,10,10, 11-pentamethyl-4-propyl-2H, 6H, 12H-benzo[1,2-b:3,4-b':5,6-b"]tripyran-2-one (16c) and (+)-11,12-trans-10,11-dihydro-12-hydroxy-6,6,10,10,11-pentamethyl-4-propyl-2H, 6H, 12H-benzo [1,2-b:3,4-b':5,6-b"]tripyran-2-one (16d, Scheme V)

To a solution of 15b (289.7 mg, 0.75 mmol), triphenylphosphine oxide (927.0 mg, 3.33 mmol) and CeCl$_3$ (H$_2$O)$_7$ (842.0 mg, 2.25 mmol) in ethanol (15 mL) at 0° C. was slowly added NaBH$_4$ (195.0 mg, 5.15 mmol) under N$_2$. The suspension was stirred for 1 h at room temperature, then quenched with saturated NH$_4$Cl (30 mL). The solution was extracted with ethyl acetate (200 mL), washed with brine (50 mL), dried over magnesium sulfate, filtered and concentrated to afford a pink crystalline solid (1.38 g). Silica gel column chromatography (ethyl acetate/hexane, 1:5) provided 16c (100.0 mg, 34.3%) as off-white foam and 16d which was further purified by preparative TLC (silica gel, diethyl ether/hexane, 2:1) as off-white foam (56.0 mg, 19.2%).

16c (R$_1$=n-Pr, R$_2$=R$_3$=R$_7$=H, R$_4$=R$_4$=R$_6$=R$_8$=R$_9$=Me): mp 44°–45° C.; $^1$H NMR (CDCl$_3$): 1.04 (3H, t, J=7.3 Hz, CH$_3$), 1.24 (3H, d, J=7.1 Hz, CH$_3$), 1.38 (3H, s, CH$_3$), 1.45 (3H, s, CH$_3$), 1.47 (3H, s, CH$_3$), 1.51 (3H, s, CH$_3$), 1.66 (2H, sextet, J=7.3 Hz, CH$_2$), 1.96–2.04 (1H, m, H$_{11}$), 2.8–3.0 (2H, m, CH$_2$), 3.02 (1H, d, J=4.0 Hz, OH), 4.94 (1H, t, J=4.2 Hz, H$_{12}$), 5.53 (1H, d, J=10.0 Hz, H$_7$), 5.94 (1H, s, H$_3$), 6.65 (1H, d, J=9.9 Hz, H$_8$); EIMS: 385 (22.1, M+1), 384 (61.8, M$^+$), 369 (71.1, M-CH$_3$), 351 (29.5, M-CH$_3$-H$_2$O), 299 (100, M-CH$_3$-C$_5$H$_{10}$); IR (KBr) cm$^{-1}$: 3451 (broad-m, OH), 1709 (s, C=O); Anal. calcd. for C$_{23}$H$_{28}$O$_5$: C, 71.85; H, 7.33. Found: C, 71.63; H, 7.64.

16d (R$_1$=n-Pr, R$_2$=R$_4$=R$_7$=H, R$_3$=R$_5$=R$_6$=R$_8$=R$_9$=Me): mp 40°–42° C.; $^1$H NMR (CDCl$_3$): 1.04 (3H, t, J=7.3 Hz, CH$_3$), 1.13 (3H, d, J=7.0 Hz, CH$_3$), 1.21 (3H, s, CH$_3$), 1.46 (3H, s, CH$_3$), 1.48 (3H, s, CH$_3$), 1.52 (3H, s, CH$_3$), 1.67 (2H, sextet, J=7.6 Hz, CH$_2$), 2.03 (1H, quintet, J=7.2 Hz, H$_{11}$), 2.8–3.0 (2H, m, CH$_2$), 3.66 (1H, s, OH), 4.69 (1H, d, J=7.4 Hz, H$_{12}$), 5.54 (1H, d, J=10.0 Hz, H$_7$), 5.94 (1H, s, H$_3$), 6.63 (1H, d, J=9.9 Hz, H$_8$); EIMS: 385 (8.7, M+1), 384 (36.0, M$^+$), 369 (65.8, M-CH$_3$), 351 (17.6, M-CH$_3$-H$_2$O), 299 (100, M-CH$_3$-C$_5$H$_{10}$); IR (KBr) cm$^{-1}$: 3437 (w, OH), 1734 (s, C=O); Anal. calcd. for C$_{23}$H$_{28}$O$_5$: C, 71.85; H, 7.33. Found: C, 71.70; H, 7.56.

EXAMPLE 31

(±)-10,11-trans,11,12-cis-10,11-Dihydro-10-ethyl-
12-hydroxy-4-propyl-6,6,11-trimethyl-2H,6H,12H-
benzo[1,2-b:3,4-b':5,6-b"]tripyran-2-one (16e) and
(±)-10,11-trans-11,12-trans-10,11-dihydro-10-ethyl-
12-hydroxy-4-propyl-6,6,11-trimethyl-2H,6H,12H-
benzo[1,2-b:3,4-b':5,6-b"]tripyran-2-one (16f,
Scheme V)

To a suspension of 15c (454.7 mg, 1.19 mmol), triphenylphosphine oxide (1.38 g, 4.96 mmol) and $CeCl_3(H_2O)_7$ (1.21 g, 3.25 mmol) in ethanol (10 mL) at 0° C. was slowly added $NaBH_4$ (312.0 mg, 8.25 mmol) under $N_2$. The suspenion was stirred for 3 h at room temperature. The reaction mixture was quenched with saturated $NH_4Cl$ (15 mL), extracted with ethyl acetate (100 mL×3), washed with brine (50 mL), dried over magnesium sulfate, filtered and concentrated to provide pink crystals (1.97 g). Silica gel column chromatography (ethyl acetate/hexane, 1:4) afforded a yellow oil, which consisted of mixture of 16e and 16f (261.0 mg). The compounds were separated using preparative HPLC (normal phase, ethyl acetate/hexane, 3:7). The desired fractions were combined and concentrated in vacuo and dried overnight under high vacuum in the presence of $P_2O_5$ to afford 16e (yellow oil, 46.5 mg, 10.1%) and 16f (white solid, 137.6 mg, 30.1%).

16e ($R_1$=n-Pr, $R_2$=$R_4$=$R_7$=$R_8$=H, $R_3$=$R_5$=$R_6$=Me, $R_9$=Et): $^1$H NMR ($CDCl_3$): 1.03 (3H, t, J=7.3 Hz, $CH_3$), 1.10 (3H, t, J=7.6 Hz, $CH_3$), 1.13 (3H, d, J=6.8 Hz, $CH_3$), 1.48 (3H, s, $CH_3$), 1.49 (3H, s, $CH_3$), 1.65 (2H, sextet, J=7.4 Hz, $CH_2$), 1.76–1.98 (3H, m, $CH_2$+$H_{11}$), 2.80–2.92 (3H, m, $CH_2$+OH), 4.10 (1H, dd, J=2.9 Hz, J=7.9 Hz, J=10.7 Hz, $H_{10}$), 4.98 (1H, d, J=3.3 Hz, $H_{12}$), 5.54 (1H, d, J=9.9 Hz, $H_7$), 5.94 (1H, s, $H_3$), 6.63 (1H, d, J=9.9 Hz, $H_8$); EIMS: 385(10.5, M+1), 384 (35.8, M$^+$), 369 (78.4, M-$CH_3$), 366 (43.1, M-$H_2O$), 351 (39.0, M-$CH_3$-$H_2O$), 337 (100, M-$H_2O$-$C_2H_5$), 299 (37.7, M-$CH_3$-$C_5H_{10}$); IR (neat, thin film) cm$^{-1}$: 3432 (w, OH), 1709 (s, C=O); Anal. calcd. for $C_{23}H_{28}O_5$·¼ $H_2O$: C, 71.02; H, 7.38. Found: C, 71.10; H, 7.40.

16f ($R_1$=n-Pr, $R_2$=$R_4$=$R_7$$R_8$=H, $R_3$=$R_5$=$R_6$=Me, $R_9$=Et): mp 103°–105° C.; $^1$H NMR ($CDCl_3$): 1.04 (3H, t, J=7.3 Hz, $CH_3$), 1.07 (3H, t, J=7.4 Hz, $CH_3$), 1.13 (3H, d, J=6.9 Hz, $CH_3$), 1.47 (3H, s, $CH_3$), 1.51 (3H, s, $CH_3$), 1.66 (2H, sextet, J=7.6 Hz, $CH_2$), 1.79–1.90 (2H, m, $CH_2$), 2.05 (1H, m, $H_{11}$), 2.90 (2H, m, $CH_2$), 3.53 (1H, s, OH), 3.78 (1H, dt, J=4.1 Hz, J=8.1 Hz, $H_{10}$), 4.73 (1H, d, J=6.7 Hz, $H_{12}$), 5.54 (1H, d, J=10.0 Hz, $H_7$), 5.95 (1H, s, $H_3$), 6.63 (1H, d, J=9.9 Hz, $H_8$); EIMS: 385 (7.6, M+1), 384 (31.1, M$^+$), 369 (100, M-$CH_3$), 351 (9.5, M-$CH_3$-$H_2O$), 337 (11.5, M-$H_2O$-$C_2H_5$), 299 (36.9, M-$CH_3$-$C_5H_{10}$); IR (KBr) cm$^{-1}$: 3493, 3435 and 3250 (w, OH), 1699 (s, C=O); Anal. calcd. for $C_{23}H_{28}O_5$: C, 71.85; H, 7.33. Found: C, 71.46; H, 7.34.

EXAMPLE 32

(±)-10,11-cis-11,12-trans-10,11-Dihydro-10-ethyl-
12-hydroxy-4-propyl-6,6,11-trimethyl-2H,6H,12H-
benzo[1,2-b:3,4-b':5,6-b"]tripyran-2-one (16g) and
(±)-10,11,12-cis-10,11-dihydro-10-ethyl-12-
hydroxy-4-propyl-6,6,11-trimethyl-2H,6H,12H-
benzo[1,2-b:3,4-b':5,6-b"]tripyran-2-one (16h,
Scheme V)

To a solution of 15d (290.5 mg, 0.76 mmol) in ethanol (15 mL) at 25° C. was added $NaBH_4$ (269.0 mg, 7.11 mmol) portionwise under $N_2$. The suspension was stirred for 1 h at room temperature, then quenched with saturated $NH_4Cl$ (6 mL). The solution was extracted with ethyl acetate (200 mL), washed with brine (80 mL), dried over magnesium sulfate, filtered and concentrated to provide a pink residue (455.8 mg). The crude product was purified by silica gel preparative TLC (ethyl acetate/hexane, 2:1). The desired bands were scraped, combined, extracted, concentrated in vacuo and dried under high vacuum overnight in the presence of $P_2O_5$ to afford the desired products 16g (229 mg, 78% yield) with 95% purity as indicated by HPLC) and 16h (55.9 mg, 19% yield) with 92% purity. The analytical samples were obtained by further purification via preparative HPLC (normal phase, ethyl acetate/hexane, 3:7).

16g ($R_1$=n-Pr, $R_2$=$R_3$=$R_7$=$R_8$=H, $R_4$=$R_5$=$R_6$=Me, $R_9$=Et): $^1$H NMR ($CDCl_3$): 1.03 (3H, t, J=7.4 Hz, $CH_3$), 1.04 (3H, t, J=7.3 Hz, $CH_3$), 1.12 (3H, d, J=7.1 Hz, $CH_3$), 1.49 (3H, s, $CH_3$), 1.66 (2H, sextet, J=7.3 Hz, $CH_2$), 1.8–2.0 (2H, m, $CH_2$), 2.3–2.4 (1H, m, $H_{11}$), 2.8–3.0 (2H, m, $CH_2$), 3.30 (1H, s, OH), 4.06 (1H, dt, J=10.1 Hz, J=3.3 Hz, $H_{10}$), 5.10 (1H, d, J=5.2 Hz, $H_{12}$), 5.55 (1H, d, J=10.0 Hz, $H_7$), 5.94 (1H, s, $H_3$), 6.63 (1H, d, J=10.0 Hz, $H_8$); EIMS: 385 (6.3, M+1), 384 (27.3, M$^+$), 369 (100, M-$CH_3$), 351 (6.8, M-$CH_3$-$H_2O$), 337 (4.2, M-$H_2O$-$C_2H_5$), 299 (34.7, M-$CH_3$-$C_5H_{10}$); IR (KBr) cm$^{-1}$: 3449 (m, OH), 1734 (vs, C=O); Anal. calcd. for $C_{23}H_{28}O_5$: C, 71.85; H, 7.33. Found: C, 71.79; H, 7.39.

16h ($R_1$=n-Pr, $R_2$=$R_3$=$R_7$=$R_8$=H, $R_4$=$R_5$=$R_6$=Me, $R_9$=Et): $^1$H NMR ($CDCl_3$): 0.79 (3H, d, J=7.3 Hz, $CH_3$), 1.04 (3H, t, J=7.3 Hz, $CH_3$), 1.11 (3H, t, J=7.3 Hz, $CH_3$), 1.49 (3H, s, $CH_3$), 1.51 (3H, s, $CH_3$), 1.67 (2H, sextet, J=7.4 Hz, $CH_2$), 1.92 (2H, m, $CH_2$), 2.10 (1H, tq, J=2.0 Hz, J=7.3 Hz, $H_{11}$), 2.79 (1H, s, OH), 2.81–2.90 (2H, m, $CH_2$), 4.23 (1H, ddd, J=1.9 Hz, J=5.4 Hz, J=8.7 Hz, $H_{10}$), 4.87 (1H, d, J=1.9 Hz, $H_{12}$), 5.54 (1H, d, J=10.0 Hz, $H_7$), 5.96 (1H, s, $H_3$), 6.66 (1H, d, J=9.9 Hz, $H_8$); EIMS: 385 (6.1, M+1), 384 (26.0, M$^+$), 369 (100, M-$CH_3$), 351 (9.8, M-$CH_3$-$H_2O$), 337 (8.2, M-$H_2O$-$C_2H_5$), 299 (17.6, M-$CH_3$-$C_5H_{10}$); IR (neat, thin film) cm$^{-1}$: 3410 (w, OH), 1732 (s, C=O).

EXAMPLE 33

(±) -10,11-trans-4-Propyl-7,8,10,11-tetrahydro-6,6,
10,11-tetramethyl-2H, 6H, 12H-benzo[1,2-b:3,4-
b':5,6-b"]tripyran-2,12-dione (Scheme VI, 18a, $R_1$=
n-Pr, $R_2$=$R_4$=$R_7$=$R_8$=H, $R_3$=$R_5$=$R_6R_9$=Me)

To a solution of (±)-7 (534 mg, 1.45 mmol) in ethanol/methylene chloride (1:1, 50 mL, Parr apparatus) under $N_2$ was added 10% palladium/carbon (53.4 mg) at ambient temperature. The mixture was shaken under hydrogen (2 atm) for 1 h, then gravity filtered through Whatmann filter paper. The solvent was evaporated to give a white crystalline solid which was filtered through a short plug of silica gel, eluting with methylene chloride/methanol (97:3). The pure compound (±)-18a (441 mg, 82.2%) was obtained as white plates by recrystallization from ethyl acetate: mp 165° C.; $^1$H NMR ($CDCl_3$): 1.01 (3H, t, J=7.3 Hz, $CH_3$), 1.21 (3H, d, J=6.8 Hz, $CH_3$), 1.42 (3H, s, $CH_3$), 1.44 (3H, s, $CH_3$), 1.53 (3H, d, J=6.2 Hz, $CH_3$), 1.61 (2H, sextet, J=7.5 Hz, $CH_2$), 1.84 (2H, apparent dt, J=2.4 Hz, J=6.7 Hz, $CH_2$), 2.53 (1H, dq, J=11.2 Hz, J=6.8 Hz, $H_{11}$), 2.69 (2H, apparent dt, J=3.4 Hz, J=6.7 Hz, $CH_2$), 2.88 (2H, t, J=7.5 Hz, $CH_2$), 4.28 (1H, dq, J=11.2 Hz, J=6.2 Hz, $H_{10}$), 6.02 (1H, s, $H_3$); EIMS: 371 (40.8, M+1); 370 (100, M$^+$), 314 (99.3, M-$C_4H_8$), 299 (21.6, M-$C_5H_{10}$-1), 286 (65.0, M-$CH_3$-$C_5H_{10}$+1), 271 (20.5, M-$CH_3$-$C_5H_8$O), 259 (47.5, M-$C_4H_8$-$C_3H_4$O+1); IR (KBr) cm$^{-1}$: 1740 (vs, C=O); Anal. calcd. for $C_{22}H_{26}O_5$: C, 71.33; H, 7.07. Found: C, 71.00; H, 7.22.

EXAMPLE 34

(±)-10,11-trans-10,11-Dihydro-4-propyl-6,6,10,11-tetramethyl-2H, 6H, 12H-benzo[1,2-b:3,4-b':5,6-b"]tripyran-2,12-dione-12-oxime (Scheme VI, 19a, $R_1$=n-Pr, $R_2$=$R_4$=$R_7$=$R_8$=H, $R_3$=$R_5$=$R_9$=Me, $R_{10}$=H)

Into a 100 mL one-necked round-bottom flask was placed (±)-7 (1.47 g, 4.00 mmol) and $NH_2OH \cdot HCl$ (1.39 g, 20.0 mmol). To this mixture was added methanol (60 mL), and the solution heated to reflux with magnetic stirring until the ketone dissolved. Solid $K_2CO_3$ powder (1.38 g, 10.0 mmol) was then carefully added, and the reaction allowed to stir at reflux for 4 hours. The solution was cooled at room temperature, filtered to remove the $K_2CO_3$ and evaporated in vacuo, to provide a yellow solid. The residue was partitioned between 150 mL each of $H_2O$ and ethyl acetate. The organic phase was collected and washed sequentially with 1N HCl and saturated brine, then dried over magnesium sulfate, filtered and evaporated to afford a thick yellow syrup, which was purified via silica gel column chromatography (75 g), eluting with methylene chloride/methanol (97:3) to afford the desired product as a white solid (657 mg, 43%). An analytical sample was obtained via recrystallization from acetone/hexane (1:3) as colorless prisms; mp 200°–201° C.; $^1$H NMR ($CDCl_3$): 1.04 (3H, t, J=7.4 Hz, $CH_3$), 1.23 (3H, d, J=7.0 Hz, $CH_3$), 1.33 (3H, d, J=6.5 Hz, $CH_3$), 1.51 (3H, s, $CH_3$), 1.54 (3H, s, $CH_3$), 1.67 (2H, sextet, J=7.4 Hz, $CH_2$), 2.82–3.01 (2H, m, $CH_2$), 3.79 (1H, dq, J=2.0 Hz, J=7.0 Hz, $H_{11}$), 4.46 (1H, dq, J=2.0 Hz, J=6.5 Hz, $H_{10}$), 5.57 (1H, d, J=9.9 Hz, $H_7$), 6.02 (1H, s, $H_3$), 6.67 (1H, d, J=9.9 Hz, $H_8$), 9.46 (1H, broad-s, OH); EIMS: 384 (12.9,M+1), 383 (49.22, M$^+$), 368 (100, M-$CH_3$), 366 (21.1, M-OH), 352 (15.2, M-NOH); IR (KBr) cm$^{-1}$: 3223 (broad, OH), 1740 (C=O); Anal. calcd. for $C_{22}H_{25}NO_5 \cdot \frac{1}{4} H_2O$): C, 68.11; H, 6.63; N, 3.61. Found: C, 68.40; H, 6.59; N, 3.58.

EXAMPLE 35

(±)-10,11-trans-10,11-Dihydro-4-propyl-6,6,10,11-tetramethyl-2H, 6H, 12H-benzo[1,2-b:3,4-b':5,6-b"]tripyran-2,12-dione-12-methoxime (Scheme VI, 19b, $R_1$=n-Pr, $R_2$=$R_4$=$R_7$$R_8$=H, $R_3$=$R_5$=$R_6$=$R_9$=Me, $R_{10}$=Me)

Into a one-necked 100 mL round-bottom flask was placed (±)-7 (1.47 g, 4.00 mmol) and $NH_2OCH_3 \cdot HCl$ (1.67 g, 20.0 mmol). To this mixture was added methanol (60 mL), and the solution heated to reflux with magnetic stirring until the ketone dissolved. Solid $K_2CO_3$ powder (1.38 g, 10.0 mmol) was then carefully added, and the reaction allowed to stir at reflux for 4 hours. The solution was cooled to room temperature, filtered to remove the $K_2CO_3$ and evaporated in vacuo, to provide a yellow oil. The residue was partitioned between 150 mL $H_2O$ and 150 mL ethyl acetate. The organic phase was collected and washed sequentially with 1N HCl and saturated brine, then dried over magnesium sulfate, filtered and evaporated to afford a thick yellow syrup. The product was purified via silica gel column chromatography (75 g), eluting with ethyl acetate/hexane (1:3) to afford the desired product as a faintly yellow oil which, upon standing, formed a white solid (598 mg, 38%). An analytical sample was obtained via recrystallization from acetone/hexane (1:3) as white plates; mp 143°–144° C.; $^1$H NMR ($CDCl_3$): 1.01 (3H, t, J=7.3 Hz, $CH_3$), 1.16 (3H, d, J=7.0 Hz, $CH_3$), 1.28 (3H, d, J=6.4 Hz, $CH_3$), 1.49 (3H, s, $CH_3$), 1.50 (3H, s, $CH_3$), 1.64 (2H, sextet, J=7.3 Hz, $CH_2$), 2.79–2.99 (2H, m, $CH_2$), 3.57 (H, dq, J=1.9 Hz, J=7.0 Hz, $H_{11}$), 4.06 (3H, s, $OCH_3$), 4.37 (1H, dq, J=1.9 Hz, J=6.4 Hz, $H_{10}$), 5.54 (1H, d, J=10.0 Hz, $H_7$), 6.00 (1H, s, $H_3$), 6.62 (1H, d, J=10.0 Hz, $H_8$); EIMS: 397 (61.2, M$^+$), 382 (100, M-$CH_3$), 366 (12.9, M-$OCH_3$); IR (KBr) cm$^{-1}$: 1728 (vs, C=O); Anal. calcd. for $C_{23}H_{27}NO_5$: C, 69.50; H, 6.85; N, 3.52. Found: C, 69.39; H, 6.90; N, 3.59.

EXAMPLE 36

Conversion of (−)-Calanolide A into (−)-Calanolide B

To a solution of (−)-calanolide A (341 mg, 0.922 mmol) in anhydrous methylene chloride (5 mL) at −78° C. under $N_2$ was added a solution of diethylamidosulfur trifluoride (DAST, 178 mg, 1.11 mmol) in methylene chloride (1 mL) and the resulting yellow solution stirred at −78° C. for 4 hours. The reaction was quenched with 0.5 mL methanol, then allowed to warm to room temperature. The solution was diluted with methylene chloride (20 mL), then washed with water (50 mL) and saturated brine (50 mL). After drying over magnesium sulfate, the solution was filtered and evaporated to provide a light yellow solid. TLC analysis (silica gel, 3% methanol in methylene chloride) showed two components, one fast-moving and one slow. The material was chromatographed through 80 g silica gel, eluting with 1% methanol in $CH_2Cl_2$, and the fractions containing the respective components combined and evaporated to afford 198 mg (61% yield) of compound 22 and 75.3 mg (22%) of (−)-calanolide B.

10(S)-4-propyl-6,6,10,11-tetramethyl-2H,6H,10H-benzo[1,2-b:3,4-b':5,6-b"]tripyran-2-one (22): $^1$H NMR ($CDCl_3$): 1.03 (3H, t, J=7.4 Hz, $CH_3$), 1.39 (3H, d, J=6.6 Hz, $CH_3$), 1.47 (3H, s, $CH_3$). 1.51 (3H, s, $CH_3$), 1.66 (2H, sextet, J=7.4 Hz, $CH_2$), 1.85 (3H, s, $CH_3$), 2.88 (2H, m, $CH_2$), 4.89 (1H, q, J=6.6 Hz, $H_{10}$), 5.55 (1H, d, J=10.0 Hz, $H_7$), 5.93 (1H, s, $H_3$), 6.62 (1H, d, J=10.0 Hz, $H_8$), 6.64 (1H, s, $H_{12}$); EIMS: 353 (15.5, M+l), 352 (53.2, M$^+$), 337 (100, M-$CH_3$). IR (KBr) cm$^{-1}$: 1724 (s, C=O); Anal. calcd. for $C_{22}H_{24}O_4$: C, 74.98; H, 6.86. Found: C, 74.87; H, 7.00.

10(S),11(R),12 (S)-10,11-Dihydro-12-hydroxy-4-propyl-6,6,10,11-tetramethyl-2H,6H-benzo[1,2-b:3,4-b':5,6-b"]tripyran-2-one [(−)-Calanolide B]: $^1$H NMR ($CDCl_3$): 1.03 (3H, t, J=7.3 Hz, $CH_3$), 1.14 (3H, d, J=7.0 Hz, $CH_3$), 1.43 (3H, d, J=6.4 Hz, $CH_3$), 1.48 (3H, s, $CH_3$), 1.49 (3H, $CH_3$), 1.66 (2H, sextet, J=7.6 Hz, $CH_2$), 1.72–1.79 (1H, m, $H_{11}$), 2.60 (1H, d, J=3.8 Hz, OH), 2.89 (2H, m, $CH_2$), 4.26 (1H, dq, J=10.7 Hz, 6.3 Hz, $H_{10}$), 4.97 (1H, J=3.8 Hz, $H_{12}$), 5.53 (1H, d, J=10.0 Hz, $H_7$), 5.95 (1H, s, $H_3$), 6.63 (1H, d, J=10.0 Hz, $H_8$); EIMS: 370 (31.1, M$^+$), 355 (100, M-$CH_3$), 299 (29.7, M-$CH_3$-$C_4H_8$); IR (KBr) cm$^{-1}$: 3478 (s, sharp, OH), 1703 (s, C=O).

EXAMPLE 37

In Vitro evaluation of (+)-, (±)- and (−)-calanolide A

This example illustrates the anti-HIV viral activity of the synthetic (±) -calanolide A and its pure enantiomers, (+)-calanolide A and (−)-calanolide A, which were evaluated using the published MTT-tetrazolium methods. Retroviral agents AZT and DDC were used as controls for comparison purposes.

Figure 1B:
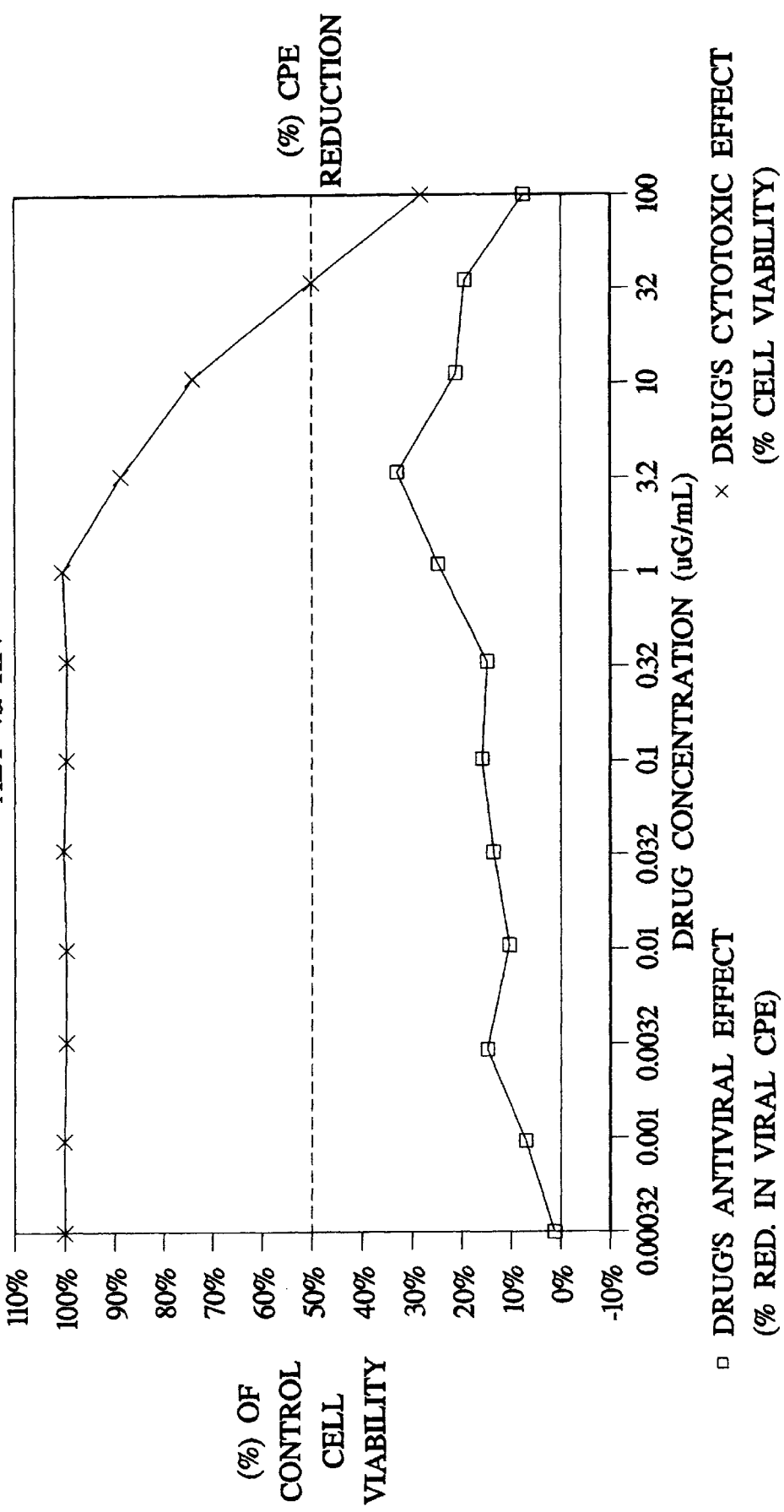
Figure 1C:
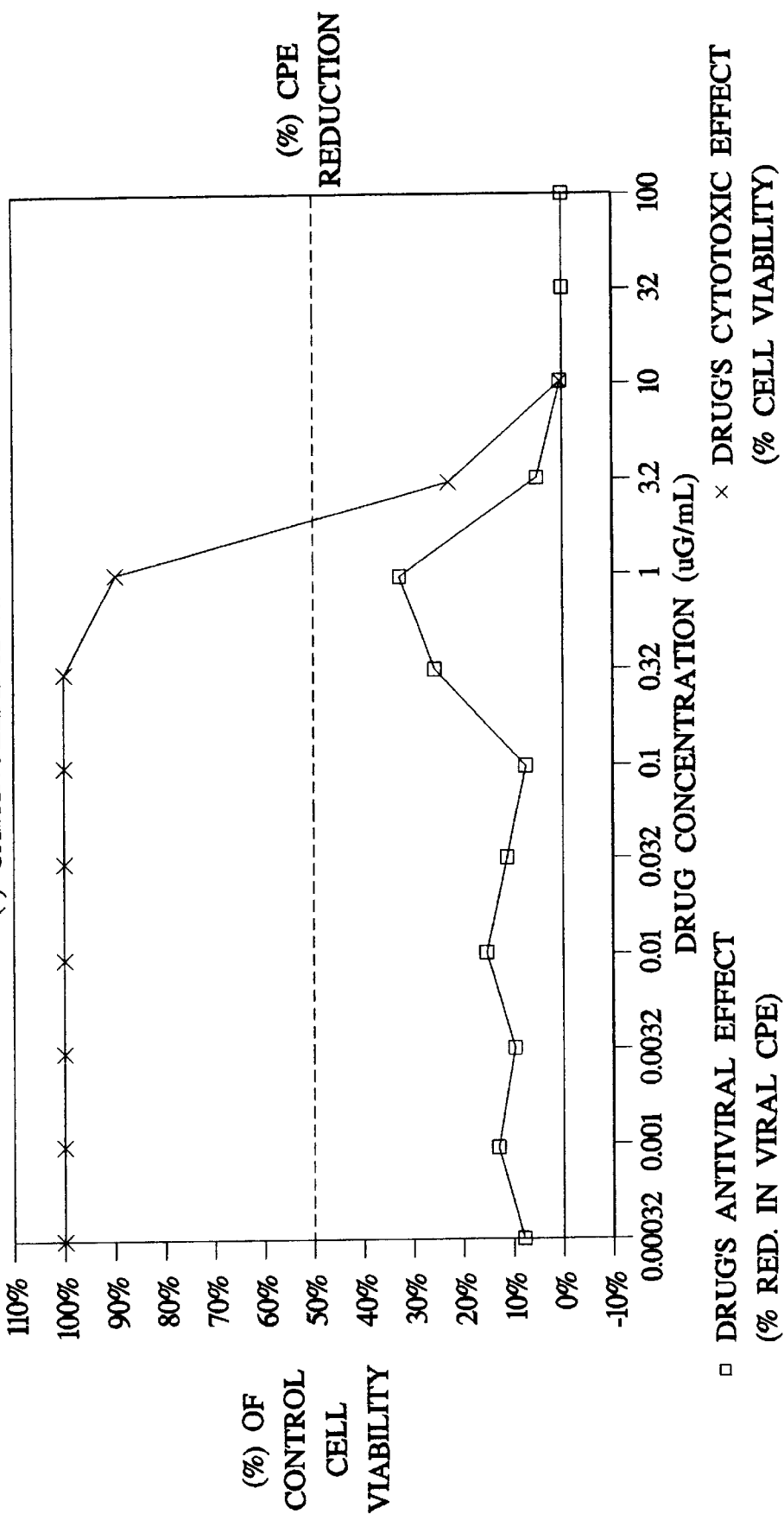
Figure 1E:
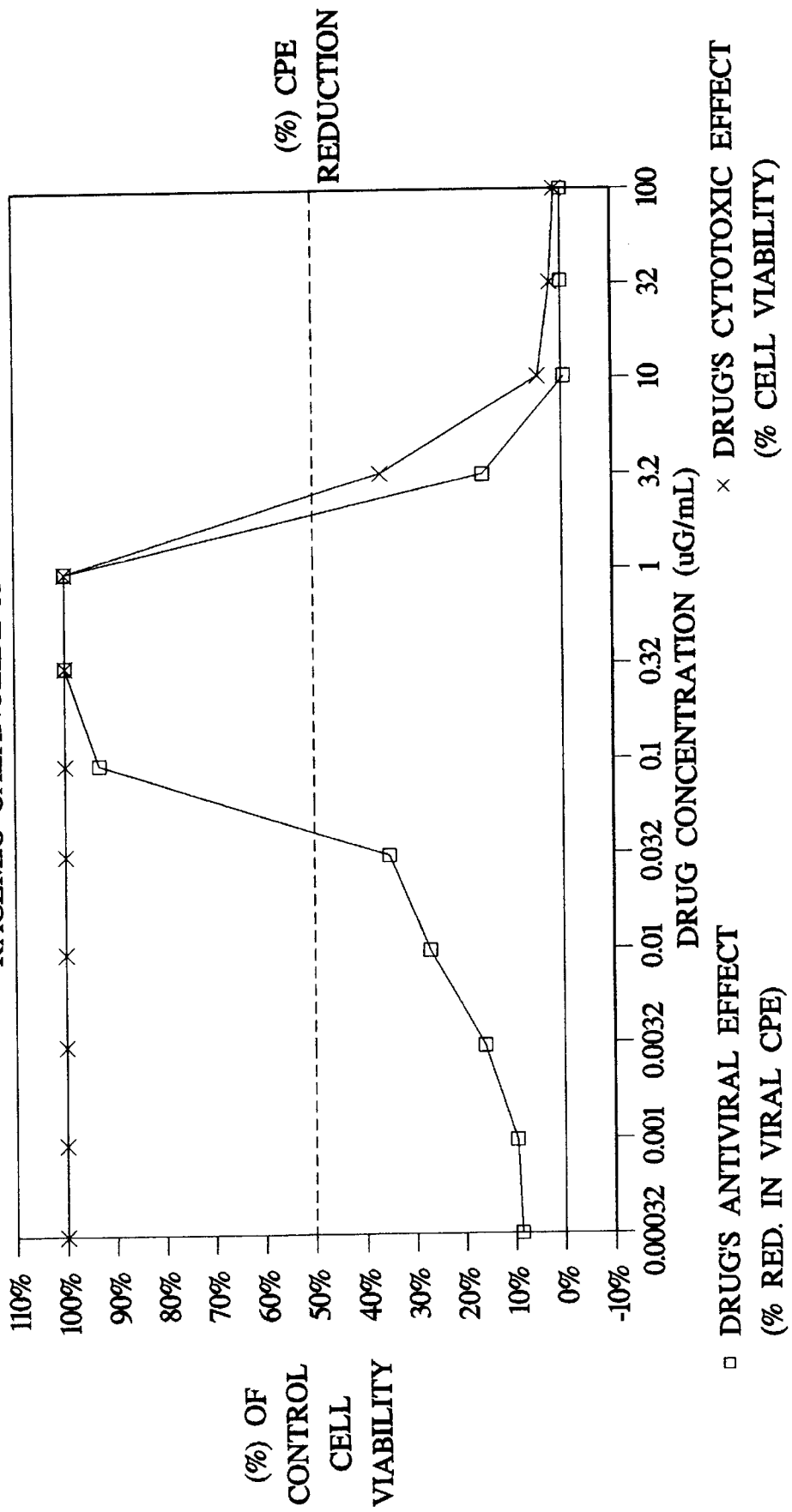

The cells used for screening were the MT-2 and the human T4-lymphoblastoid cell line, CEM-SS, and were grown in RPMI 1640 medium supplemented with 10% fetal (v/v) heat-inactivated fetal calf serum and also containing 100 units/mL penicillin, 100 μg/mL streptomycin, 25 mM HEPES and 20 μg/mL gentamicin. The medium used for dilution of drugs and maintenance of cultures during the assay was the same as above. The HTLV-IIIB and HTLV-RF were propagated in CEM-SS. The appropriate amounts of the pure compounds for anti-HIV evaluations were dissolved in DMSO, then diluted in medium to the desired initial concentration. The concentrations (μg drug/mL medium) employed were 0.0032 μg/mL; 0.001 μg/mL; 0.0032 μg/mL; 0.01 μg/mL; 0.032 μg/mL; 0.1 μg/mL; 0.32 μg/mL; 1 μg/mL; 3.2 μg/mL; 10 μg/mL; 32 μg/mL; and 100 μg/mL. Each dilution was added to plates in the amount of 100 μL/well. Drugs were tested in triplicate wells per dilution with infected cells while in duplicate wells per dilution with uninfected cells for evaluation of cytotoxicity. On day 6 (CEM-SS cells) and day 7 (MT-2 cells) post-infection, the viable cells were measured with a tetrazolium salt, MTT (5 mg/mL), added to the test plates. A solution of 20% SDS in 0.001N HCl is used to dissolve the MTT formazan produced. The optical density value was a function of the amount of formazan produced which was proportional to the number of viable cells. The percent inhibition of CPE per drug concentration was measured as a test over control and expressed in percent (T/C%). The data is summarized in FIGS. 1(a–e), 2(a–e), 3(a–e), 4(a–d), and 5(a–d).

FIGS. 1(a) to 1(e) illustrate in vitro MTT assay results using an isolate, G910-6 HIV viral strain[19], which is AZT-resistant. The data shows that (−)-calanolide A was relatively non-toxic at concentrations of 1 μg/mL but exhibited very little antiviral effect. Moreover, (±)-calanolide A and (+)-calanolide A were effective in reducing viral CPE. As expected, AZT had little to no effect in reducing viral CPE and enhancing cell viability.

Figure 2A:
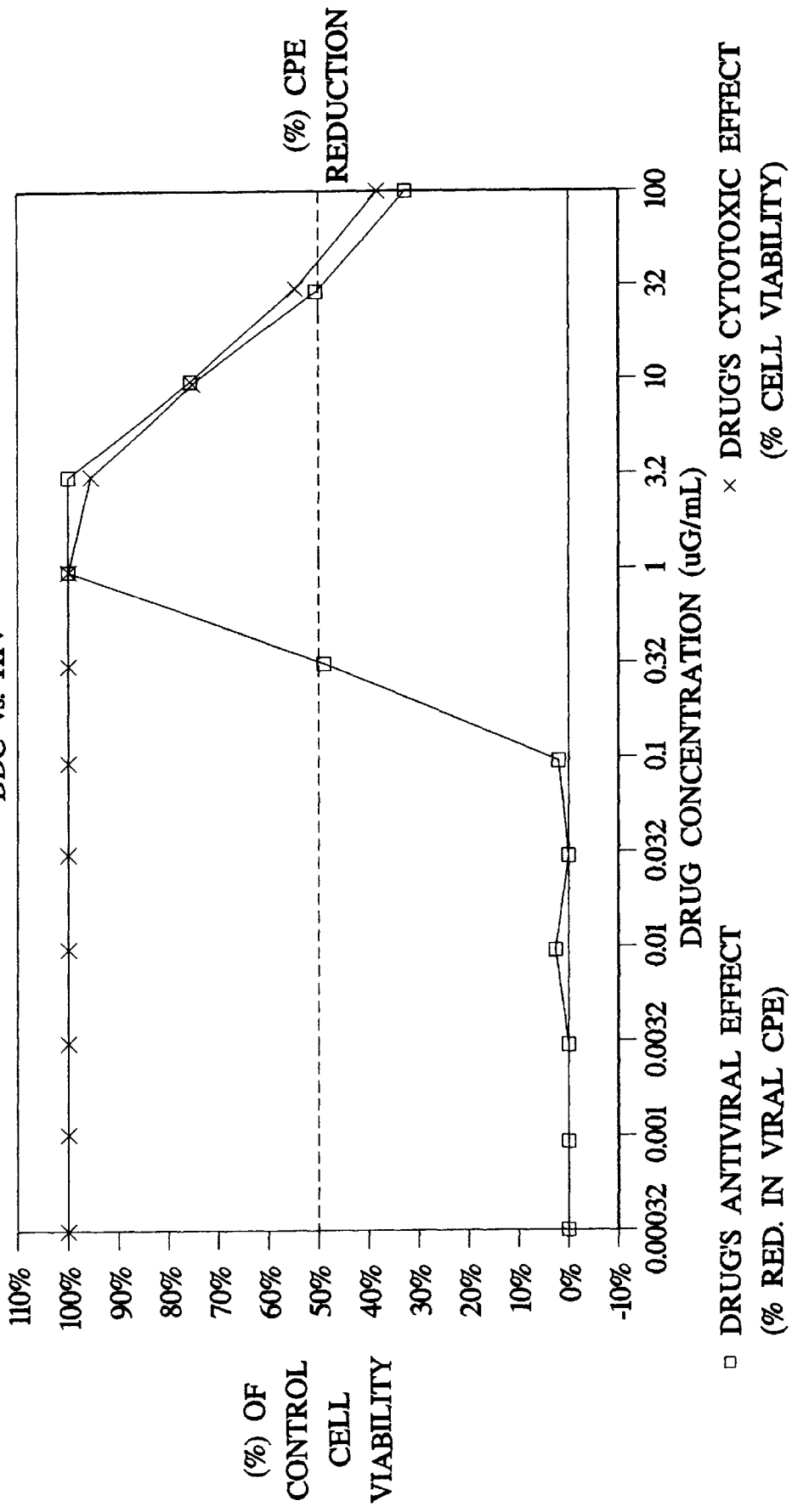
FIGS. 2(a) to 2(e) illustrate in vitro MTT assay results, as described in Example 37, using H112-2 HIV viral strain which was not pre-treated with AZT.
Figure 2B:
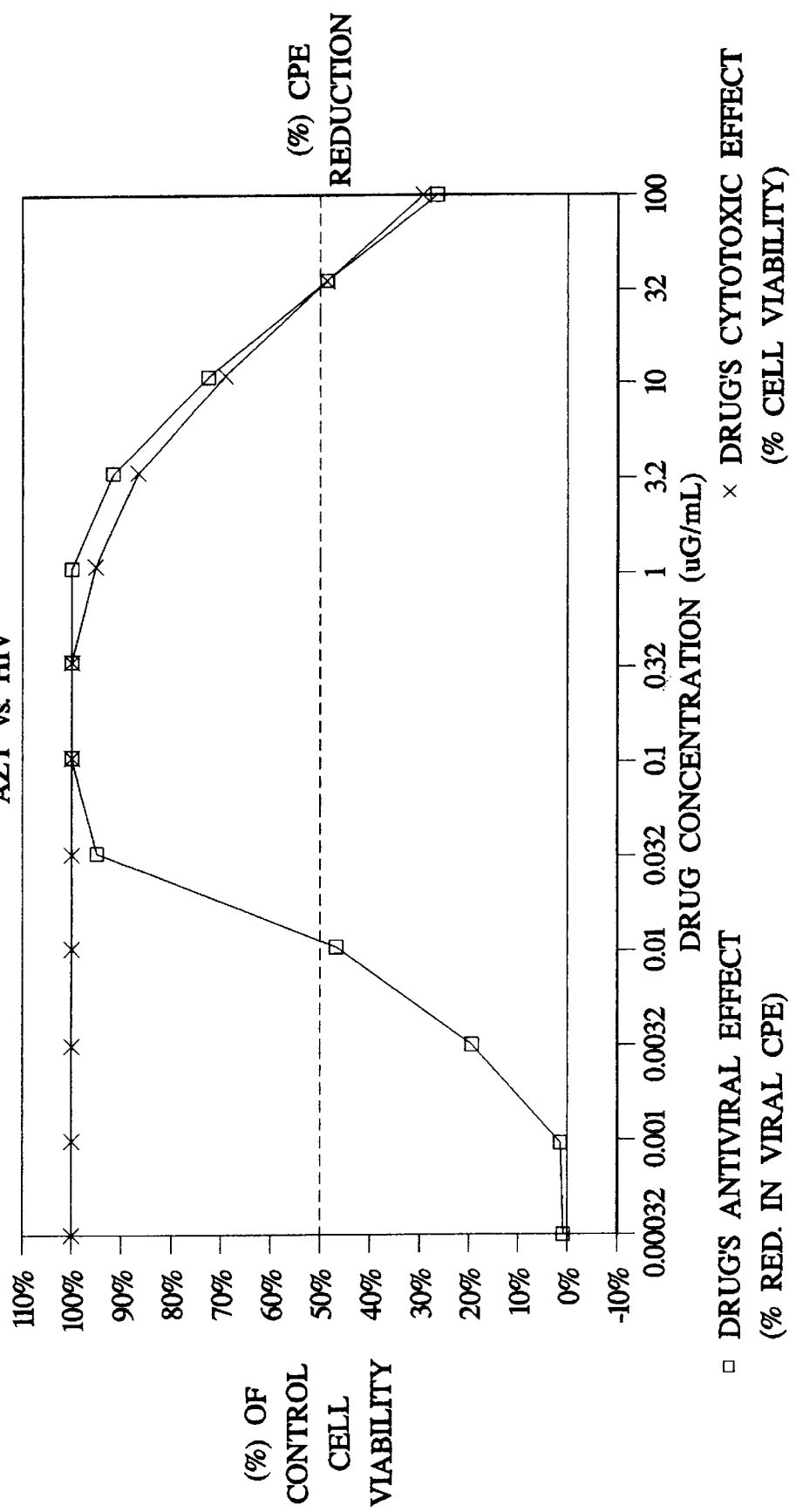
Figure 2C:
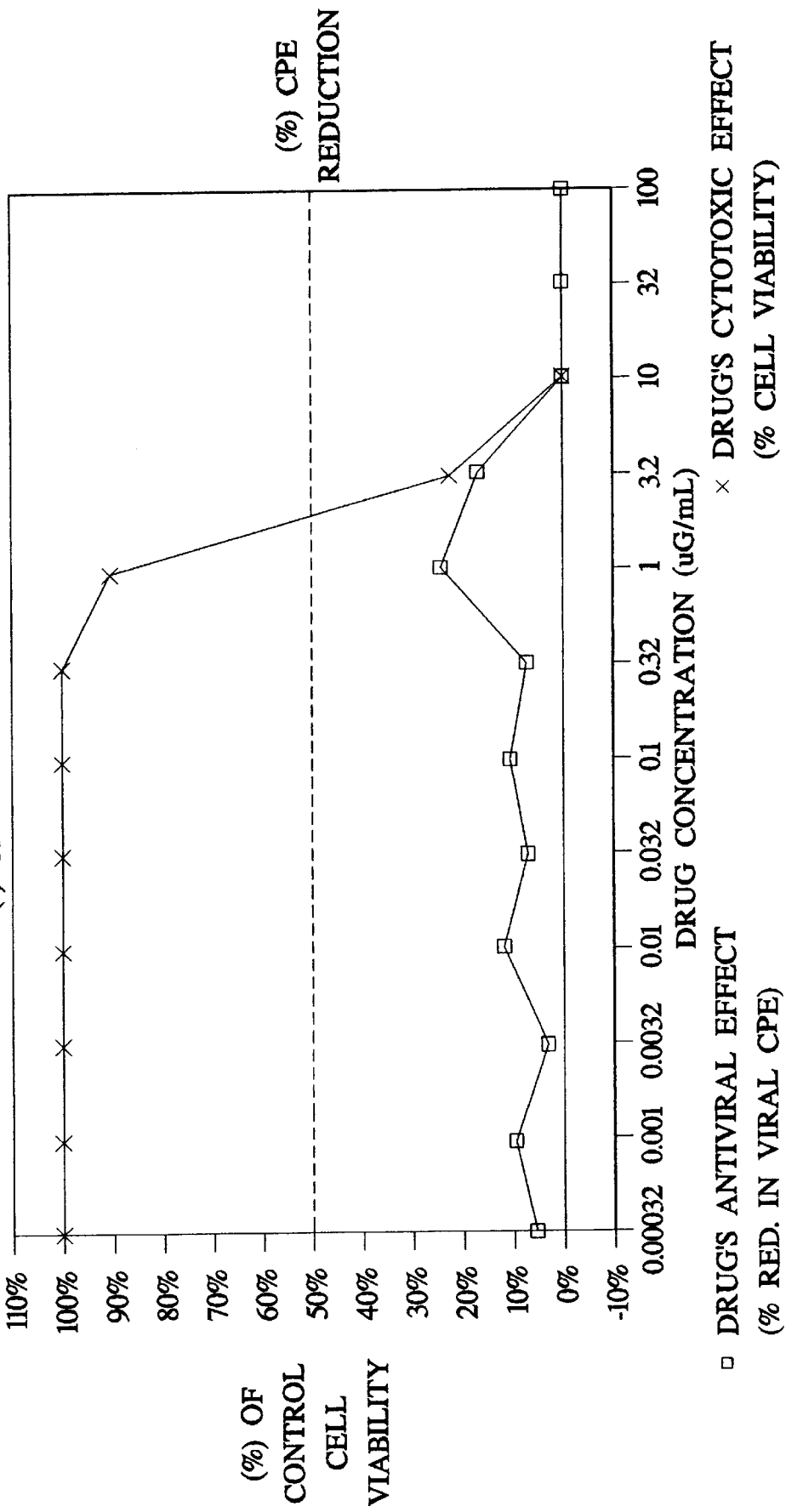
Figure 2D:
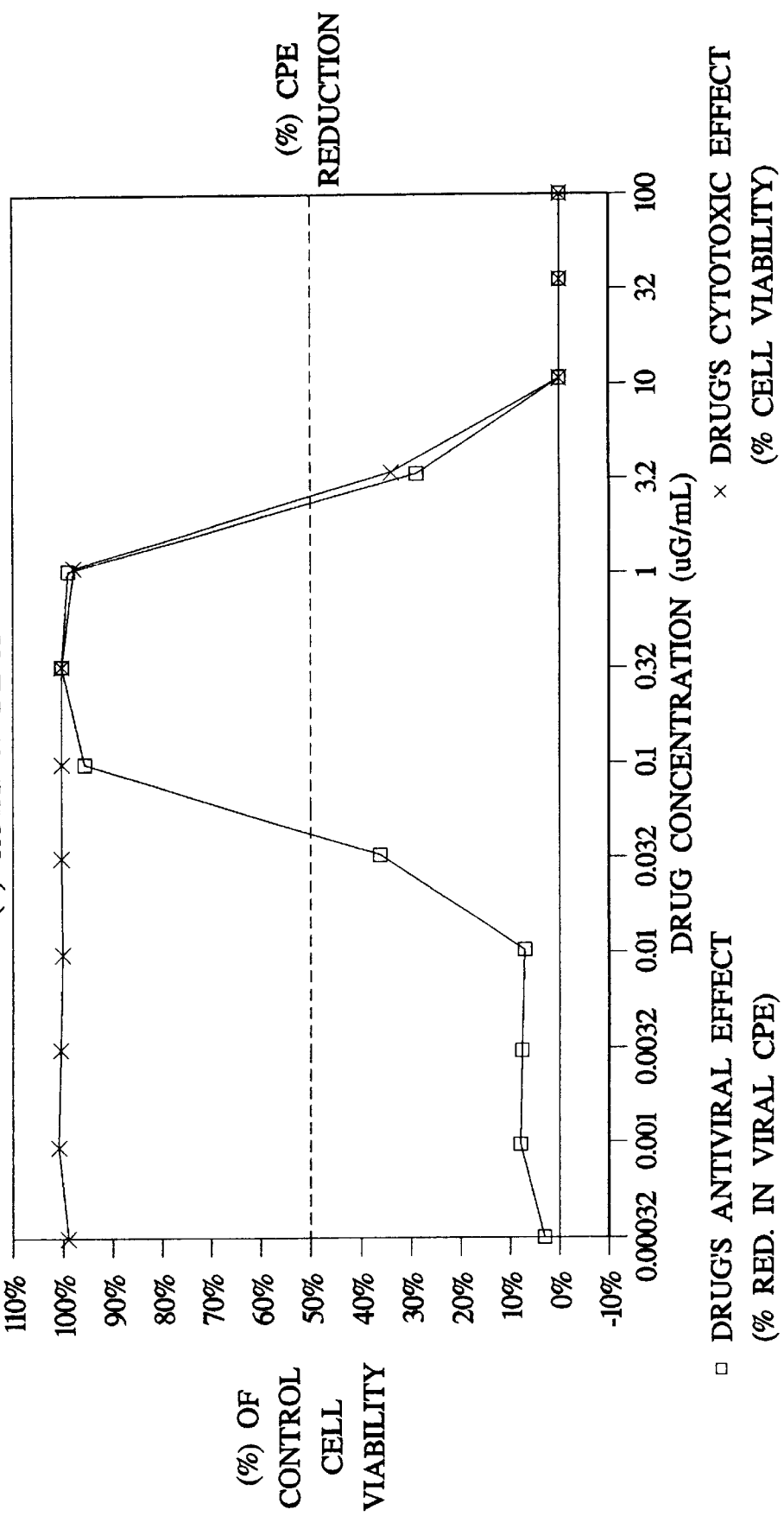
Figure 2E:
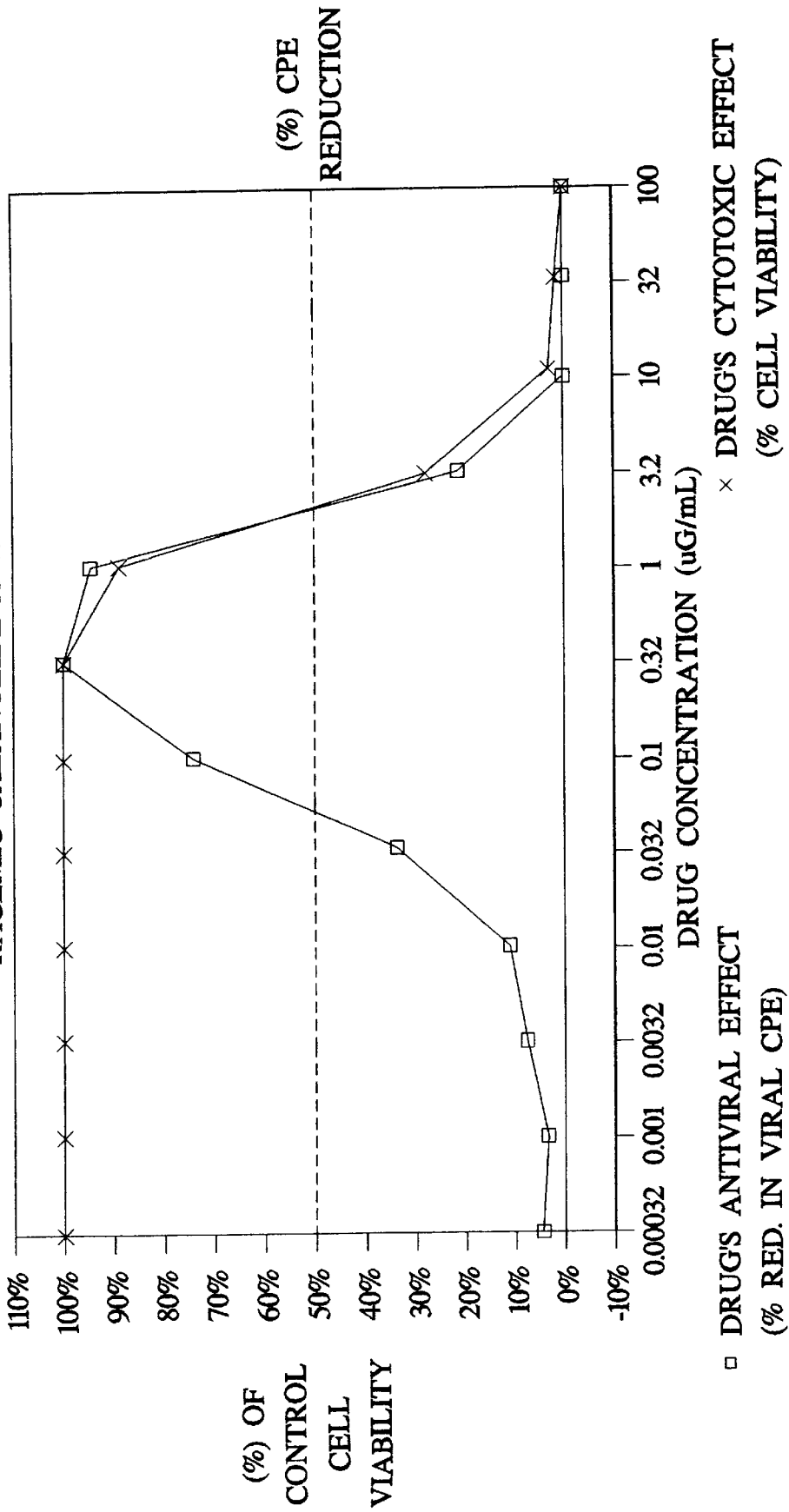

FIGS. 2(a) to 2(e) illustrate in vitro MTT assay results using H112-2 HIV viral strain[19] which was not pre-treated with AZT. As expected, the viral strain was sensitive to AZT. The data also showed that (−)-calanolide A was relatively non-toxic at concentrations of 1 μg/mL but exhibited very little antiviral effect. (±)-Calanolide A was nearly as effective as (+)-calanolide A in reducing viral CPE.

Figure 3A:
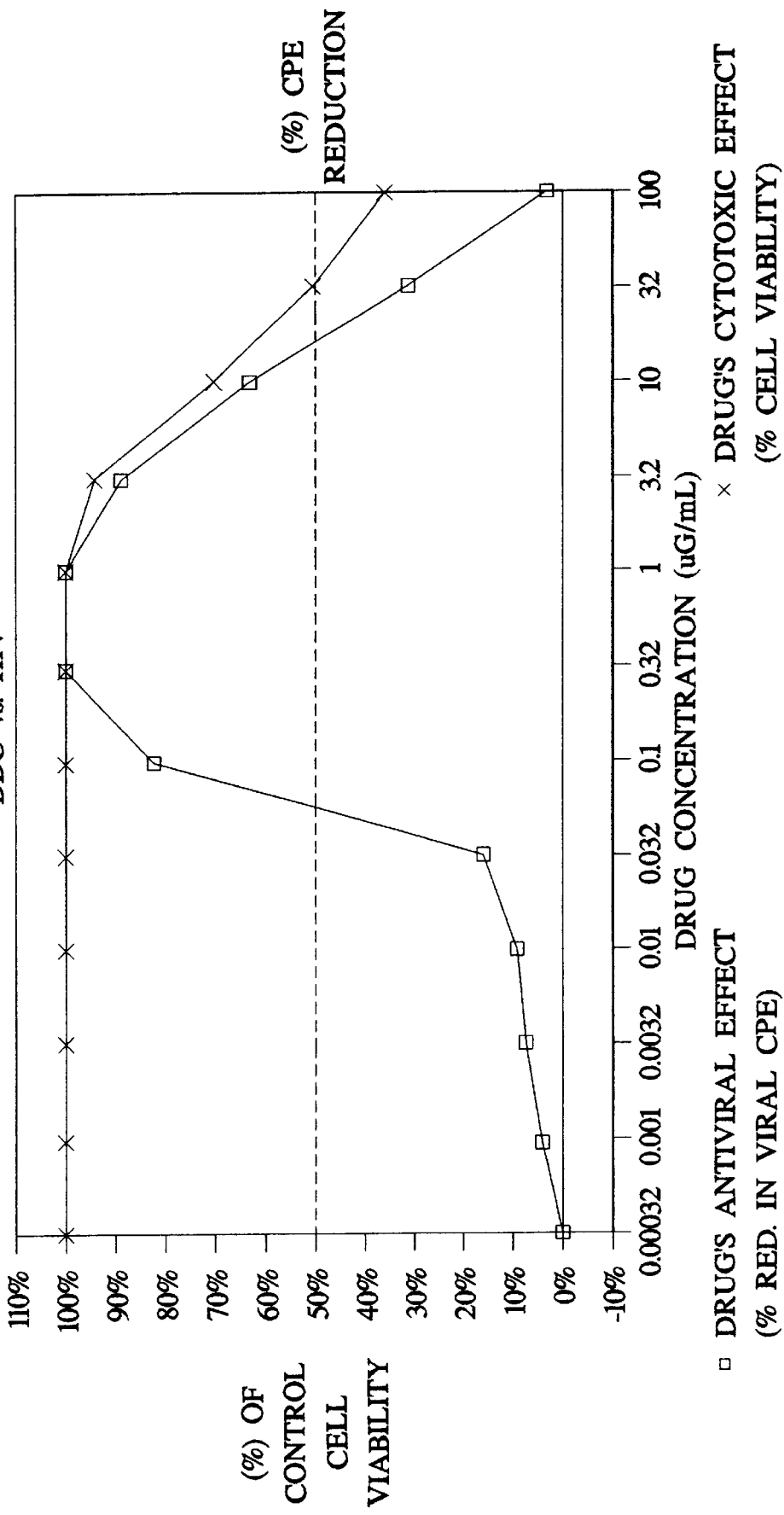
FIGS. 3(a) to 3(e) illustrate in vitro MTT assay results, as described in Example 37, using A-17 HIV viral strain which is resistant to non-nucleoside inhibitors such as TIBO but is sensitive to AZT.
Figure 3B:
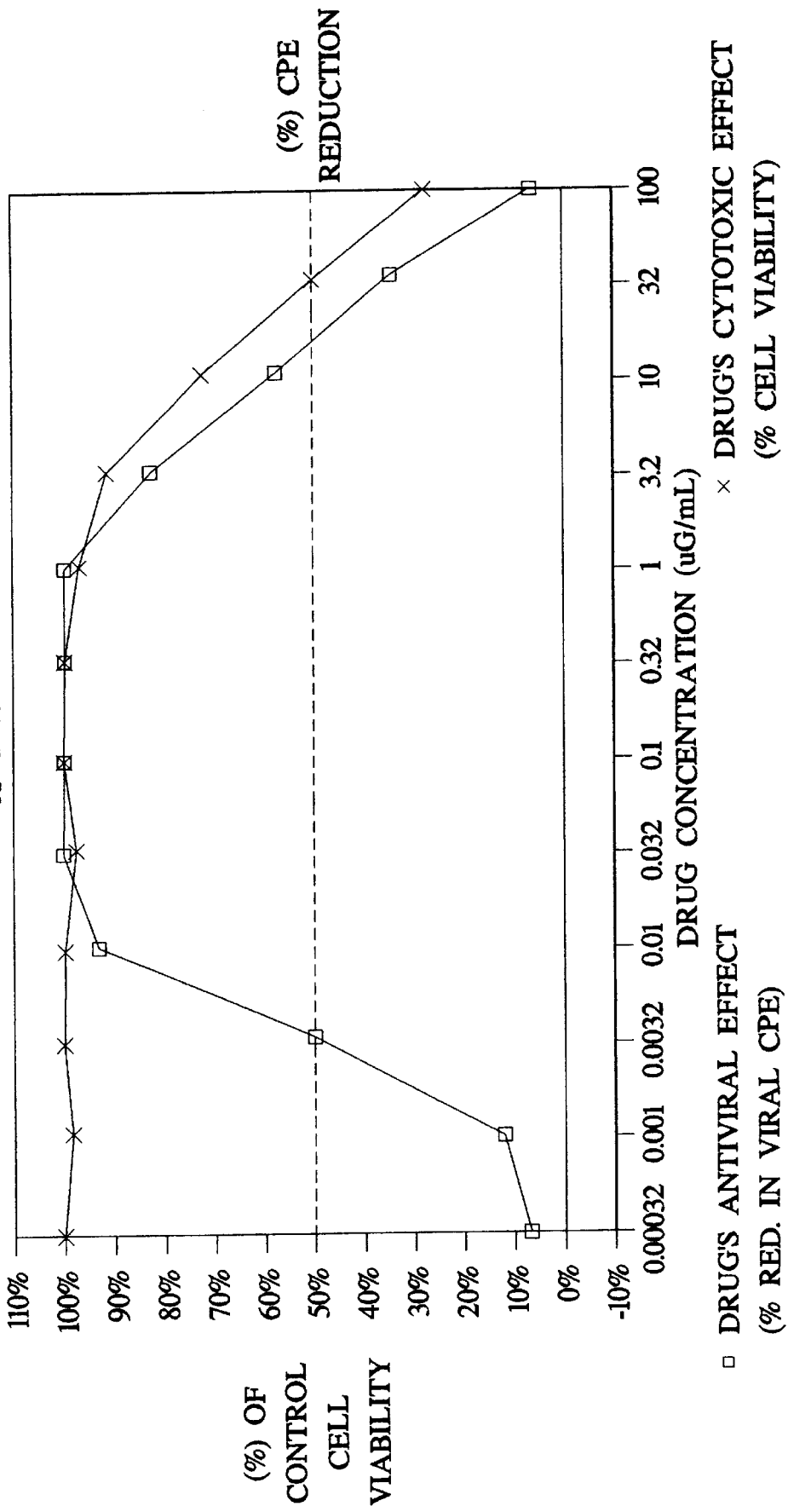
Figure 3C:
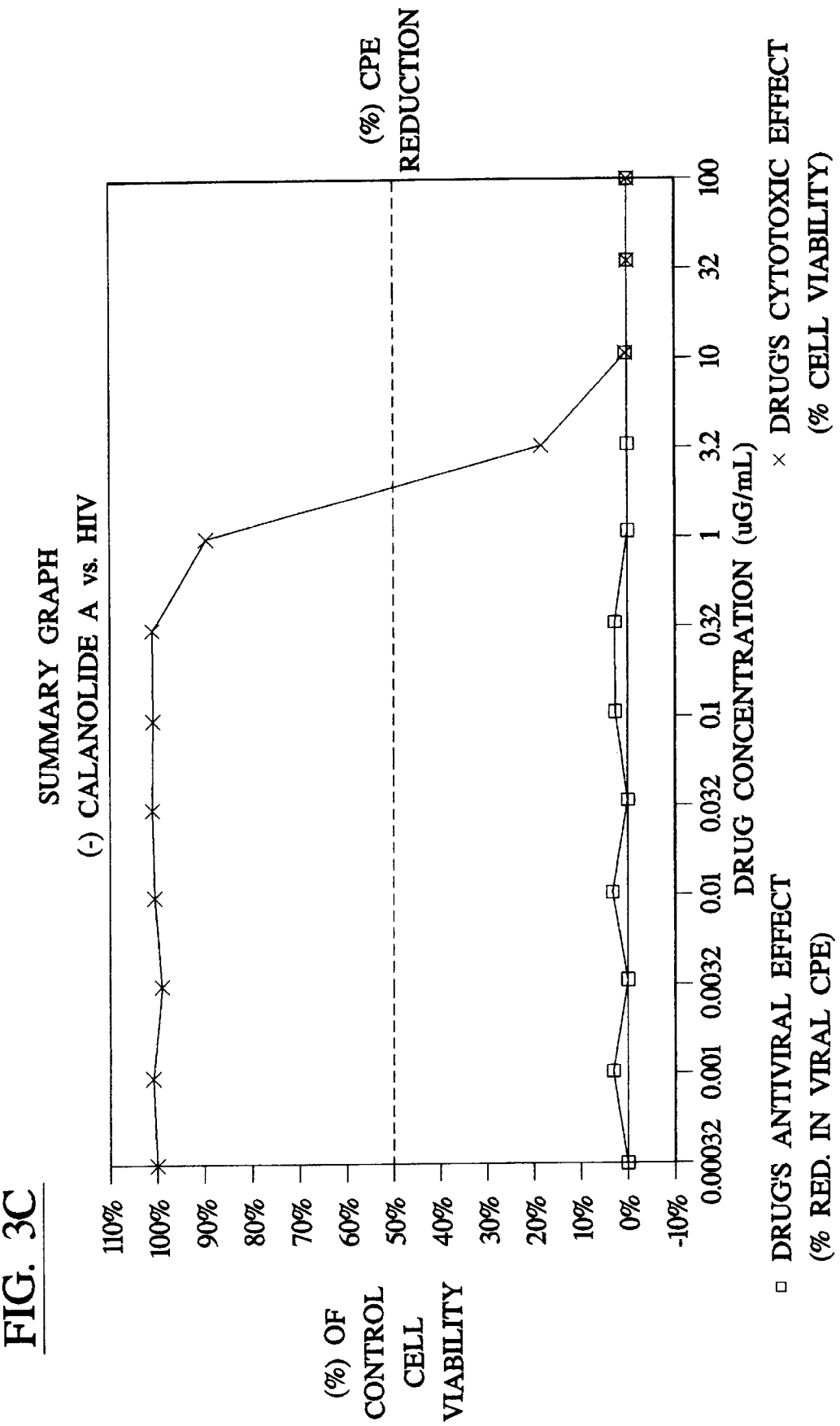
Figure 3D:
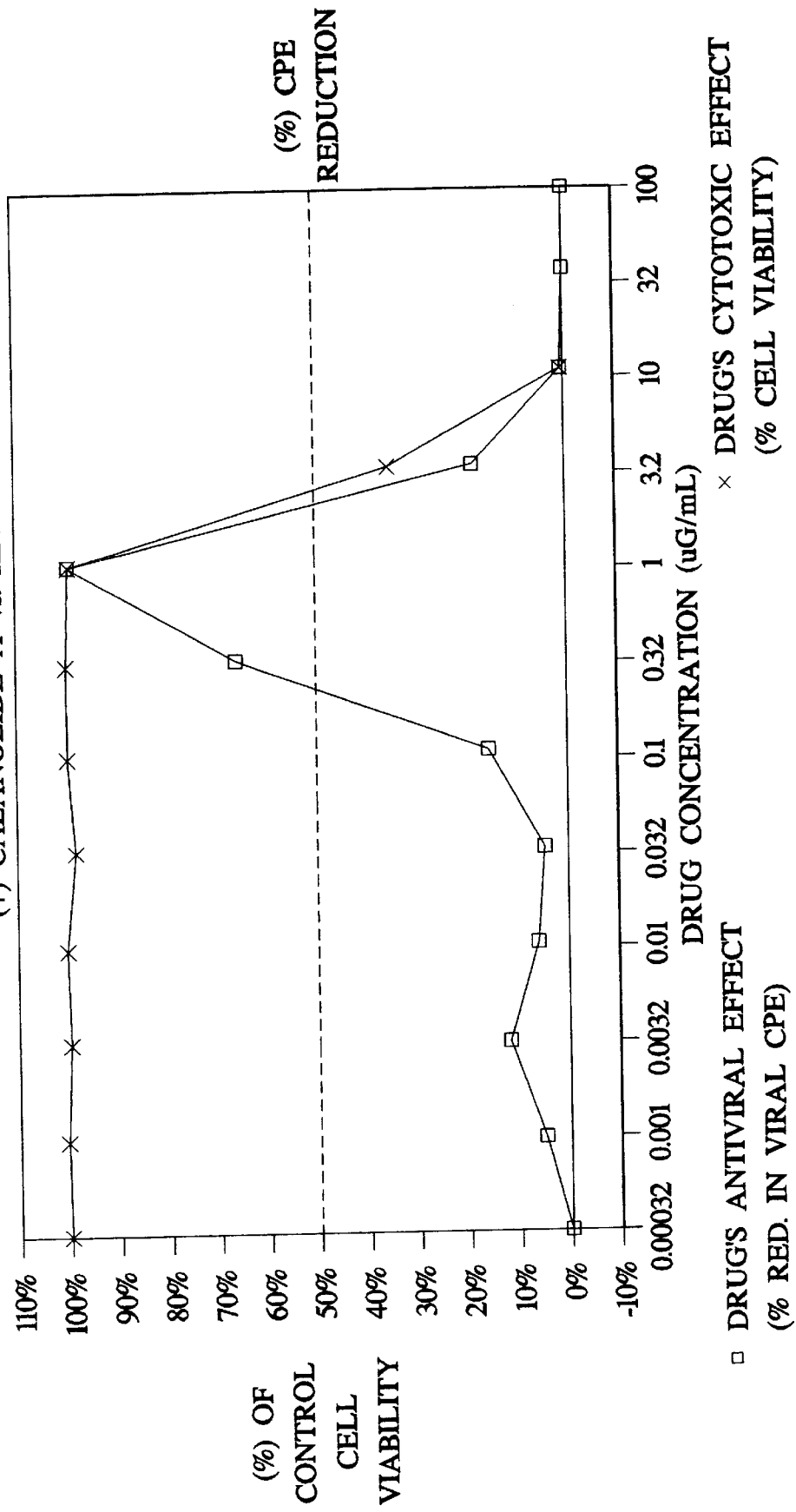
Figure 3E:
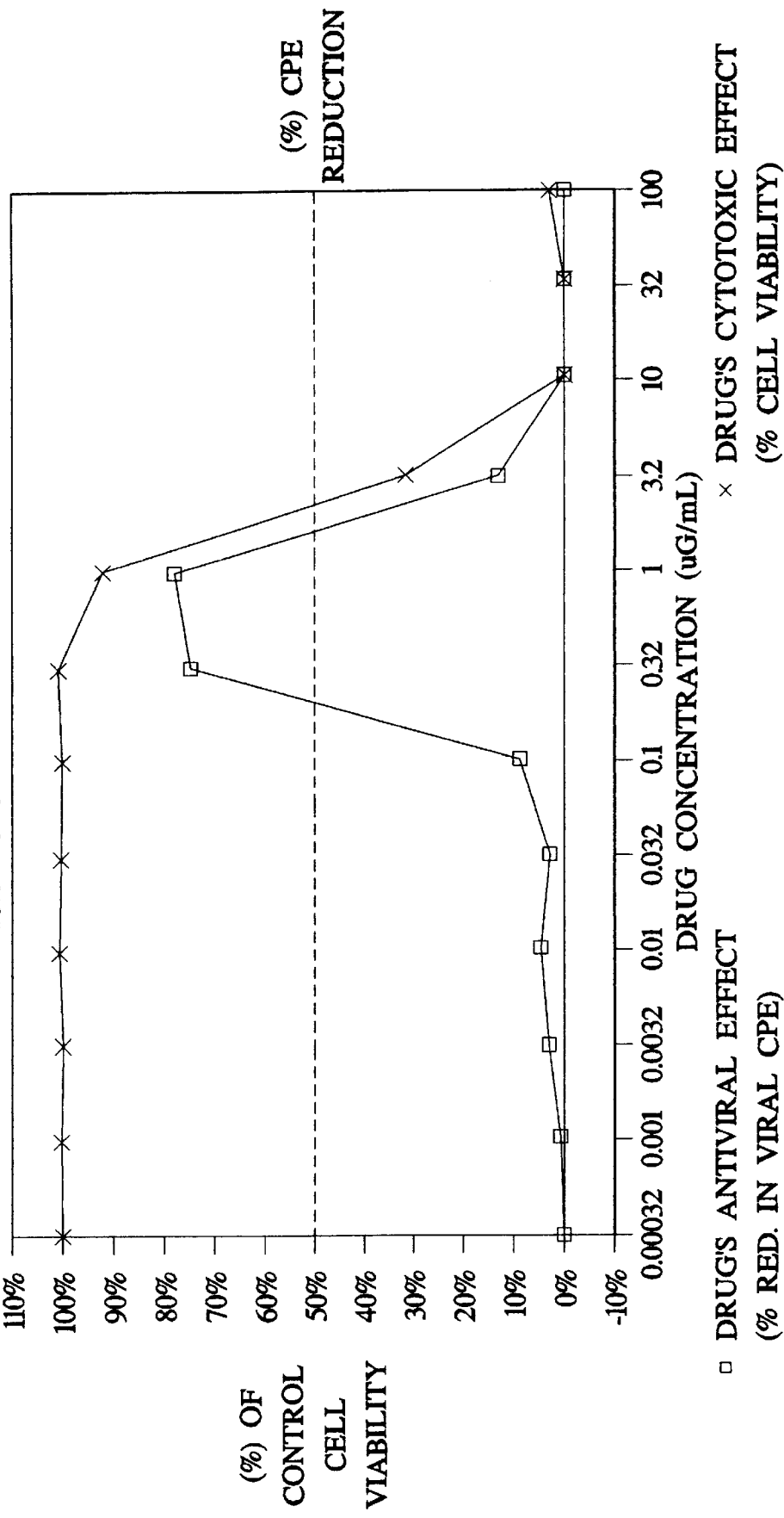

FIGS. 3(a) to 3(e) illustrate in vitro MTT assay results using A-17 HIV viral strain[20] which is resistant to to non-nucleoside inhibitors such as TIBO but is sensitive to AZT. The results here parallel those shown in FIGS. 2(a)–2(e).

Figure 4A:
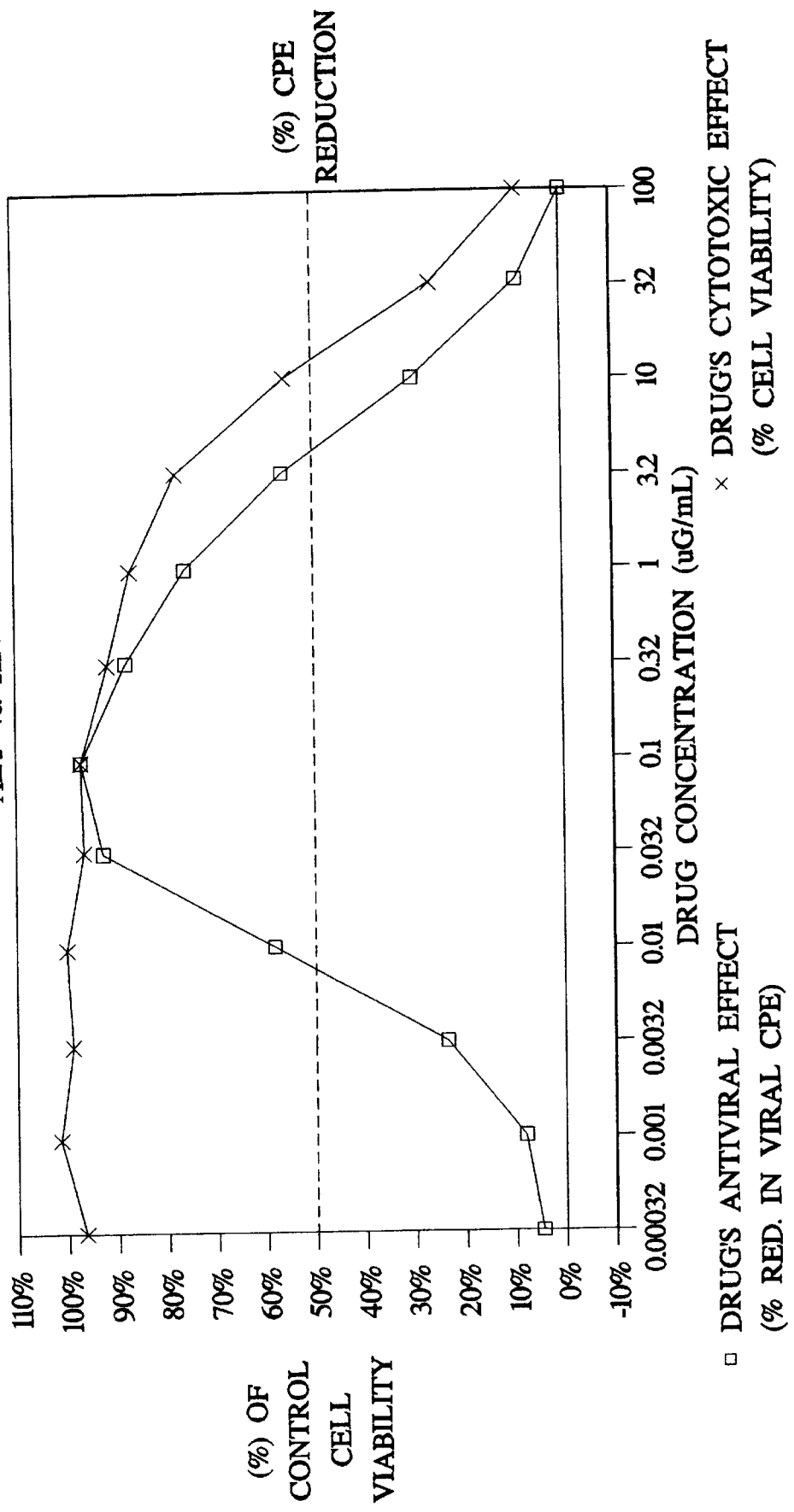
Figure 4B:
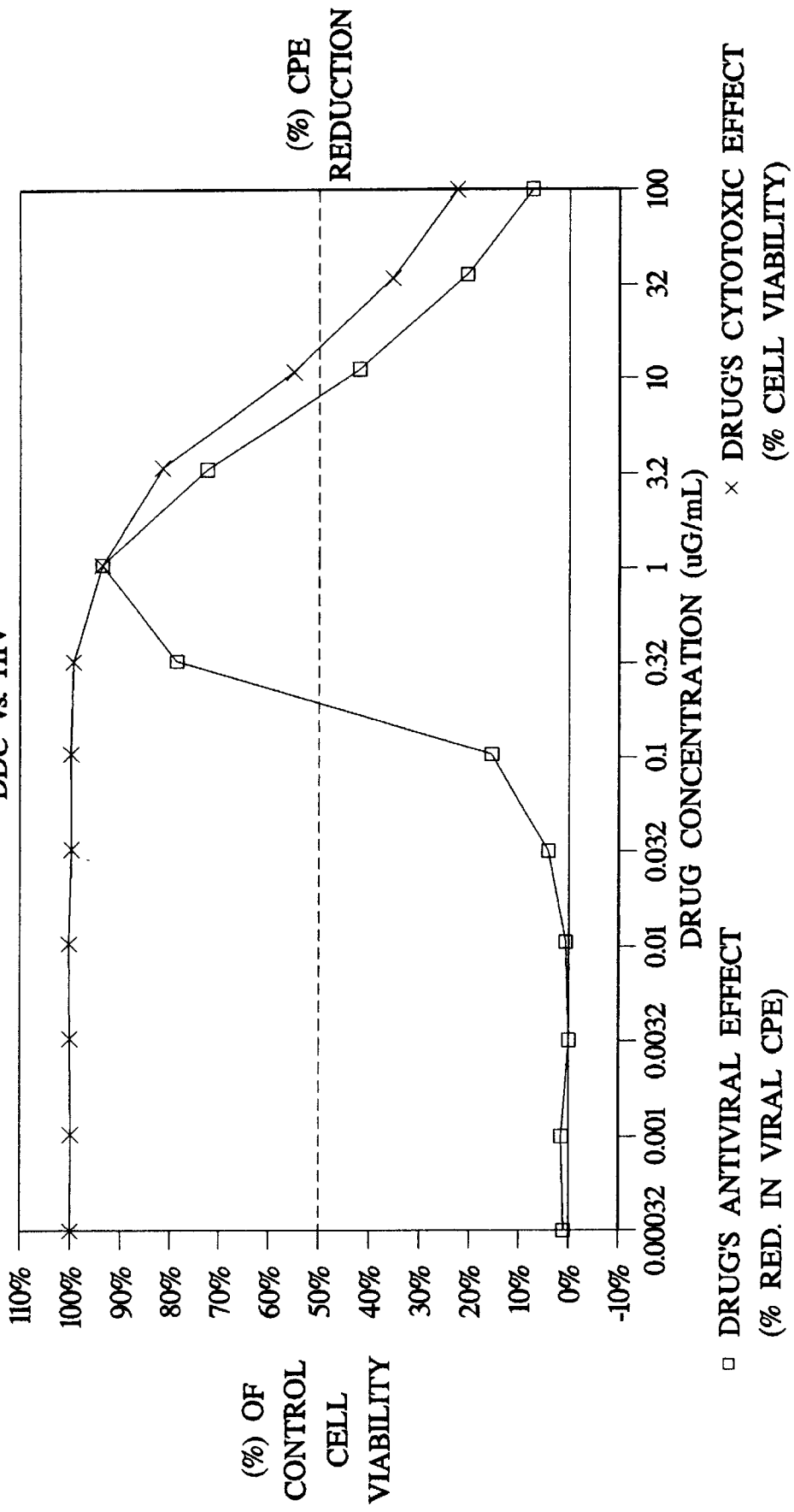
Figure 4D:
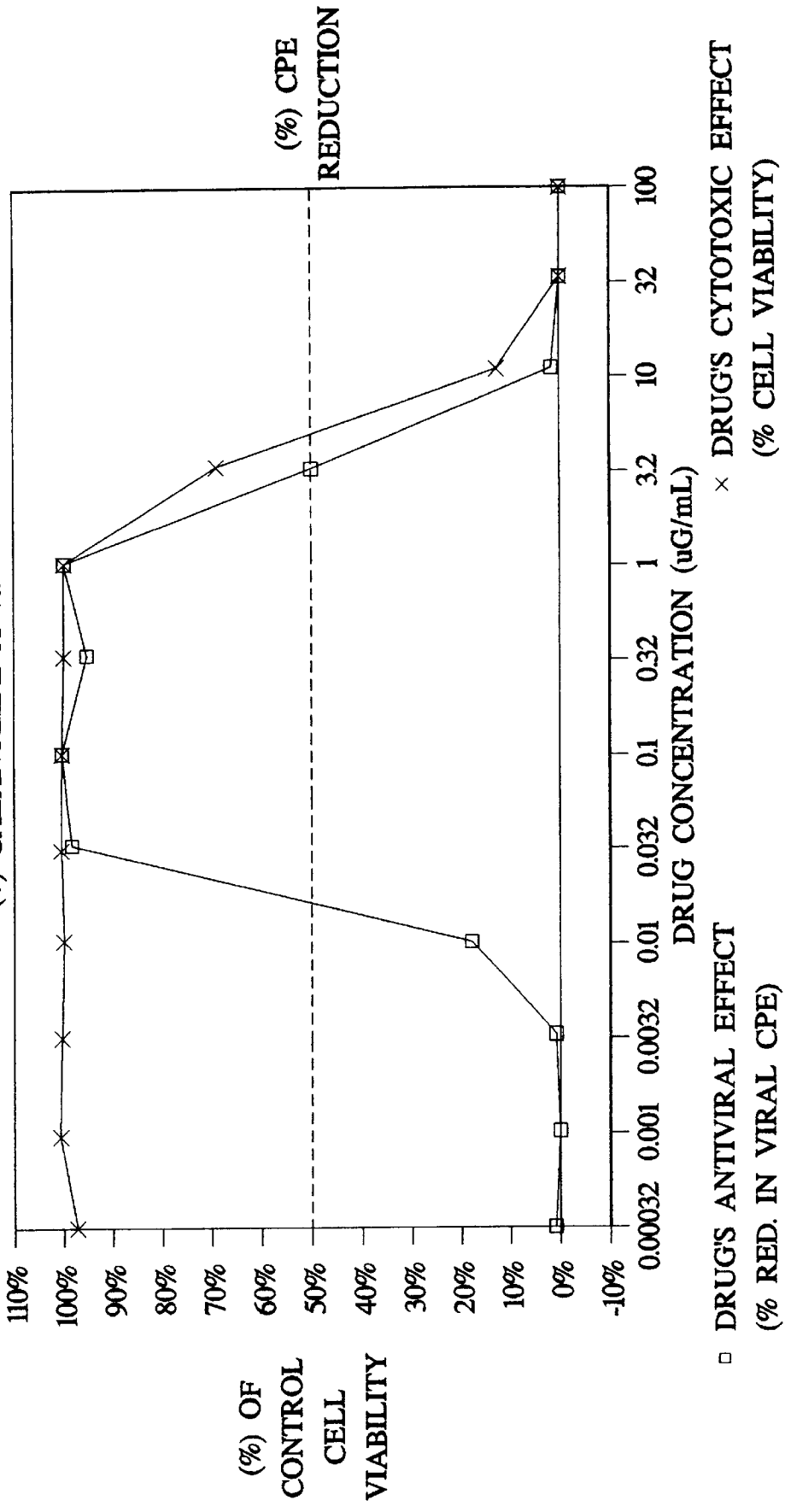
Figure 5A:
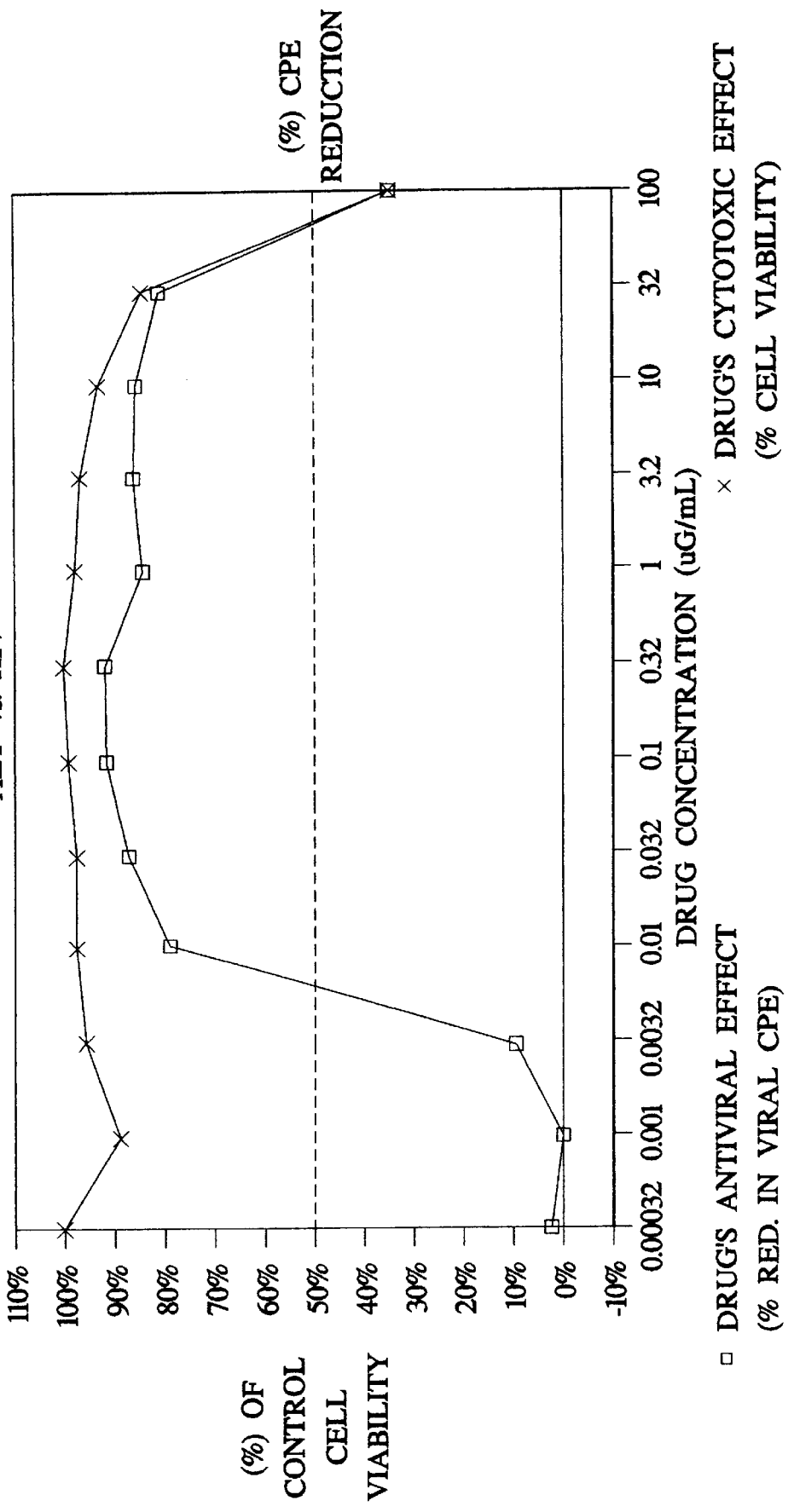
FIGS. 5(a) to 5(d) illustrate in vitro MTT assay results, as described in Example 37, using RF cultivated HIV viral strain.
Figure 5B:
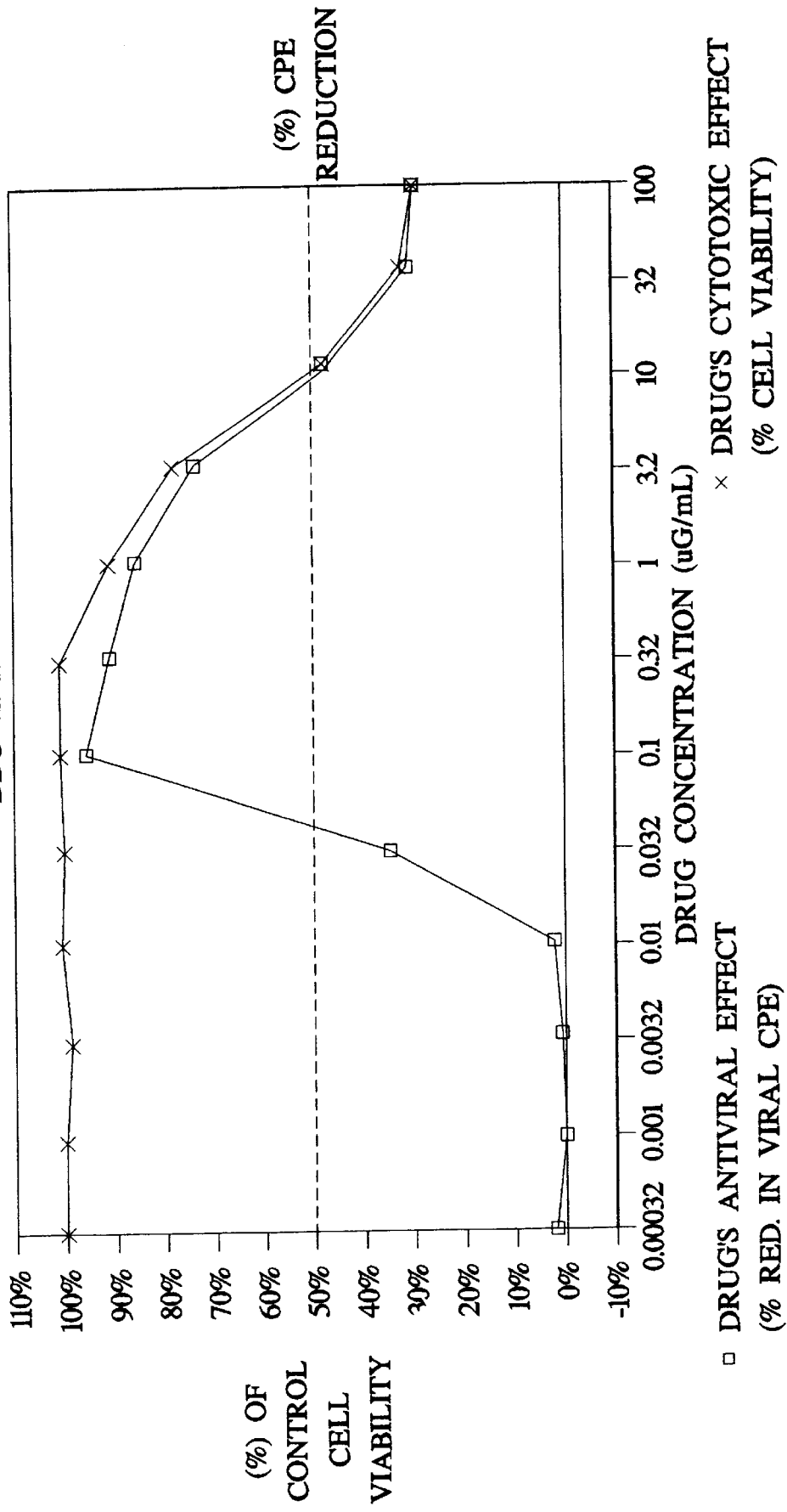
Figure 5C:
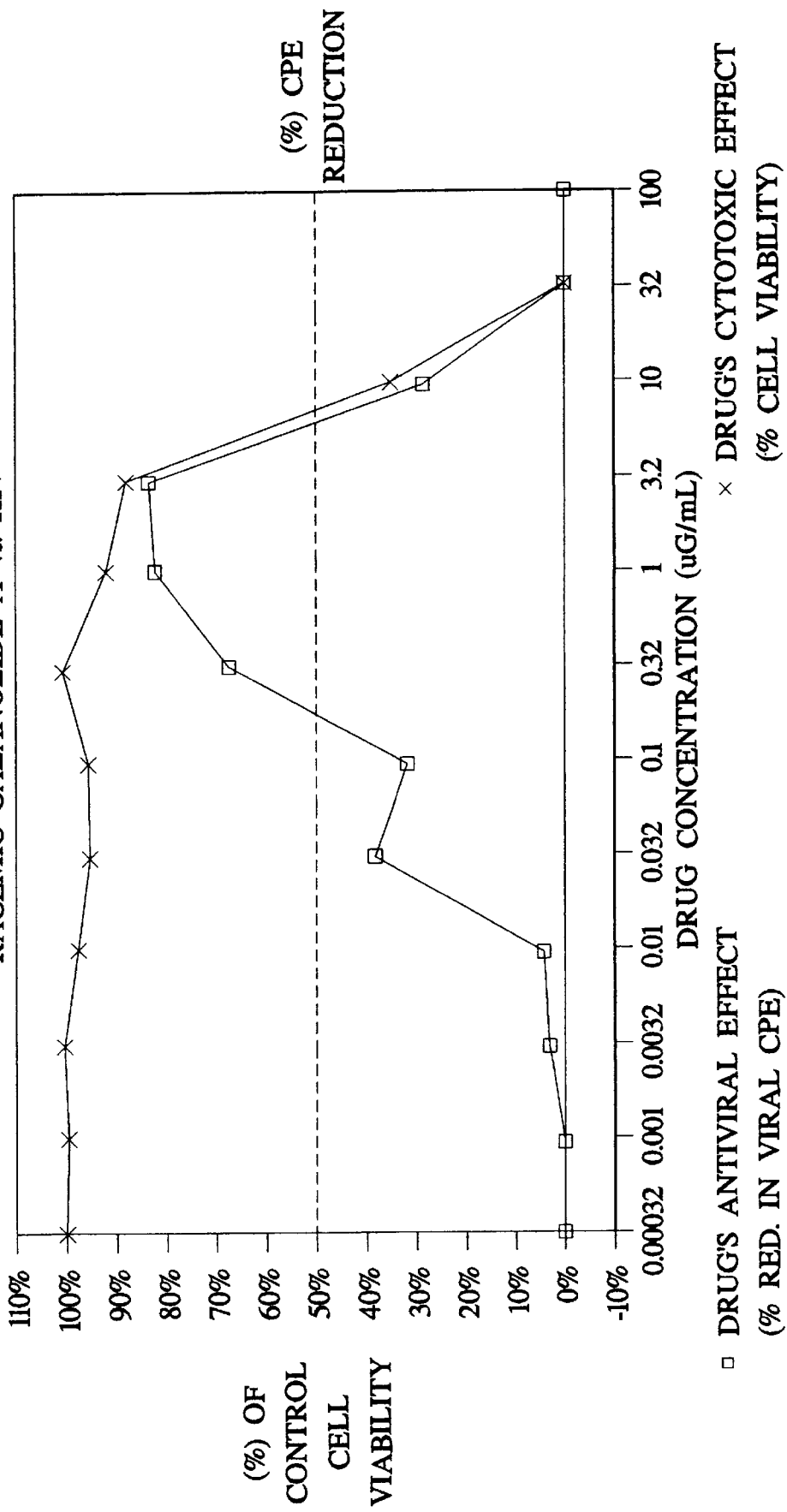
Figure 5D:
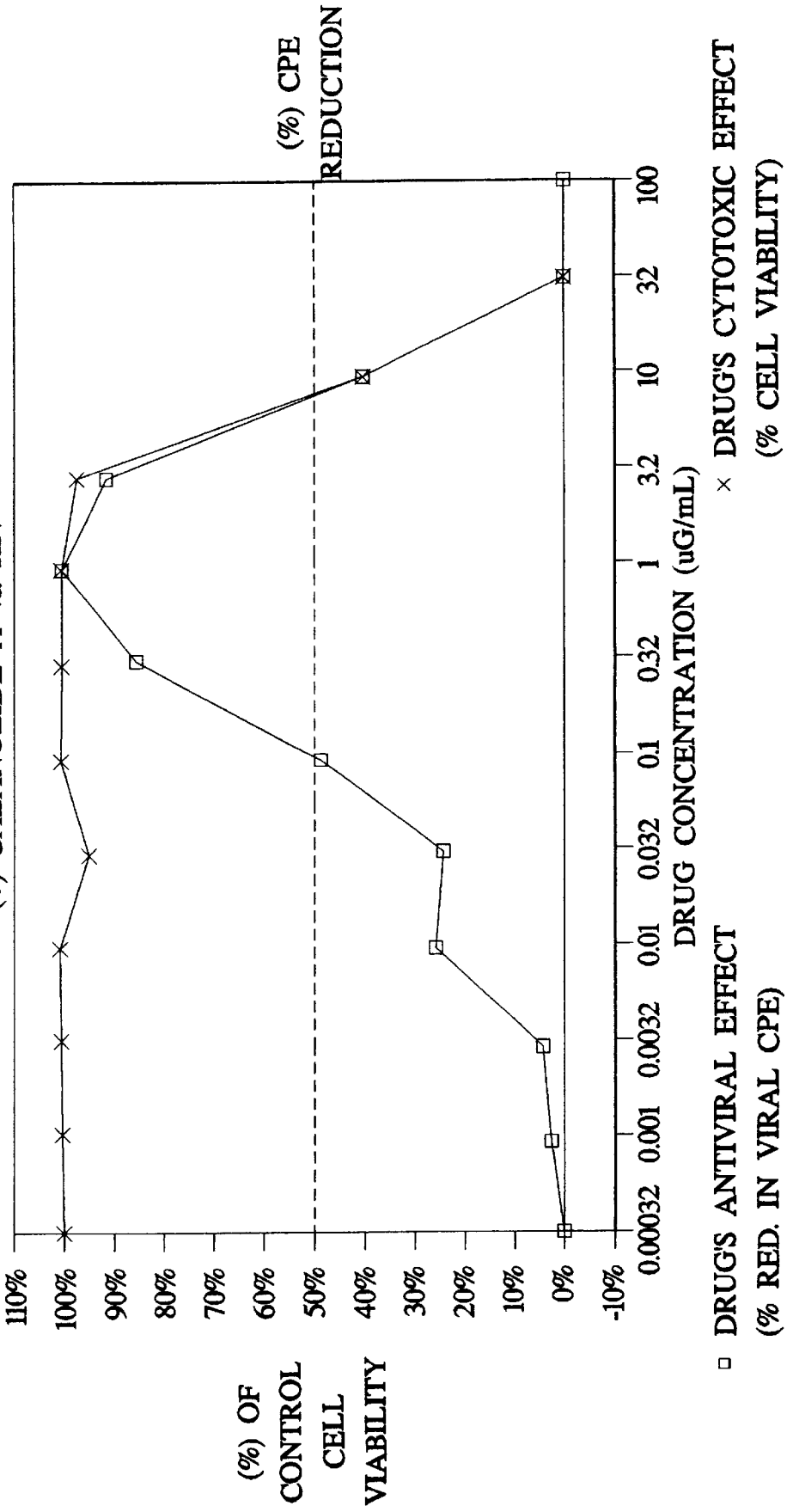
Figure 7A:
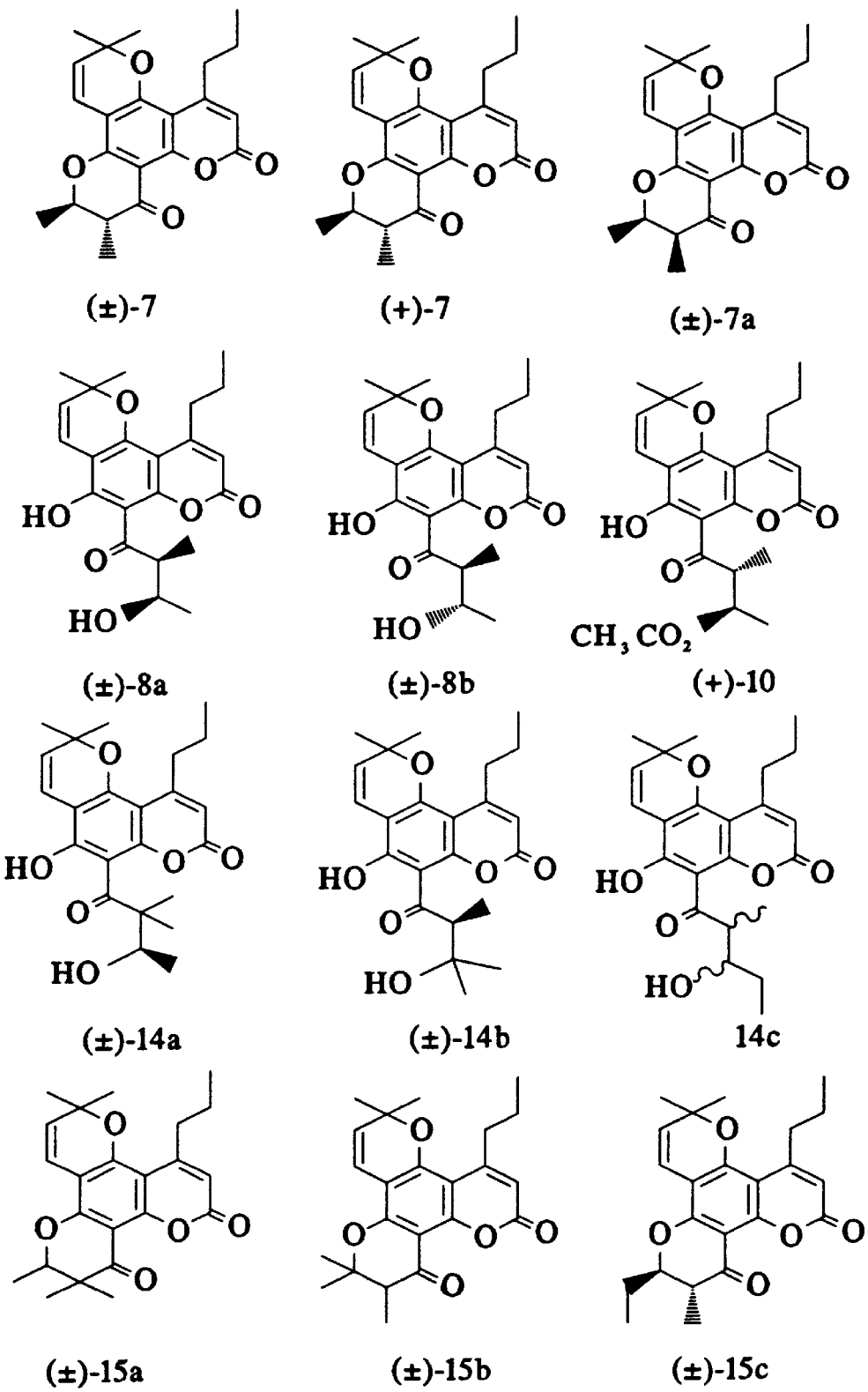
FIG. 7 illustrates representative examples of inventive compounds that were evaluated in the in vitro MTT assay of Example 38.
Figure 7B:
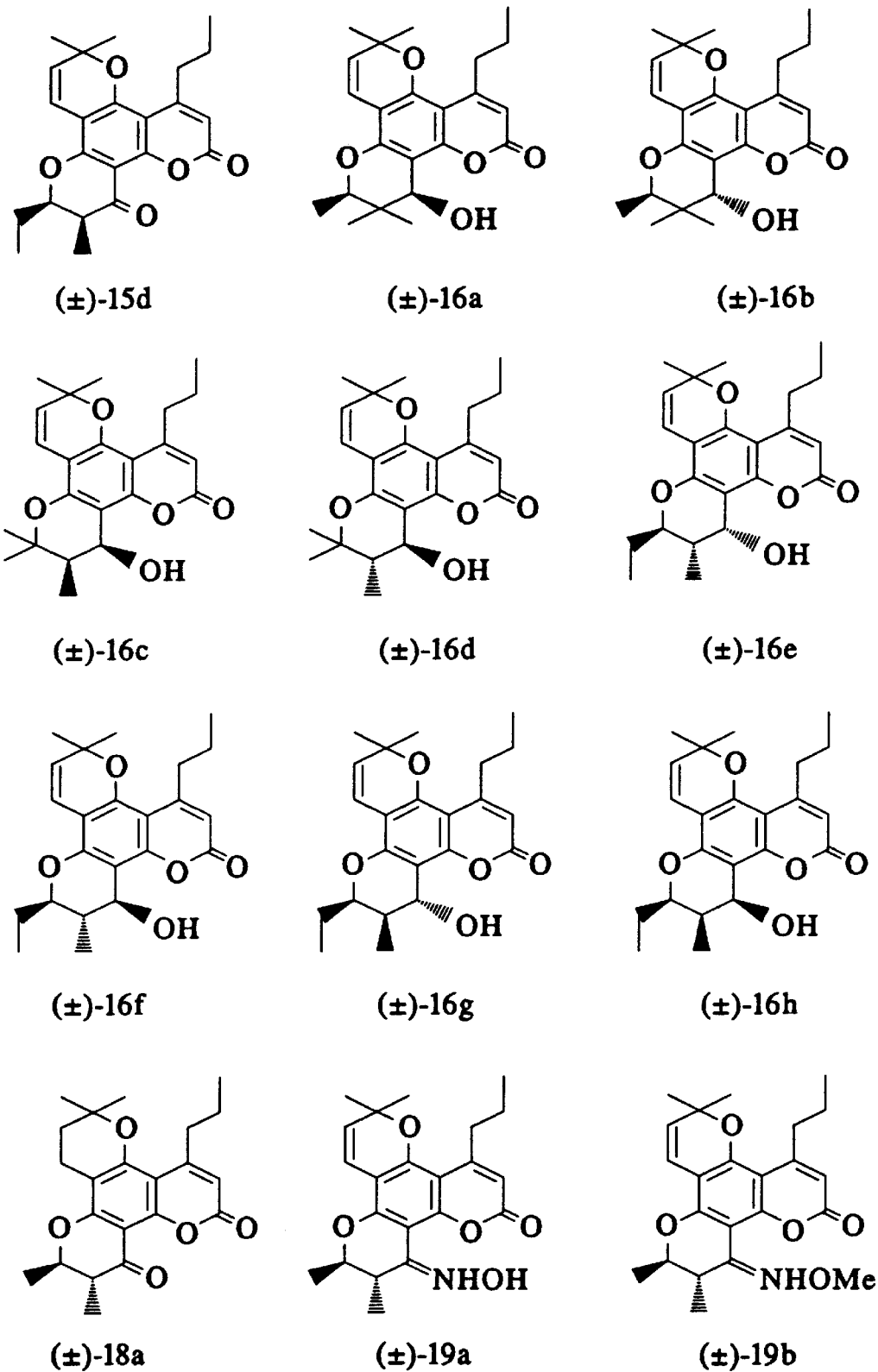
Figure 7C:
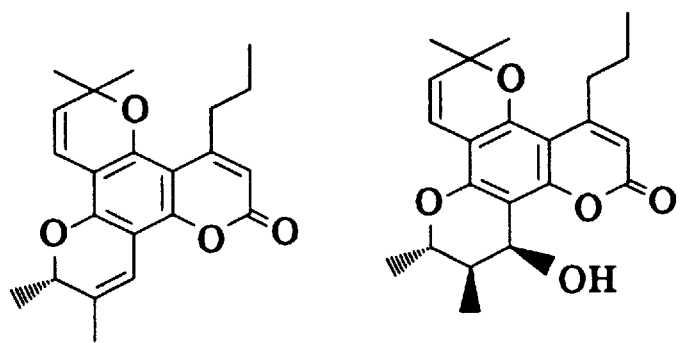

FIGS. 4(a)–(d) and 5(a)–(d) illustrate in vitro MTT assay results using lab cultivated HIV viral strains IIIB and RF, respectively. The results here also parallel those shown in FIGS. 2(a)–2(e).

EXAMPLE 38

IX Vitro Evaluation of Calanolide Analogues

Selected calanolide A intermediates and analogues, prepared as described above, were evaluated using the in vitro MTT-tetrazolium assay described in Example 37. As shown in the Table below, compounds (±)-7, (+)-7, (±)-8a, (±)-8b, (+)-10, (±)-16b, (±)-16d, (±)-16e, and (±)-16f were highly efficacious in protecting cells against HIV infection.

TABLE

In Vitro Anti-HIV-1 Activity of Analogues[a]

| Compound | Maximum Protection (%) | $ED_{50}$ (μM) | $IC_{50}$ (μM) | TI[b] |
|---|---|---|---|---|
| (±)-7 | 90 | 1.18 | 19.10 | 16 |
| (±)-7 | 90 | 0.68 | 72.80 | 107 |
| (±)-7a | 55 | 2.82 | 12.00 | 4 |
| (±)-8a | 84 | 6.16 | 23.8 | 4 |
| (±)-8b | 81 | 2.28 | 21.50 | 9 |
| (±)-10 | 88 | 0.89 | 9.27 | 11 |
| (±)-14a | c | c | 37.00 | c |
| (±)-14b | c | c | 27.10 | c |
| (±)-15a | c | c | 19.30 | c |
| (±)-15b | c | c | 21.00 | c |
| (±)-15c | 47 | c | 6.80 | c |
| (±)-16a | c | c | 20.30 | c |
| (±)-16b | 78 | 2.36 | 16.90 | 7 |
| (±)-16c | c | c | 21.30 | c |
| (±)-16d | 88 | 5.66 | 21.00 | 4 |
| (±)-16e | 88 | 1.67 | 14.00 | 8 |
| (±)-16f | 86 | 1.97 | 17.70 | 9 |
| (±)-16g | c | c | 11.60 | c |
| (±)-16h | c | c | 20.90 | c |
| (±)-18a | 60 | 2.47 | 9.19 | 4 |
| (±)-19a | c | c | 15.80 | c |
| (±)-19b | c | >100 | >100 | c |
| 22 | c | c | 24.70 | c | a. CEM-SS MTT assay
b. $IC_{50}/EC_{50}$
c. not measurable

REFERENCES

1a. Brookmeyer, R., Reconstruction and Future Trends of the AIDS Epidemic in the United States, *Science,* 1991, 253, 37–42.
b. Brain, M. M.; Heyward, W. L.; Curran, J. W., The Global Epidemiology of HIV Infection and AIDS, *Annu. Rev. Microbiol.,* 1990, 44, 555–577.
2a. Weislow, O. S.; Kiser, R.; Fine, D. L.: Bader, J. Shoemaker, R. H.; Boyd, M. R., New Soluble-formazan Assay for HIV-1 Cytopathic Effects: Application to High-Flux Screening of Synthetic and Natural Products of AIDS-Antiviral Activity. *J. Natl. Cancer Inst.,* 1989, 81, 577–586.
b. Mitsuya, H.; Yarchoan, R.; Broder, S., Molecular Targets for AIDS Therapy. *Science,* 1990, 249, 1533–1544.
c. Petteway, S. R., Jr.; Lambert, D. M.; Metcalf, B. W., The Chronically Infected Cells: A Target for the Treatment of HIV Infection and AIDS. *Trends Pharmacol. Sci.,* 1991, 12, 28–34.
d. Richman, D. D., Antiviral Therapy of HIV Infection, *Annu. Rev. Med.,* 1991, 42, 69–90.
e. Haden, J. W., Immunotherapy of Human Immunodeficiency Virus Infection. *Trends Pharmacol Sci.,* 1991, 12, 107–111.
f. Huff, J. R., HIV Protease: A Novel Chemotherapeutic Target for AIDS. *J. Med. Chem.,* 1991, 34, 2305–2314.
g. De Clercq, E., HIV Inhibitors Targeted at the Reverse Transcriptase. *AIDS Research and Human Retroviruses,* 1992, 8, 119–134.
3. Kashman, Y.; Gustafson, K. R.; Fuller, R. W.; Cardellina, J. H., II; McMahon; J. B.; Currens, M. J.; Buckheit, R. W., Jr.; Hughes, S. H.; Cragg, G. M.; Boyd, M. R., The Calanolides, a Novel HIV-Inhibitory Class of Coumarin Derivatives from the Tropical Rainforest Tree, *Calophyllum lanigerum. J. Med. Chem.* 1992, 35, 2735–2743.
4. Boyd, M. R., National Cancer Institute, Personal Communication.

5. Chenera, B.; West, M. L.; Finkelstein, J. A.; Dreyer, G. B., Total Synthesis of (±)-Calanolide A, a Non-Nucleoside Inhibitor of HIV-1 Reverse Transcriptase. *J. Org. Chem.* 1993, 58, 5605–5606.
6. Sethna, S.; Phadke, R., The Pechmann Reaction. *Organic Reactions*, 1953, 7, 1–58 and references cited therein.
7a. Hughes, D. L., The Mitsunobu Reaction. *Organic Reaction*, 1992, 42, 335–656 and references cited therein.
7b. Mitsunobu, O., The Use of Diethyl Azodicarboxylate and Triphenylphosphine in Synthesis and Transformation of Natural Products. *Synthesis*, 1981, 1–28.
7c. Castro, B. R., Replacement of Alcoholic Hydroxyl Groups by Halogens and Other Nucleophiles via Oxyphosphonium Intermediates. *Org. React.* 1983, 29, 1–162.
7d. Hudlicky, M., Fluorination with Diethylaminosulfur Trifluoride and Related Aminofluorosulfuranes. *Org. React.* 1988, 35, 513–637.
8. Gemal, A. L.; Luche, J. L., Lanthanoids in Organic Synthesis. 6. The Reduction of α-Enones by Sodium Borohydride in the Presence of Lanthanoid Chlorides: Synthetic and Mechanistic Aspects. *J. Am. Chem. Soc.*, 1981, 103, 5454–5459.
9a. Feuer, H.; Vincent, B. F., Jr.; Bartlett, R. S., The Reduction of Oximes with Diborane. A New Synthesis of N-Monosubstituted Hydroxylamines. *J. Org. Chem.*, 1965, 30, 2877–2880.
9b. Feuer, H.; Braunstein, D. M., The Reduction of Oximes, Oxime Ethers, and Oxime Esters with Diborane. A Novel Synthesis of Amines. *J. Org. Chem.*, 1969, 34, 1817–1821.
9c. Borch, R. F.; Bernstein, M. D.; Durst, H. D., The Cyanohydridoborate Anion as a Selective Reducing Agent. *J. Amer. Chem. Soc.*, 1971, 93, 2897–2904.
10. For a review, see Nielsen, A. T.; Houlihan, W. J., The Aldol Condensation. *Org. React.* 1968, 16, 1–438.
11. For reviews, see:
   (a) Mukaiyama, T., The Directed Aldol Reaction. *Org. React.* 1982, 28, 203–331.
   (b) Reetz, M. T., Chelation or Non-Chelation Control in Addition Reactions of Chiral α- and β-Alkoxy Carbonyl Compounds, *Angew. Chem. Int. Ed. Eng.* 1984, 23, 556–569.
   (c) Shibata, I.; Baba, A., Organotin Enolates in Organic Synthesis. *Org. Prep. Proc. Int.* 1994, 26, 85–100.
12. For a review on chiral titanium complexes, see Duthaler, R. O.; Hafner, A., Chiral Titanium Complexes for Enantioselective Addition of Nucleophiles to Carbonyl Groups. *Chem. Rev.*, 1992, 92, 807–832 and reference cited therein.
13. For a review on chiral boron complexes, see Paterson, L.; Goodman, J. M.; M., Aldol Reactions in Polypropionate Synthesis: High π-Face Selectivity of Enol Borinates from α-Chiral Methyl and Ethyl Ketones under Substrate Control. *Tetrahedron Lett.* 1989, 30, 7121–7124 and references cited therein.
14. Tsunoda, T.; Yamamiya, Y.; Kawamura, Y.; Ito, S., Mitsunobu Acylation of Sterically Congested Secondary Alcohols by N,N,N¹,N¹-Tetramethylazodicarboxamide-Tributylphosphine Reagents. *Tetrahedron Lett.* 1995, 36, 2529–2530.
15. Crombie, L.; Jones, R. C. F.; Palmer, C. J., Synthesis of the Mammea Coumarin. Part 1. The Coumarin of the Mammea A, B, and C Series. *J. Chem. Soc., Perkin Trans.* 1, 1987, 317–331.
16. Very recently, a similar work has been published in the literature; Cardellina, J. H., II; Bokesch, H. R.; McKee, T. C.; Boyd, M. R., Resolution and Comparative Anti-HIV Evaluation of the Enantiomers of Calanolides A and B. *Bioorg. Med. Chem. Lett.* 1995, 5, 1011–1014.
17. Deshpande, P. P., Tagliaferri, F.; Victory, S. F.; Yan, S.; Baker, D. C., Synthesis of Optically Active Calanolides A and B. *J. Org. Chem.* 1995, 60, 2964–2965.
18. Gulakowski, R. J.; McMahon, J. B.; Staley, P. G.; Moran, R. A.; Boyd, M. R., A semiautomated Multiparameter Approach for Anti-HIV Drug Screening, *J. Virol. Methods*, 1991, 33, 87–100.
19. Larder, B. A.; Darby, G.; Richman, D. D., HIV with reduced Sensitivity to Zidovudine (AZT) isolated during Prolonged Therapy, *Science*, 1989, 243, 1731–1734.
20. Nunberg, J. H.; Schlief, W. A.; Boots, E. J.; O'Brien, J. A.; Quintero, J. C.; Hoffman, J. M.; Emini, E. A.; Goldman, M. E., Viral Resistance to Human Immunodeficiency Virus Type 1-specific Pyridinone Reverse Transcriptase, *J. Virol.*, 1991, 65, 4887–4892.

What is claimed is:

1. A process for preparing a compound of formula I:

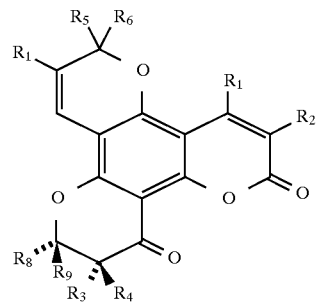

wherein $R_1$ is H, halogen, hydroxyl, amino, $C_{1-6}$ alkyl, aryl-$C_{1-6}$ alkyl, mono- or poly-fluorinated $C_{1-6}$ alkyl, hydroxy-$C_{1-6}$ alkyl, $C_{1-6}$ alkoxy, amino-$C_{1-8}$ alkyl, $C_{1-6}$ alkylamino, di($C_{1-6}$ alkyl)amino, $C_{1-8}$ alkylamino-$C_{1-8}$ alkyl, di($C_{1-6}$ alkyl) amino-$C_{1-8}$ alkyl, cyclohexyl, aryl, or heterocycle, wherein aryl or heterocycle may each be unsubstituted or substituted with one or more of the following: $C_{1-6}$ alkyl, $C_{1-6}$ alkoxy,hydroxy-$C_{1-4}$ alkyl, hydroxyl, amino, $C_{1-6}$ alkylamino, di($C_{1-6}$ alkyl)amino, amino-$C_{1-8}$ alkyl, $C_{1-8}$ alkylamino-$C_{1-8}$ alkyl, di($C_{1-6}$ alkyl-amino-$C_{1-8}$ alkyl, nitro, azido or halogen;

$R_2$ is H, halogen, hydroxyl, $C_{1-6}$ alkyl, aryl-$C_{1-6}$ alkyl, mono- or poly-fluorinated $C_{1-6}$ alkyl, aryl or heterocycle;

$R_3$ and $R_4$ are independently selected from the group consisting of H, halogen, hydroxyl, amino, $C_{1-6}$ alkyl, aryl-$C_{1-6}$ alkyl, mono- or poly-fluorinated $C_{1-6}$ alkyl, hydroxy-$C_{1-6}$ alkyl, amino-$C_{1-8}$ alkyl, $C_{1-8}$ alkylamino-$C_{1-8}$ alkyl, di($C_{1-6}$ alkyl)amino-$C_{1-8}$ alkyl, cyclohexyl, aryl or heterocycle; and $R_3$ and $R_4$ can be taken together to form a 5–7 membered saturated cycle ring or heterocyclic ring;

$R_5$ and $R_6$ are independently selected from the group consisting of H, $C_{1-6}$ alkyl, aryl-$C_{1-6}$ alkyl, mono- or poly-fluorinated $C_{1-6}$ alkyl, aryl or heterocycle; $R_5$ and $R_6$ can be taken together to form a 5–7 membered saturated cycle ring or heterocycle ring;

$R_7$ is H, halogen, methyl, or ethyl;

$R_8$ and $R_9$ are independently selected from the group consisting of H, halogen, $C_{1-6}$ alkyl, aryl-$C_{1-6}$ alkyl, mono- or poly-fluorinated $C_{1-6}$ alkyl, hydroxy-$C_{1-6}$ alkyl, amino-$C_{1-8}$ alkyl, $C_{1-8}$ alkylamino-$C_{1-8}$ alkyl, di($C_{1-6}$ alkyl)amino-$C_{1-8}$ alkyl, cyclohexyl, aryl or heterocycle; and $R_8$ and $R_9$ can be taken together to form a 5–7 membered saturated cycle ring or heterocyclic ring;

or a pharmaceutically acceptable salt thereof, the process comprising:
(a) reacting phloroglucinol, in the presence of an acid catalyst, with a β-ketoester of formula i

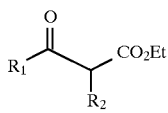

wherein $R_1$ and $R_2$ is as defined above so as to produce coumarin 11 (Scheme V);
(b) acylating coumarin 11 (Scheme V) with an acylating agent of formula ii

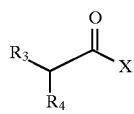

wherein X is halogen or $OCOCHR_3R_4$ wherein $R_3$ and $R_4$ are defined above so as to produce 8-substituted coumarin 12 (Scheme V);
(c) reacting coumarin 12 (Scheme V), under basic conditions, with a β-hydroxyaldehyde dimethylacetals of formula iii

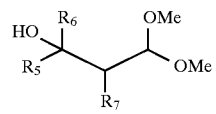

wherein $R_5$, $R_6$ and $R_7$ are as defined above so as to produce chromene 13 (Scheme V);
(d) condensing chromene 13 (Scheme V) with a carbonyl compound of formula iv

wherein $R_8$ and $R_9$ are as defined above in the presence of a base so as to form a compound of formula II:

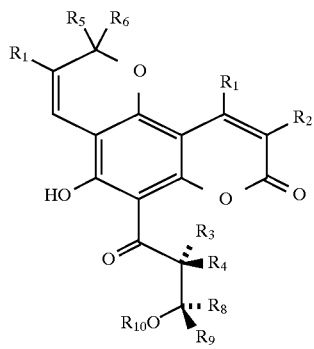

wherein $R_1$, $R_2$, $R_3$, $R_4$, $R_5$, $R_6$, $R_7$, $R_8$, and $R_9$ are as defined above and $R_{10}$=H; and
(e) cyclizing of formula II compound under Mitsunobu conditions so as to produce a compound of formula I.

2. The process according to claim 1, wherein step (d) base comprises LDA.

3. The process according to claim 1, wherein step (d) condensation is mediated by a metal complex.

4. The process according to claim 3, wherein said metal complex is $TiCl_4$.

5. The process according to claim 1, wherein step (e) cyclization is performed with diethyl azodicarboxylate and triphenylphosphine.

6. The process according to claim 1, further comprising step (f) enzymatically resolving and separating enantiomers of formula II, prior to step (e).

7. The process according to claim 1, further comprising step (g) reducing formula I compound to produce a formula III compound wherein $R_{10}$=OH.

8. The process according to claim 7, further comprising step (h) hydrogenating formula III compound so as to produce dihydro analogue formula IV compound.

9. The process according to claim 1, further comprising step (i) hydrogenating formula I compound so as to produce a dihydro analogue formula V compound.

10. The process according to claim 7, wherein $R_1$=n-propyl; $R_2$=$R_4$=$R_7$=$R_8$=H; $R_3$=$R_5$=$R_6$=$R_9$=Me; and $R_{10}$=β-OH.

11. The process according to claim 1, wherein $R_1$=n-propyl; $R_2$=$R_3$=$R_7$=$R_9$=H; $R_4$=$R_5$=$R_6$=$R_8$=Me; and $R_{10}$=β-OH.

12. A compound of the formula:

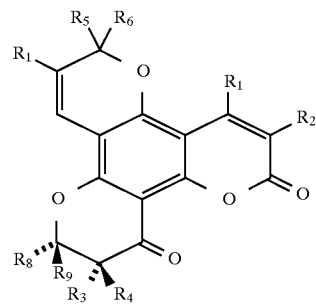

wherein
$R_1$ is H, halogen, hydroxyl, amino, $C_{1-6}$ alkyl, aryl-$C_{1-6}$ alkyl, mono- or poly-fluorinated$_{1-6}$ alkyl, hydroxy-$C_{1-6}$ alkyl, $C_{1-6}$ alkoxy, amino-$C_{1-8}$ alkyl, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl, cyclohexyl, aryl or heterocycle, wherein aryl or heterocycle may each be unsubstituted or substituted with one or more of the following: $C_{1-6}$ alkyl, $C_{1-6}$ alkoxy, hydroxy-$C_{1-4}$ alkyl, hydroxyl, amino, $C_{1-6}$ alkylamino, di($C_{1-6}$ alkyl)amino, amino-$C_{1-8}$ alkyl, $C_{1-8}$ alkylamino-$C_{1-8}$ alkyl, di($C_{1-6}$ alkyl)amino-$C_{1-8}$ alkyl, nitro, azido or halogen;

$R_2$ is H, halogen, hydroxyl, $C_{1-6}$ alkyl, aryl-$C_{1-6}$ alkyl, mono- or poly-fluorinated $C_{1-6}$ alkyl, aryl or heterocycle;

$R_3$ and $R_4$ are independently selected from the group consisting of H, halogen, hydroxyl, amino, $C_{1-6}$ alkyl, aryl-$C_{1-6}$ alkyl, mono- or poly-fluorinated $C_{1-6}$ alkyl, hydroxy-$C_{1-6}$ alkyl, amino-$C_{1-8}$ alkyl, $C_{1-8}$ alkylamino-$C_{1-8}$ alkyl, di($C_{1-6}$ alkyl)amino-$C_{1-8}$ alkyl, cyclohexyl, aryl or heterocycle; and $R_3$ and $R_4$ can be taken together to form a 5–7 membered saturated cycle ring or heterocyclic ring;

$R_5$ and $R_6$ are independently selected from the group consisting of H, $C_{1-6}$ alkyl, aryl-$C_{1-6}$ alkyl, mono- or poly-fluorinated $C_{1-6}$ alkyl, aryl or heterocycle; and $R_5$ and $R_6$ can be taken together to form a 5–7 membered saturated cycle ring or heterocyclic ring;

$R_7$ is H, halogen, methyl, or ethyl;

$R_8$ and $R_9$ are independently selected from the group consisting of H, halogen, $C_{1-6}$ alkyl, aryl-$C_{1-6}$ alkyl, mono- or poly-fluorinated $C_{1-6}$ alkyl, amino-$C_{1-8}$ alkyl $C_{1-8}$ alkylamino-$C_{1-8}$ alkyl,di($C_{1-6}$ alkyl)amino-$C_{1-8}$ alkyl, cyclohexyl, aryl or heterocycle; and $R_8$ and $R_9$ and be taken together to form a 5–7 membered saturated cycle ring or heterocyclic ring;

or a pharmaceutically acceptable salt thereof, alone or in combination with a carrier, with the proviso that (a) when $R_1$ equals phenyl: (i) $R_2$, $R_3$, $R_7$ and $R_9$ not equal hydrogen; and $R_1$, $R_5$, $R_6$, and $R_8$ not equal methyl; (ii) $R_2$, $R_4$, $R_7$, $R_8$ not equal hydrogen and $R_3$, $R_5$, $R_6$, and not equal methyl; or (iii) $R_2$, $R_4$, $R_7$, and $R_9$ not equal hydrogen; and and $R_3$, $R_5$, $R_6$, and $R_8$ not equal methyl; (iv) $R_2$, $R_3$, $R_7$, $R_8$ not equal hydrogen and $R_4$, $R_5$, $R_6$, and $R_9$ not equal methyl, at the same time; and (b) when $R_1$ equals n-propyl: (i) $R_2$, $R_4$, $R_7$, $R_8$ not equal H; and $R_3$, $R_5$, $R_6$, $R_9$ not equal methyl; (ii) $R_2$, $R_3$, $R_7$, $R_9$ not equal H, and $R_4$, $R_5$, $R_6$, $R_8$ not methyl; (iii) $R_2$, $R_3$, $R_7$, $R_8$ not equal H; and $R_4$, $R_5$, $R_6$, $R_9$ not equal methyl; or (iv) $R_2$, $R_4$, $R_7$, $R_9$ not equal H; and $R_3$, $R_5$, $R_6$, $R_8$ not equal methyl, at the same time.

13. The compound of claim 12 wherein $R_3$ is methyl.

14. The compound of claim 13 wherein $R_4$ is H.

15. The compound of claim 14 wherein $R_8$ is H.

16. The compound of claim 15 wherein $R_9$ is methyl.

17. The compound of claim 16 wherein $R_1$ is phenyl.

18. The compound of claim 16 wherein $R_1$ is n-propyl.

19. The compound of claim 12, wherein $R_1$=n-propyl; $R_2$=$R_7$=$R_8$=H; $R_3$=$R_4$=$R_9$=methyl; or its enantiomer.

20. The compound of claim 12, wherein $R_1$=n-propyl; $R_2$=$R_4$=$R_7$=H $R_8$=$R_9$=$R_3$=methyl; or its enantiomer.

21. The compound of claim 12, wherein $R_1$=n-propyl; $R_2$=$R_7$=$R_4$=$R_8$=H; $R_9$=ethyl; $R_3$=methyl; or its enantiomer.

22. The compound of claim 12, wherein $R_1$=n-propyl $R_2$=$R_3$=$R_7$=$R_8$=H; $R_2$=ethyl; $R_4$=methyl; or its enantiomer.

* * * * *